(12) United States Patent
Yoshida et al.

(10) Patent No.: US 9,266,851 B2
(45) Date of Patent: Feb. 23, 2016

(54) FLUORENE-CONTAINING AROMATIC COMPOUND, MATERIAL FOR ORGANIC ELECTROLUMINESCENT ELEMENT, AND ORGANIC ELECTROLUMINESCENT ELEMENT USING SAME

(75) Inventors: Kei Yoshida, Sodegaura (JP); Kazuki Nishimura, Sodegaura (JP); Mitsunori Ito, Sodegaura (JP); Yuichiro Kawamura, Sodegaura (JP); Toshinari Ogiwara, Sodegaura (JP); Toshihiro Iwakuma, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1071 days.

(21) Appl. No.: 13/386,240

(22) PCT Filed: Oct. 14, 2010

(86) PCT No.: PCT/JP2010/068079
§ 371 (c)(1),
(2), (4) Date: Jan. 20, 2012

(87) PCT Pub. No.: WO2011/046182
PCT Pub. Date: Apr. 21, 2011

(65) Prior Publication Data
US 2012/0126217 A1    May 24, 2012

(30) Foreign Application Priority Data

Oct. 16, 2009  (JP) .................. 2009-239786

(51) Int. Cl.
| | |
|---|---|
| H01L 51/50 | (2006.01) |
| C07D 307/91 | (2006.01) |
| C07D 209/86 | (2006.01) |
| C07D 401/10 | (2006.01) |
| C07D 401/14 | (2006.01) |
| C07D 403/10 | (2006.01) |
| C07D 403/14 | (2006.01) |
| C07D 405/14 | (2006.01) |
| C07D 409/12 | (2006.01) |
| C07D 409/14 | (2006.01) |
| C07D 471/04 | (2006.01) |
| H01L 51/00 | (2006.01) |
| C09B 57/00 | (2006.01) |
| C09B 57/10 | (2006.01) |
| C09B 69/00 | (2006.01) |

(52) U.S. Cl.
CPC ............ *C07D 307/91* (2013.01); *C07D 209/86* (2013.01); *C07D 401/10* (2013.01); *C07D401/14* (2013.01); *C07D 403/10* (2013.01); *C07D 403/14* (2013.01); *C07D 405/14* (2013.01); *C07D 409/12* (2013.01); *C07D 409/14* (2013.01); *C07D 471/04* (2013.01); *C09B 57/00* (2013.01); *C09B 57/008* (2013.01); *C09B 57/10* (2013.01); *C09B 69/008* (2013.01); *H01L 51/0071* (2013.01); *H01L 51/5016* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 7,550,594 | B2 | 6/2009 | Okajima et al. |
| 7,632,578 | B2 | 12/2009 | Lee et al. |
| 2004/0086745 | A1 | 5/2004 | Iwakuma et al. |
| 2004/0115476 | A1 | 6/2004 | Oshiyama et al. |
| 2004/0157084 | A1 | 8/2004 | Lee et al. |
| 2005/0127823 | A1 | 6/2005 | Iwakuma et al. |
| 2005/0164032 | A1 | 7/2005 | Ise et al. |
| 2005/0249976 | A1 | 11/2005 | Iwakuma et al. |
| 2006/0041126 | A1 | 2/2006 | Schäfer et al. |
| 2006/0051616 | A1 | 3/2006 | Suzuki et al. |
| 2006/0097227 | A1 | 5/2006 | Okajima et al. |
| 2006/0134460 | A1 | 6/2006 | Kondakova et al. |
| 2006/0141284 | A1 | 6/2006 | Tomita et al. |
| 2006/0154105 | A1* | 7/2006 | Yamamoto et al. ........... 428/690 |
| 2006/0180806 | A1 | 8/2006 | Arakane et al. |
| 2006/0251918 | A1 | 11/2006 | Iwakuma |

| | | | |
|---|---|---|---|
| 2006/0257684 A1 | 11/2006 | Arakane et al. | |
| 2007/0051944 A1 | 3/2007 | Vestweber et al. | |
| 2007/0052346 A1 | 3/2007 | Iwakuma et al. | |
| 2007/0069638 A1 | 3/2007 | Matsuura et al. | |
| 2007/0090753 A1 | 4/2007 | Arakane | |
| 2007/0141387 A1 | 6/2007 | Nakano et al. | |
| 2007/0159083 A1 | 7/2007 | Matsuura et al. | |
| 2007/0172698 A1 | 7/2007 | Iwakuma et al. | |
| 2007/0188083 A1 | 8/2007 | Iwakuma et al. | |
| 2007/0190355 A1 | 8/2007 | Ikeda et al. | |
| 2007/0194701 A1 | 8/2007 | Ito et al. | |
| 2007/0224448 A1 | 9/2007 | Ikeda et al. | |
| 2007/0257600 A1 | 11/2007 | Matsuura et al. | |
| 2007/0296328 A1 | 12/2007 | Matsuura et al. | |
| 2008/0145699 A1 | 6/2008 | Yabe et al. | |
| 2008/0206597 A1 | 8/2008 | Iwakuma | |
| 2009/0072732 A1 | 3/2009 | Arakane et al. | |
| 2009/0091240 A1* | 4/2009 | Ikeda et al. | 313/504 |
| 2009/0102363 A1 | 4/2009 | Haga et al. | |
| 2009/0218940 A1 | 9/2009 | Okajima et al. | |
| 2009/0224658 A1 | 9/2009 | Iwakuma et al. | |
| 2009/0243473 A1 | 10/2009 | Iwakuma et al. | |
| 2009/0284138 A1 | 11/2009 | Yasukawa et al. | |
| 2009/0302743 A1 | 12/2009 | Kato et al. | |
| 2009/0309488 A1 | 12/2009 | Kato et al. | |
| 2010/0039026 A1 | 2/2010 | Yang et al. | |
| 2010/0044689 A1 | 2/2010 | Nishimura et al. | |
| 2010/0051106 A1 | 3/2010 | Kim et al. | |
| 2010/0084971 A1 | 4/2010 | Nakano et al. | |
| 2010/0163857 A1 | 7/2010 | Kim et al. | |
| 2010/0194270 A1 | 8/2010 | Kawamura et al. | |
| 2010/0200848 A1 | 8/2010 | Arakane et al. | |
| 2010/0207110 A1 | 8/2010 | Nishimura et al. | |
| 2010/0219404 A1 | 9/2010 | Endo et al. | |
| 2010/0240892 A1 | 9/2010 | Schäfer et al. | |
| 2010/0270539 A1 | 10/2010 | Nishimura et al. | |
| 2010/0314644 A1 | 12/2010 | Nishimura et al. | |
| 2011/0042654 A1 | 2/2011 | Jung et al. | |
| 2011/0121277 A1 | 5/2011 | Matsuura et al. | |
| 2011/0248257 A1 | 10/2011 | Kim et al. | |
| 2011/0253995 A1 | 10/2011 | Kato et al. | |
| 2011/0272679 A1 | 11/2011 | Yokoyama et al. | |
| 2011/0309338 A1 | 12/2011 | Iwakuma et al. | |
| 2012/0080670 A1 | 4/2012 | Park et al. | |
| 2012/0085995 A1 | 4/2012 | Kato et al. | |
| 2012/0104940 A1 | 5/2012 | Shin et al. | |
| 2012/0126221 A1 | 5/2012 | Kitamura et al. | |
| 2012/0126690 A1 | 5/2012 | Ise et al. | |
| 2012/0126691 A1 | 5/2012 | Ise et al. | |
| 2012/0126692 A1 | 5/2012 | Ise et al. | |
| 2012/0153267 A1 | 6/2012 | Matsuura et al. | |
| 2012/0235129 A1 | 9/2012 | Iwakuma et al. | |
| 2012/0298975 A1 | 11/2012 | Iwakuma et al. | |
| 2012/0319099 A1 | 12/2012 | Iwakuma et al. | |
| 2012/0326601 A1 | 12/2012 | Yasukawa et al. | |
| 2013/0126849 A1 | 5/2013 | Arakane et al. | |
| 2013/0240858 A1 | 9/2013 | Nishimura et al. | |
| 2014/0001460 A1 | 1/2014 | Iwakuma et al. | |

FOREIGN PATENT DOCUMENTS

| | | | |
|---|---|---|---|
| CN | 101052636 A | 10/2007 | |
| CN | 102292327 A | 12/2011 | |
| EP | 1 724 323 A1 | 11/2006 | |
| EP | 1 808 433 A1 | 7/2007 | |
| EP | 1 962 354 A1 | 8/2008 | |
| EP | 2 256 176 A1 | 1/2010 | |
| EP | 2 166 585 A1 | 3/2010 | |
| EP | 2 166 586 A1 | 3/2010 | |
| EP | 2 182 040 A2 | 5/2010 | |
| EP | 2 380 888 A1 | 10/2011 | |
| EP | 2 461 390 A1 | 6/2012 | |
| JP | 2000 068059 | 3/2000 | |
| JP | 2000 169448 | 6/2000 | |
| JP | 2001 192653 | 7/2001 | |
| JP | 2001 247858 | 9/2001 | |
| JP | 2003-45662 A | 2/2003 | |
| JP | 2003-277743 A | 10/2003 | |
| JP | 2004-2297 A | 1/2004 | |
| JP | 2004-31004 A | 1/2004 | |
| JP | 2004-171808 A | 6/2004 | |
| JP | 2004-214050 A | 7/2004 | |
| JP | 2005-255561 A | 9/2005 | |
| JP | 2005 289914 | 10/2005 | |
| JP | 2007-220721 A | 8/2007 | |
| JP | 2007 261969 | 10/2007 | |
| JP | 2008-147424 A | 6/2008 | |
| JP | 2008-205488 A | 9/2008 | |
| JP | 2009-16693 A | 1/2009 | |
| JP | 2009-21336 A | 1/2009 | |
| JP | 2009-76511 A | 4/2009 | |
| JP | 2009-152528 A | 7/2009 | |
| JP | 2009-152529 A | 7/2009 | |
| JP | 2009-158848 A | 7/2009 | |
| JP | 2009-218547 A | 9/2009 | |
| JP | 2010-185047 A | 8/2010 | |
| JP | 2010-202599 A | 9/2010 | |
| KR | 10-2009-0131958 A | 12/2009 | |
| KR | 10-2010-0121238 A | 11/2010 | |
| KR | 10-2010-0131745 | 12/2010 | |
| TW | 306890 B | 3/2009 | |
| WO | 03 080760 | 10/2003 | |
| WO | 2004 026870 | 4/2004 | |
| WO | 2005 085387 | 9/2005 | |
| WO | 2006 049013 | 5/2006 | |
| WO | WO 2006/049013 A1 | 5/2006 | |
| WO | WO 2008/072539 A1 | 6/2008 | |
| WO | WO 2008-147110 * | 12/2008 | C09K 11/06 |
| WO | WO 2009/008205 A1 | 1/2009 | |
| WO | WO 2009/035296 A2 | 3/2009 | |
| WO | WO 2009/104733 * | 8/2009 | C09K 11/06 |
| WO | WO 2010/044342 A1 | 4/2010 | |
| WO | WO 2010/084729 A1 | 7/2010 | |
| WO | WO 2010/114264 A2 | 10/2010 | |
| WO | WO 2011/037429 A2 | 3/2011 | |

OTHER PUBLICATIONS

Office Action issued Apr. 3, 2013 in Chinese Application No. 201080033813.0 (With English Translation).

Extended European Search Report issued Mar. 1, 2013, in European Patent Application No. 10823450.1.

International Search Report issued on Jan. 18, 2011 in PCT/JP10/068079 filed on Oct. 14, 2010.

Combined Office Action and Search Report issued Nov. 27, 2013 in Chinese Patent Application No. 201080033813.0 with English language translation and English translation of categories of cited documents.

* cited by examiner

*Primary Examiner* — Gregory Clark

(74) *Attorney, Agent, or Firm* — Oblon, McClelland, Maier & Neustadt, L.L.P.

(57) ABSTRACT

A fluorene-containing aromatic compound represented by a formula (1) below.

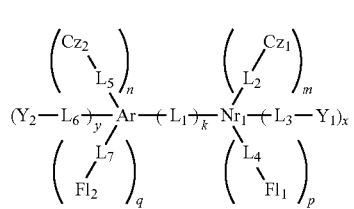

(1)

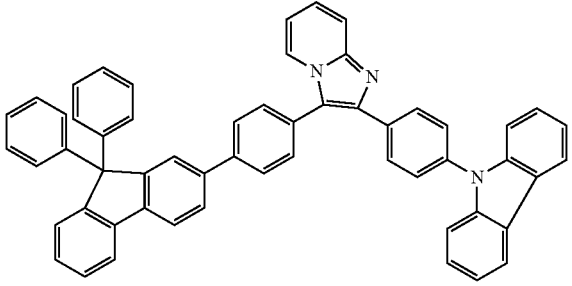

(2)

In the formula (1): $Nr_1$ represents a substituted or unsubstituted monocyclic nitrogen-containing aromatic ring having 2 to 5 ring carbon atoms, or a bicyclic nitrogen-containing aromatic ring having 2 to 9 ring carbon atoms; Ar represents an aromatic ring and the like; $Fl_1$ and $Fl_2$ represent a fluorenyl group; and $Cz_1$ and $Cz_2$ represent a carbazolyl group. A compound represented by a formula (2) below is omitted from the fluorene-containing aromatic compound represented by the formula (1).

28 Claims, 1 Drawing Sheet

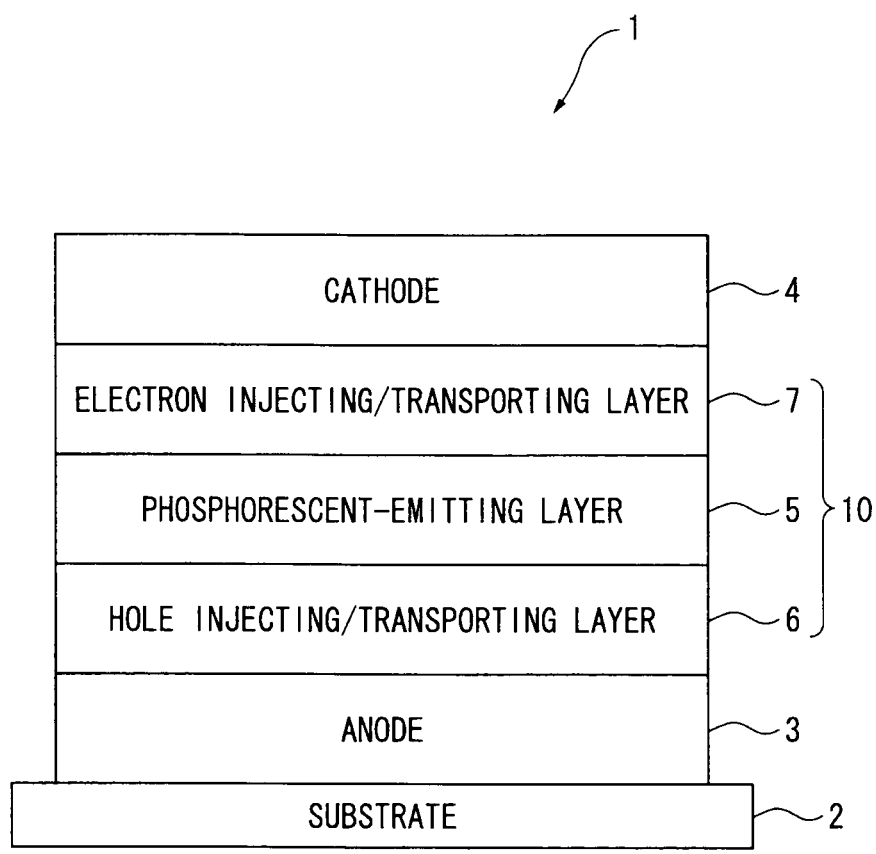

FLUORENE-CONTAINING AROMATIC COMPOUND, MATERIAL FOR ORGANIC ELECTROLUMINESCENT ELEMENT, AND ORGANIC ELECTROLUMINESCENT ELEMENT USING SAME

TECHNICAL FIELD

The present invention relates to a fluorene-containing aromatic compound, a material for an organic electroluminescence device, and an organic electroluminescence device using the material.

BACKGROUND ART

An organic electroluminescence device (hereinafter, electroluminescence is occasionally abbreviated as EL) is a self-emitting device based on the principle that, when an electrical field is applied, a fluorescent material emits light using energy generated by a recombination of holes injected from an anode with electrons injected from a cathode. Studies on an organic EL device formed of an organic material have been vigorously carried out since a layered organic EL device driven at low voltage was reported (for instance, Patent Literatures 1 to 8). In the layered device, tris(8-quinolinolato)aluminum is used as an emitting layer and a triphenyldiamine derivative is used as a hole transporting layer. Advantages of such a layered structure are to improve efficiency of injecting holes into the emitting layer, to improve efficiency of generating excitons by recombination due to blockage of electrons injected from the cathode, to trap the excitons generated in the emitting layer, and the like. As a device structure of such an organic EL device, a two-layered structure, a three-layered structure or the like has been well known. The two-layered structure includes a hole transporting (injecting) layer and an electron transporting/emitting layer. The three-layered structure includes a hole transporting (injecting) layer, an emitting layer and an electron transporting (injecting) layer. In such a layered device, a device structure and a preparation method have been contrived in order to improve efficiency of recombining the injected holes and electrons.

Luminescent materials of an organic EL device such as a chelate complex (e.g. a tris(8-quinolinol)aluminum complex), a coumarin complex, a tetraphenyl butadiene derivative, a distyrylarylene derivative and an oxadiazole derivative have been known. These materials, which have been reported to emit light of blue to red in visible region, are expected to be applied to a color-display device.

Moreover, in addition to a fluorescent material, application of a phosphorescent material has been recently proposed for the emitting layer of the organic EL device. Thus, in the emitting layer of the organic EL device, a singlet state and a triplet state of excited states of an organic phosphorescent material are used to achieve a high luminous efficiency. When electrons and holes are recombined in the organic EL device, it is presumed that a singlet exciton and a triplet exciton are produced at a rate of 1:3 due to difference in spin multiplicity. Accordingly, luminous efficiency of the device using a phosphorescent material can reach three to four times as much as that of the device only using a fluorescent material.

In forming the emitting layer, a doping method, according to which the above luminescent material (dopant) is doped to a host material, has been known.

The emitting layer formed by the doping method can efficiently generate excitons from electric charges injected into the host material. With the exciton energy generated by the excitons being transferred to the dopant, the dopant can emit light with high efficiency.

Recently, in order to upgrade an organic EL device, a further study on the doping method has been made to seek favorable host materials.

Such a host material is disclosed in, for instance, Patent Literatures 1 to 6. Patent Literature 1 discloses a compound containing a carbazole skeleton and a benzimidazole ring in the same molecule, and data of the compound as a blue fluorescent material host. Patent Literature 2 discloses a compound containing a carbazole skeleton and a 1,2,4-triazole ring in the same molecule, and data of the compound as a blue to blue-green fluorescent material host. Patent Literature 3 discloses a compound containing a carbazole skeleton and an imidazopyridine ring in the same molecule, and data of the compound as a blue fluorescent material host. Patent Literature 4 discloses a compound containing a carbazole skeleton, a fluorene skeleton and an imidazopyridine ring (a nitrogen-containing aromatic ring) in the same molecule, and data of the compound as a blue fluorescent material host. Patent Literature 5 discloses a compound containing a carbazole skeleton and a nitrogen-containing aromatic ring in the same molecule, and data of the compound as a host material used together with a blue to blue-green phosphorescent material. Patent Literature 6 discloses a compound containing a carbazole skeleton, a fluorene skeleton and a phenanthroline ring (a nitrogen-containing aromatic ring) in the same molecule, and data of the compound as a green phosphorescent material host.

Patent Literatures 7 and 8 disclose compounds having the same skeletons as those of the compounds Patent Literatures 1 to 6. Patent Literature 7 discloses a compound containing a carbazole skeleton and a pyridine ring in the same molecule, and data of the compound serving as a hole transporting material. Patent Literature 8 discloses a compound containing a fluorene skeleton and a pyridine ring (a nitrogen-containing aromatic ring) in the same molecule, and application of the compound to the emitting layer.

CITATION LIST

Patent Literatures

Patent Literature 1 JP-A-2001-247858
Patent Literature 2 JP-A-2000-68059
Patent Literature 3 JP-A-2001-192653
Patent Literature 4 US2004-157084
Patent Literature 5 WO2003/080760
Patent Literature 6 WO2004/026870
Patent Literature 7 JP-A-2000-169448
Patent Literature 8 JP-A-2007-261969

SUMMARY OF THE INVENTION

Problems to be Solved by the Invention

Although Patent Literatures 1 to 4 disclose data on when the compounds therein serve as a fluorescent material host, Patent Literatures 1 to 4 fail to disclose whether or not the compounds serve as a green phosphorescent material host. In Patent Literature 5 and 6, in which the compounds serving as a phosphorescent material host are disclosed, organic EL devices using the compounds do not exhibit a sufficient luminous efficiency and driving voltage for the organic EL devices is not satisfactory. Patent Literatures 7 and 8 do not disclose whether or not the compounds therein serve as a phosphorescent material host.

Typically, a phosphorescent organic EL device emits light using excited triplet energy. As compared with a typical fluorescent organic EL device, a difference in electron affinity between the emitting layer and the electron transporting layer and a difference in ionization potential between the hole transporting layer and the emitting layer become large, so that carrier injection is blocked to often require high voltage.

An object of the invention is to provide a long-life organic EL device that exhibits a high luminous efficiency and is capable of being driven at low voltage required for power consumption saving and to provide a fluorene-containing aromatic compound usable for an organic-EL-device material providing such an organic EL device.

Means for Solving the Problems

After conducting concentrated studies in order to achieve such an object, the inventors have found that a difference in electron affinity between the electron transporting layer and the emitting layer can be reduced by using a material in which a carbazole skeleton and a nitrogen-containing hetero aromatic ring are combined, and that introduction of a fluorene skeleton in the same molecule improves transporting performance of carrier (particularly, electrons) and significantly lowers voltage applied to a phosphorescent organic EL device. In other words, an aromatic compound having a carbazole skeleton represented by a formula (1) below, a nitrogen-containing hetero aromatic ring and a fluorene skeleton in the same molecule can be provided. Also, an organic EL device that can be driven at low voltage required for power consumption saving can be provided by using the aromatic compound as an organic-EL-device material.

Specifically, a fluorene-containing aromatic compound represented by the formula (1) according to an aspect of the invention includes a carbazole skeleton, a nitrogen-containing hetero aromatic ring and a fluorene skeleton in the same molecule.

[Chemical Formula 1]

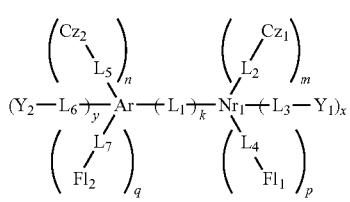

(1)

In the formula: $Nr_1$ represents a substituted or unsubstituted monocyclic nitrogen-containing aromatic ring having 2 to 5 carbon atoms for forming the aromatic ring (hereinafter referred to as ring carbon atoms), or a bicyclic nitrogen-containing aromatic ring having 2 to 9 ring carbon atoms; Ar represents a single bond, a substituted or unsubstituted aromatic ring having 5 to 40 ring carbon atoms; $Fl_1$ and $Fl_2$ each independently represent a substituted or unsubstituted fluorenyl group; p is an integer of 0 to 3 representing the number of a substituent(s) of $-(L_4-Fl_1)$ directly bonding to $Nr_1$; when p is 2 or more, $L_4$ may be the same or different and $Fl_1$ may be the same or different; q is an integer of 0 to 3 representing the number of a substituent of $-(L_7-Fl_2)$ directly bonding to Ar; when q is 2 or more, $L_7$ may be the same or different and $Fl_2$ may be the same or different; p+q=1 or more; $Cz_1$ and $Cz_2$ each independently represent a substituted or unsubstituted carbazolyl group; m is an integer of 0 to 3 representing the number of a substituent of $-(L_2-Cz_1)$ directly bonding to $Nr_1$; when m is 2 or more, $L_2$ may be the same or different and $Cz_1$ may be the same or different; n is an integer of 0 to 3 representing the number of a substituent of $-(L_5-Cz_2)$ directly bonding to Ar; when n is 2 or more, $L_5$ may be the same or different and $Cz_2$ may be the same or different; m+n=1 or more; $Y^1$ and $Y^2$ each independently represent a hydrogen atom, a deuterium atom, a fluorine atom, a chlorine atom, a bromine atom, a iodine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms; x is an integer of 1 to 3 representing the number of a substituent of $-(L_3-Y_1)$ directly bonding to $Nr_1$; when x is 2 or more, $L_3$ may be the same or different and $Y_1$ may be the same or different; y is an integer of 1 to 3 representing the number of a substituent of $-(L_6-Y_2)$ directly bonding to Ar; when y is 2 or more, $L_6$ may be the same or different and $Y_2$ may be the same or different; m+p+x is less than or equal to a numeral represented by (the number of the possible substituent(s) for selected $Nr_1$ minus 1); n+q+y is less than or equal to a numeral represented by (the number of the possible substituent(s) for selected Ar minus 1); and $L_1$ to $L_7$ each independently represent a single bond, a substituted or unsubstituted aromatic ring having 6 to 30 ring carbon atoms, or a substituted or unsubstituted aromatic heterocyclic ring having 2 to 30 ring carbon atoms; and k represents an integer of 1 to 3, in which a compound represented by a formula (2) below is omitted from the fluorene-containing aromatic compound represented by the formula (1).

[Chemical Formula 2]

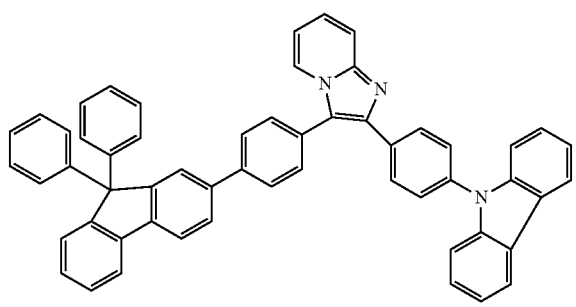

(2)

In the fluorene-containing aromatic compound according to the above aspect of the invention, in the formula (1), $Nr_1$ is preferably a nitrogen-containing aromatic ring selected from a substituted or unsubstituted pyrrole ring, pyrazole ring, imidazole ring, triazole ring, pyridine ring, pyrimidine ring, pyridazine ring, pyrazine ring, triazine ring, indole ring, indazole ring, benzimidazole ring, quinoline ring, isoquinoline ring, cinnoline ring, quinoxaline ring and imidazopyridine ring.

Moreover, according to the above aspect of the invention, it is preferable that each of $Cz_1$ and $Cz_2$ in the formula (1) is independently represented by the following formula (3) or (4).

[Chemical Formula 3]

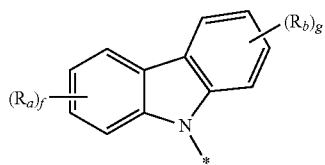

(3)

In the formula (3), Ra and Rb each independently represent a hydrogen atom, a deuterium atom, a fluorine atom, a chlorine atom, a bromine atom, a iodine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms; and f and g each independently represent an integer of 1 to 4.

[Chemical Formula 4]

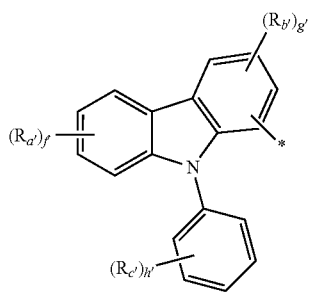

(4)

In the formula (4), Ra', Rb' and Rc' each independently represent a hydrogen atom, a deuterium atom, a fluorine atom, a chlorine atom, a bromine atom, a iodine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms; f is an integer of 1 to 4; g' is an integer of 1 to 3; and h' is an inter of 1 to 5.

According to the above aspect of the invention, in the formula (1), it is preferable that k is 1 and m+n+p+q is less than or equal to 6.

Moreover, it is preferable that each of $Y_1$ and $Y_2$ is independently represented by a hydrogen atom or a phenyl group.

According to the above aspect of the invention, it is preferable that k is 1; $L_1$, $L_2$, $L_3$, $L_5$ and $L_6$ each independently represent a single bond, a substituted or unsubstituted phenylene group, a substituted or unsubstituted biphenylene group, a substituted or unsubstituted terphenylene group, or a substituted or unsubstituted fluorenylene group; and $L_4$ and $L_7$ each independently represent a single bond, a substituted or unsubstituted phenylene group, a substituted or unsubstituted biphenylene group, or a substituted or unsubstituted terphenylene group. When a hydrogen atom is bonded to the above groups, the hydrogen atom may be a deuterium atom.

It is preferable that m+n=1 or 2 and p+q=1 to 2.

Ar is preferably a monocyclic aromatic ring selected from a substituted or unsubstituted benzene ring, pyrazole ring, imidazole ring, triazole ring, pyridine ring, pyrimidine ring, pyridazine ring, pyrazine ring, triazine ring or thiophene ring, particularly preferably a benzene ring.

According to the above aspect of the invention, it is preferable that each of $Fl_1$ and $Fl_2$ in the formula (1) is independently represented by a formula (5) below.

[Chemical Formula 5]

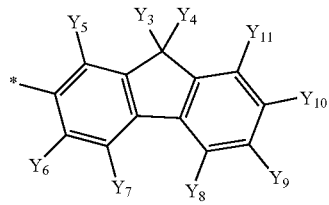

(5)

In the formula (5): $Y_3$ and $Y_4$ each independently represent: a hydrogen atom; a deuterium atom; a linear, branched or cyclic alkyl group having 1 to 10 carbon atoms; a linear, branched or cyclic haloalkyl group having 1 to 10 carbon atoms; a linear, branched or cyclic alkylsilyl group having 1 to 10 carbon atoms; a substituted or unsubstituted arylsilyl group having 6 to 30 carbon atoms; a substituted or unsubstituted aryl group having 6 to 30 ring carbon atoms; or a substituted or unsubstituted heteroaryl group having 2 to 10 ring carbon atoms; and $Y_5$, $Y_6$, $Y_7$, $Y_8$, $Y_9$, $Y_{10}$ and $Y_{11}$ each independently represent: a hydrogen atom; a deuterium atom; a fluorine atom; a chlorine atom; a bromine atom; an iodine atom; a cyano group; a linear, branched or cyclic alkyl group having 1 to 10 carbon atoms; a linear, branched or cyclic alkoxy group having 1 to 10 carbon atoms; a linear, branched or cyclic haloalkyl group having 1 to 10 carbon atoms; a linear, branched or cyclic haloalkoxy group having 1 to 10 carbon atoms; a linear, branched or cyclic alkylsilyl group having 1 to 10 carbon atoms; a substituted or unsubstituted arylsilyl group having 6 to 30 carbon atoms; a substituted or unsubstituted aryl group having 6 to 30 ring carbon atoms; or a substituted or unsubstituted heteroaryl group having 2 to 10 ring carbon atoms.

According to the above aspect of the invention, each of $Y_3$ and $Y_4$ is independently a linear alkyl group having 1 to 10 carbon atoms or a phenyl group in the formula (5).

It is more preferable that both of $Y_3$ and $Y_4$ are a methyl group.

According to the above aspect of the invention, it is preferable that each of $Cz_1$ and $Cz_2$ in the formula (1) is independently represented by a formula (3) or a formula (4).

[Chemical Formula 6]

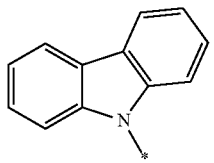

(3a)

[Chemical Formula 7]

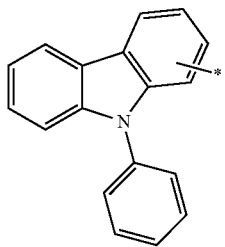

(4a)

According to the aspect of the invention, it is more preferable that $Nr_1$ is a pyrimidine ring in the formula (1).

It is preferable that the fluorene-containing aromatic compound is used as an organic-electroluminescence-device material.

An organic electroluminescence device according to another aspect of the invention includes: a cathode; an anode; and an organic thin-film layer provided between the cathode and the anode, the organic thin-film layer formed out of one or more layers including an emitting layer, in which at least one layer of the organic thin-film layer contains the fluorene-containing aromatic compound.

In the organic electroluminescence device according to the above aspect of the invention, the emitting layer preferably contains the as a host material.

It is preferable that the organic electroluminescence device further contains a phosphorescent material.

It is more preferable that the emitting layer includes a host material and a phosphorescent material, in which the phosphorescent material is an ortho metalation of a complex of a metal atom selected from iridium (Ir), osmium (Os) and platinum (Pt).

In the organic electroluminescence device according to the above aspect of the invention, it is preferable that the organic thin-film layer includes an electron injecting layer provided between the cathode and the emitting layer, the electron injecting layer containing a nitrogen-containing cyclic derivative.

Moreover, it is preferable that the organic thin-film layer includes an electron transporting layer provided between the cathode and the emitting layer, the electron transporting layer containing the fluorene-containing aromatic compound.

In the organic EL device according to the above aspect of the invention, a reduction-causing dopant is preferably added in an interfacial region between the cathode and the organic thin-film layer.

Effects of the Invention

According to the aspect(s) of the invention, a fluorene-containing compound represented by the formula (1) is used as an organic-EL-device material to provide an organic EL device with a high luminous efficiency, a long lifetime and low voltage drivability. Moreover, the organic-EL-device material is effective as an organic-electron-device material for an organic solar cell, an organic semiconductor laser, a sensor using an organic substance and an organic TFT.

BRIEF DESCRIPTION OF DRAWING

FIG. 1 schematically shows an exemplary structure of an organic electroluminescence device according to an exemplary embodiment of the invention.

DESCRIPTION OF EMBODIMENT

Description will be made below on an exemplary embodiment(s) of the invention. A fluorene-containing aromatic compound according to this exemplary embodiment of the invention is suitably used especially as an organic-EL-device material. The fluorene-containing aromatic compound is used in an organic EL device according to this exemplary embodiment of the invention Structure of Organic EL Device Firstly, structure(s) of an organic EL device will be described below.

The following are representative structure examples of an organic EL device:
(1) anode/emitting layer/cathode;
(2) anode/hole injecting layer/emitting layer/cathode;
(3) anode/emitting layer/electron injecting•transporting layer/cathode;
(4) anode/hole injecting layer/emitting layer/electron injecting•transporting layer/cathode;
(5) anode/organic semiconductor layer/emitting layer/cathode;
(6) anode/organic semiconductor layer/electron blocking layer/emitting layer/cathode;
(7) anode/organic semiconductor layer/emitting layer/adhesion improving layer/cathode;
(8) anode/hole injecting•transporting layer/emitting layer/electron injecting•transporting layer/cathode;
(9) anode/insulating layer/emitting layer/insulating layer/cathode;
(10) anode/inorganic semiconductor layer/insulating layer/emitting layer/insulating layer/cathode;
(11) anode/organic semiconductor layer/insulating layer/emitting layer/insulating layer/cathode;
(12) anode/insulating layer/hole injecting•transporting layer/emitting layer/insulating layer/cathode; and
(13) anode/insulating layer/hole injecting•transporting layer/emitting layer/electron injecting•transporting layer/cathode.

The structure (8) is suitably used among the above, but the structure of the invention is not limited to the above structures.

FIG. 1 schematically shows an exemplary structure of an organic EL device according to an exemplary embodiment of the invention.

The organic EL device 1 includes a transparent substrate 2, an anode 3, a cathode 4 and an organic thin-film layer 10 positioned between the anode 3 and the cathode 4.

The organic thin-film layer 10 includes a phosphorescent-emitting layer 5 containing a phosphorescent host as a host material and a phosphorescent dopant as a phosphorescent material. A layer such as a hole injecting/transporting layer 6 may be provided between the phosphorescent-emitting layer 5 and the anode 3 while a layer such as an electron injecting/transporting layer 7 may be provided between the phosphorescent-emitting layer 5 and the cathode 4.

In addition, an electron blocking layer may be provided to the phosphorescent-emitting layer 5 adjacent to the anode 3 while a hole blocking layer may be provided to the phosphorescent-emitting layer 5 adjacent to the cathode 4.

With this structure, electrons and holes can be trapped in the phosphorescent-emitting layer 5, thereby enhancing probability of exciton generation in the phosphorescent-emitting layer 5.

It should be noted that a "fluorescent host" and a "phosphorescent host" herein respectively mean a fluorescent host combined with a fluorescent dopant and a phosphorescent host combined with a phosphorescent dopant, and that a distinction between the fluorescent host and phosphorescent host is not unambiguously derived only from a molecular structure of the host in a limited manner.

In other words, the fluorescent host herein means a material for forming a fluorescent-emitting layer containing a fluorescent dopant, and does not mean a host that is only usable as a host of a fluorescent material.

Likewise, the phosphorescent host herein means a material for forming a phosphorescent-emitting layer containing a phosphorescent dopant, and does not mean a host that is only usable as a host of a phosphorescent material.

It should be noted that the "hole injecting/transporting layer" herein means "at least either one of a hole injecting layer and a hole transporting layer" while the "electron injecting/transporting layer" herein means "at least either one of an electron injecting layer and an electron transporting layer."

Transparent Substrate

The organic EL device according to this exemplary embodiment of the invention is formed on a light-transmissive substrate. The light-transmissive plate, which supports the organic EL device, is preferably a smooth substrate that transmits 50% or more of light in a visible region of 400 nm to 700 nm.

The light-transmissive plate is exemplarily a glass plate, a polymer plate or the like.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used.

Anode and Cathode

The anode of the organic EL device is used for injecting holes into the hole injecting layer, the hole transporting layer or the emitting layer. It is effective that the anode has a work function of 4.5 eV or more.

Exemplary materials for the anode are alloys of indium-tin oxide (ITO), tin oxide (NESA), indium zinc oxide, gold, silver, platinum and copper.

The anode may be made by forming a thin film from the above electrode materials through methods such as vapor deposition and sputtering.

When light from the emitting layer is to be emitted through the anode as in this embodiment, the anode preferably transmits more than 10% of the light in the visible region. Sheet resistance of the anode is preferably several hundreds $\Omega$/square or lower. Although depending on the material of the anode, the thickness of the anode is typically in a range of 10 nm to 1 µm, and preferably in a range of 10 nm to 200 nm.

The cathode is preferably formed of a material with smaller work function in order to inject electrons into the electron injecting layer, the electron transporting layer and the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode, the cathode may be made by forming a thin film from the above materials through a method such as vapor deposition or sputtering. In addition, the light may be emitted through the cathode.

Emitting Layer

The emitting layer of the organic EL device has functions as follows.

Specifically:
(1) injecting function: a function for accepting, when an electrical field is applied, the holes injected by the anode or the hole injecting layer, or the electrons injected by the cathode or the electron injecting layer;
(2) transporting function: a function for transporting injected electric charges (the electrons and the holes) by the force of the electrical field; and
(3) emitting function: a function for providing a condition for recombination of the electrons and the holes to emit light.

Injectability of the holes may differ from that of the electrons and transporting capabilities of the hole and the electrons (represented by mobilities of the holes and the electrons) may differ from each other.

As a method of forming the emitting layer, known methods such as vapor deposition, spin coating and an LB method may be employed.

The emitting layer is preferably a molecular deposit film.

The molecular deposit film means a thin film formed by depositing a material compound in gas phase or a film formed by solidifying a material compound in a solution state or in liquid phase. The molecular deposit film is typically distinguished from a thin film formed by the LB method (molecular accumulation film) by differences in aggregation structures, higher order structures and functional differences arising therefrom.

As disclosed in JP-A-57-51781, the emitting layer can be formed from a thin film formed by spin coating or the like, the thin film being formed from a solution prepared by dissolving a binder (e.g. a resin) and a material compound in a solvent.

The thickness of the emitting layer is preferably in a range of 5 nm to 50 nm, more preferably in a range of 7 nm to 50 nm and most preferably in a range of 10 nm to 50 nm. The thickness less than 5 nm may cause difficulty in forming the emitting layer and in controlling chromaticity, while the thickness more than 50 nm may increase driving voltage.

The organic EL device according to this exemplary embodiment includes: a cathode; an anode; and a single or a plurality of organic thin-film layers provided between the cathode and the anode, in which the organic thin-film layer(s) includes at least one emitting layer, and the organic thin-film layer(s) includes at least one phosphorescent material and at least one organic-EL-device material according to another aspect of the invention (later described). In addition, at least one of the emitting layer(s) preferably contains the organic-EL-device material of the exemplary embodiment and at least one phosphorescent material.

Organic-EL-Device Material

The organic-EL-device material according to this exemplary embodiment is represented by a formula (1) below.

[Chemical Formula 8]

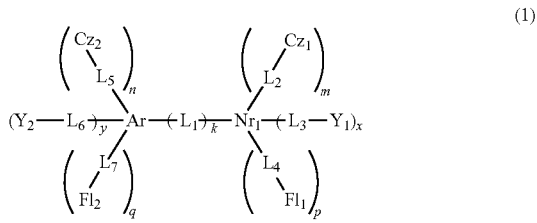

(1)

In the formula (1): $Nr_1$ represents a substituted or unsubstituted monocyclic nitrogen-containing aromatic ring having 2 to 5 ring carbon atoms, or a bicyclic nitrogen-containing aromatic ring having 2 to 9 ring carbon atoms; Ar represents a single bond, a substituted or unsubstituted aromatic ring having 5 to 40 ring carbon atoms; $Fl_1$ and $Fl_2$ each independently represent a substituted or unsubstituted fluorenyl group; p is an integer of 0 to 3 representing the number of a substituent of -($L_4$-$Fl_1$) directly bonding to $Nr_1$; when p is 2 or more, $L_4$ may be the same or different and $Fl_1$ may be the same or different; q is an integer of 0 to 3 representing the number of a substituent of -($L_7$-$Fl_2$) directly bonding to Ar; when q is 2 or more, $L_7$ may be the same or different and $Fl_2$ may be the same or different; p+q=1 or more; $Cz_1$ and $Cz_2$ each independently represent a substituted or unsubstituted carbazolyl group; m is an integer of 0 to 3 representing the number of a substituent of -($L_2$-$Cz_1$) directly bonding to $Nr_1$; when m is 2 or more, $L_2$ may be the same or different and $Cz_1$ may be the same or different; n is an integer of 0 to 3 representing the number of a substituent of -($L_5$-$Cz_2$) directly bonding to Ar; when n is 2 or more, $L_5$ may be the same or different and $Cz_2$ may be the same or different; m+n=1 or more; $Y^1$ and $Y^2$ each independently represent a hydrogen atom, a deuterium atom, a fluorine atom, a chlorine atom, a bromine atom, a iodine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms; x is an integer of 1 to 3 representing the number of a substituent of -($L_3$-$Y_1$) directly bonding to $Nr_1$; when x is 2 or more, $L_3$ may be the same or different and $Y_1$ may be the same or different; y is an integer of 1 to 3 representing the number of a substituent of -($L_6$-$Y_2$) directly bonding to Ar; when y is 2 or more, $L_6$ may be the same or different and $Y_2$ may be the same or different; m+p+x is less than or equal to a numeral represented by (the number of the possible substituent(s) for selected $Nr_1$ minus 1); n+q+y is less than or equal to a numeral represented by (the number of the possible substituent(s) for selected Ar minus 1); and $L_1$ to $L_7$ each independently represent a single bond, a substituted or unsubstituted aromatic ring having 6 to 30 ring carbon atoms, or a substituted or unsubstituted aromatic heterocyclic ring having 2 to 30 ring carbon atoms; and k represents an integer of 1 to 3, in which a compound represented by the following formula (2) is omitted from the organic-EL-device material represented by the formula (1).

[Chemical Formula 9]

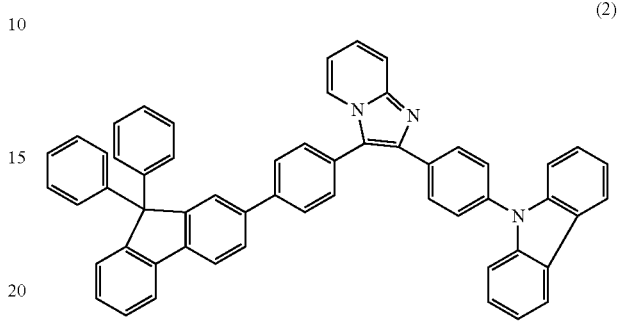

(2)

In the formula (1), $Nr_1$ is preferably a nitrogen-containing aromatic ring selected from a substituted or unsubstituted pyrrole ring, pyrazole ring, imidazole ring, triazole ring, pyridine ring, pyrimidine ring, pyridazine ring, pyrazine ring, triazine ring, indole ring, indazole ring, benzimidazole ring, quinoline ring, isoquinoline ring, cinnoline ring, quinoxaline ring and imidazopyridine ring. When a hydrogen atom is bonded to the nitrogen-containing aromatic ring, the hydrogen atom may be a deuterium atom.

$Nr_1$ is more preferably a substituted or unsubstituted pyridine ring, pyrimidine ring, or triazine ring, particularly preferably a substituted or unsubstituted pyrimidine ring. In the formula (1), when $Nr_1$ is an imidazopyridine ring, a case where both of $Y_3$ and $Y_4$ in $Fl_2$ are a phenyl group may be omitted.

Moreover, in the formula (1), when $Nr_1$ is an imidazopyridine ring, a case where $L_7$ is a single bond may be omitted.

In the formula (1), Ar is preferably a monocyclic aromatic ring such as a substituted or unsubstituted benzene ring having 2 to 6 ring carbon atoms, pyrazole ring, imidazole ring, triazole ring, pyridine ring, pyrimidine ring, pyridazine ring, pyrazine ring, triazine ring or thiophene ring, particularly preferably a benzene ring. When a hydrogen atom is bonded to the monocyclic aromatic ring, the hydrogen atom may be a deuterium atom.

In addition, preferably, each of $Cz_1$ and $Cz_2$ in the formula (1) is independently represented by the following formula (3) or (4).

[Chemical Formula 10]

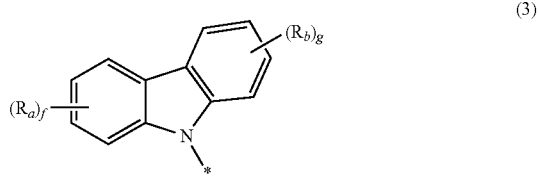

(3)

In the formula, Ra and Rb each independently represent a hydrogen atom, a deuterium atom, a fluorine atom, a chlorine atom, a bromine atom, a iodine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms; and f and g each independently represent an integer of 1 to 4.

[Chemical Formula 11]

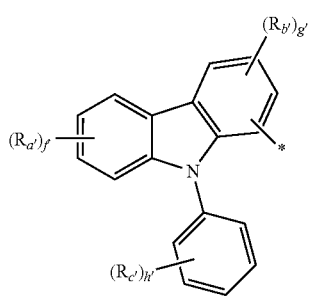

(4)

In the formula, Ra', Rb' and Rc' each independently represent a hydrogen atom, a deuterium atom, a fluorine atom, a chlorine atom, a bromine atom, a iodine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms; f' is an integer of 1 to 4; g' is an integer of 1 to 3; and h' is an inter of 1 to 5.

In addition, preferably, each of $Cz_1$ and $Cz_2$ is independently represented by the following formula (3a) or (4a).

[Chemical Formula 12]

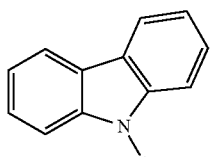

(3a)

[Chemical Formula 13]

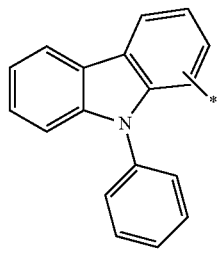

(4a)

In the formula (1), it is preferable that k is 1 and m+n+p+q is less than or equal to 6. More preferably, m+n=1 or 2 and p+q=1 or 2. m represents the number of a substituent(s) of -($L_2$-$Cz_1$) directly bonding to $Nr_1$. Likewise, n, p and q represent the number of a substituent(s).

In the formula (1), preferably, $Y_1$ and $Y_2$ each independently represent a hydrogen atom, a substituted or unsubstituted aryl group having 6 to 30 ring carbon atoms or a substituted or unsubstituted heteroaryl group having 2 to 10 ring carbon atoms, particularly preferably a hydrogen atom or a phenyl group.

In the formula (1), it is preferable that $L_1$, $L_2$, $L_3$, $L_5$ and $L_6$ each independently represent a single bond, a substituted or unsubstituted phenylene group, a substituted or unsubstituted biphenylene group, a substituted or unsubstituted terphenylene group, or a substituted or unsubstituted fluorenylene group; and $L_4$ and $L_7$ each independently represent a single bond, a substituted or unsubstituted phenylene group, a substituted or unsubstituted biphenylene group, or a substituted or unsubstituted terphenylene group. When a hydrogen atom is bonded to the above groups, the hydrogen atom may be a deuterium atom.

In the formula (1), preferably, each of $Fl_1$ and $Fl_2$ is independently represented by the following formula (5).

[Chemical Formula 14]

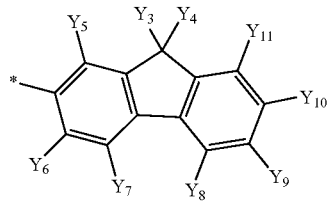

(5)

In the formula (5): $Y_3$ and $Y_4$ each independently represent: a hydrogen atom; a deuterium atom; a linear, branched or cyclic alkyl group having 1 to 10 carbon atoms; a linear, branched or cyclic haloalkyl group having 1 to 10 carbon atoms; a linear, branched or cyclic alkylsilyl group having 1 to 10 carbon atoms; a substituted or unsubstituted arylsilyl group having 6 to 30 carbon atoms; a substituted or unsubstituted aryl group having 6 to 30 ring carbon atoms; or a substituted or unsubstituted heteroaryl group having 2 to 10 ring carbon atoms; and $Y_5$, $Y_6$, $Y_7$, $Y_8$, $Y_9$, $Y_{10}$ and $Y_{11}$ each independently represent: a hydrogen atom; a deuterium atom; a fluorine atom; a chlorine atom; a bromine atom; an iodine atom; a cyano group; a linear, branched or cyclic alkyl group having 1 to 10 carbon atoms; a linear, branched or cyclic alkoxy group having 1 to 10 carbon atoms; a linear, branched or cyclic haloalkyl group having 1 to 10 carbon atoms; a linear, branched or cyclic haloalkoxy group having 1 to 10 carbon atoms; a linear, branched or cyclic alkylsilyl group having 1 to 10 carbon atoms; a substituted or unsubstituted arylsilyl group having 6 to 30 carbon atoms; a substituted or unsubstituted aryl group having 6 to 30 ring carbon atoms; or a substituted or unsubstituted heteroaryl group having 2 to 10 ring carbon atoms.

Further, in the formula (5), $Y_3$ and $Y_4$ each independently represent a linear, branched or cyclic alkyl group having 1 to 10 carbon atoms, a linear, branched or cyclic alkylsilyl group having 1 to 10 carbon atoms or a phenyl group. $Y_5, Y_6, Y_7, Y_8, Y_9, Y_{10}$ and $Y_{11}$ are preferably a hydrogen atom. More preferably, $Y_3$ and $Y_4$ each are independently a linear alkyl group having 1 to 10 carbon atoms or a phenyl group. Among the above, particularly preferably, $Y_3$ and $Y_4$ each are represented by a methyl group.

When $Nr_1, Ar, Y_1, Y_2, Fl_1, Fl_2, Cz_1, Cz_2$, and $L_1$ to $L_7$ in the formulae (1) and (3) to (5) each have one substituent or a plurality of substituents, the substituent(s) is preferably a linear, branched or cyclic alkyl group having 1 to 20 carbon atoms, a haloalkyl group having 1 to 20 carbon atoms, a linear, branched or cyclic alkylsilyl group having 1 to 10 carbon atoms, a cyano group, a halogen atom, or an aryl group having 6 to 22 ring carbon atoms.

Examples of the linear, branched or cyclic alkyl group having 1 to 20 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, cyclopentyl group, cyclohexyl group, cyclooctyl group and 3,5-dimethylcyclohexyl group.

Examples of the linear, branched or cyclic alkylsilyl group having 1 to 10 carbon atoms are a trimethylsilyl group, triethylsilyl group, tributylsilyl group, dimethylethylsilyl group, dimethylisopropylsilyl group, dimethylpropylsilyl group, dimethylbutylsilyl group, dimethyl-tertiary-butylsilyl group and diethylisopropylsilyl group.

Examples of the arylsilyl group having 6 to 30 carbon atoms are a phenyldimethylsilyl group, diphenylmethylsilyl group, diphenyl-tertiary-butylsilyl group and triphenylsilyl group.

Examples of the halogen atom are a fluorine atom, a chlorine atom, a bromine atom and an iodine atom.

Examples of the aryl group having 6 to 30 ring carbon atoms are a phenyl group, biphenyl group, terphenyl group, naphthyl group, fluoranthenyl group, triphenylenyl group and phenanthrenyl group.

Examples of the heteroaryl group having 2 to 10 ring carbon atoms are a pyrrolyl group, pyrazinyl group, pyridinyl group, indolyl group, isoindolyl group, furyl group, benzofuranyl group, isobenzofuranyl group, dibenzofuranyl group, dibenzothiophenyl group, quinolyl group, isoquinolyl group, quinoxalinyl group, carbazolyl group, phenanthridinyl group, acridinyl group, phenanthrolinyl group and thienyl group.

Examples of the aromatic ring having 6 to 30 ring carbon atoms are a benzene ring, naphthalene ring, phenanthrene ring, biphenyl ring, terphenyl ring and quarter-phenyl ring.

Examples of the aromatic heterocyclic group having 2 to 30 ring carbon atoms are a pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyrane ring and dibenzofuran ring.

Examples of the fluorene-containing aromatic compound according to this exemplary embodiment represented by the formula (1) are as follows.

[Chemical Formula 15]

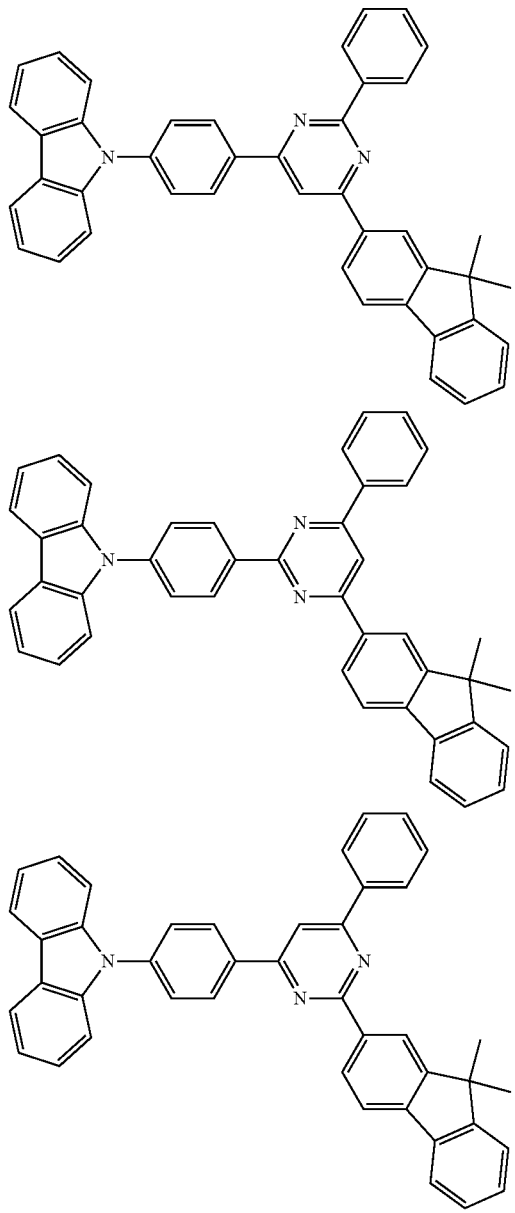

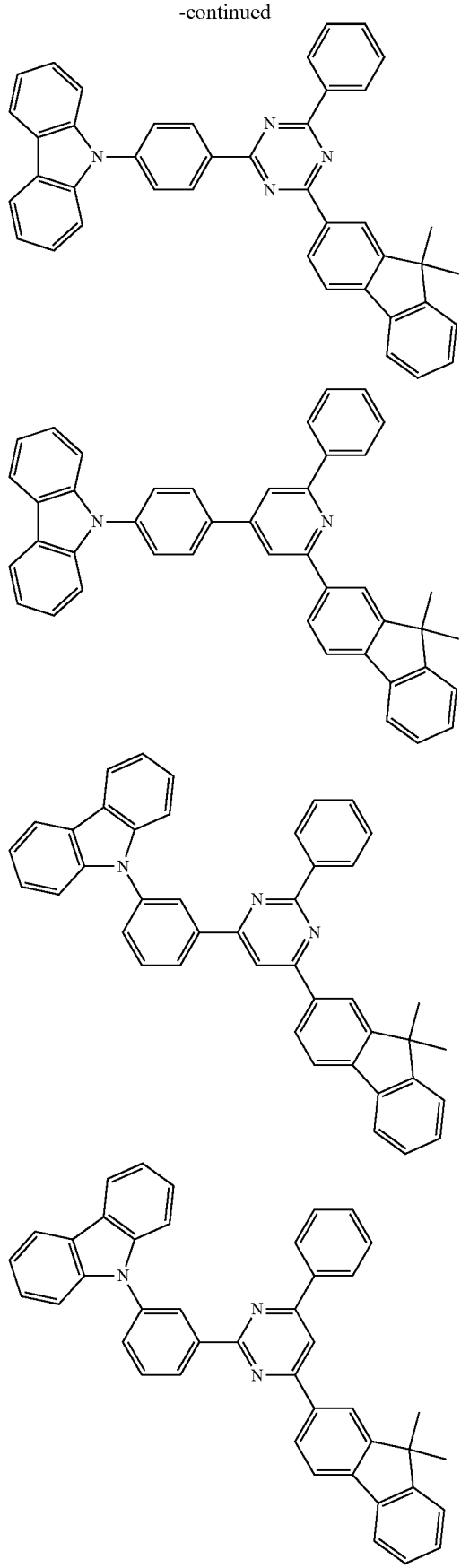
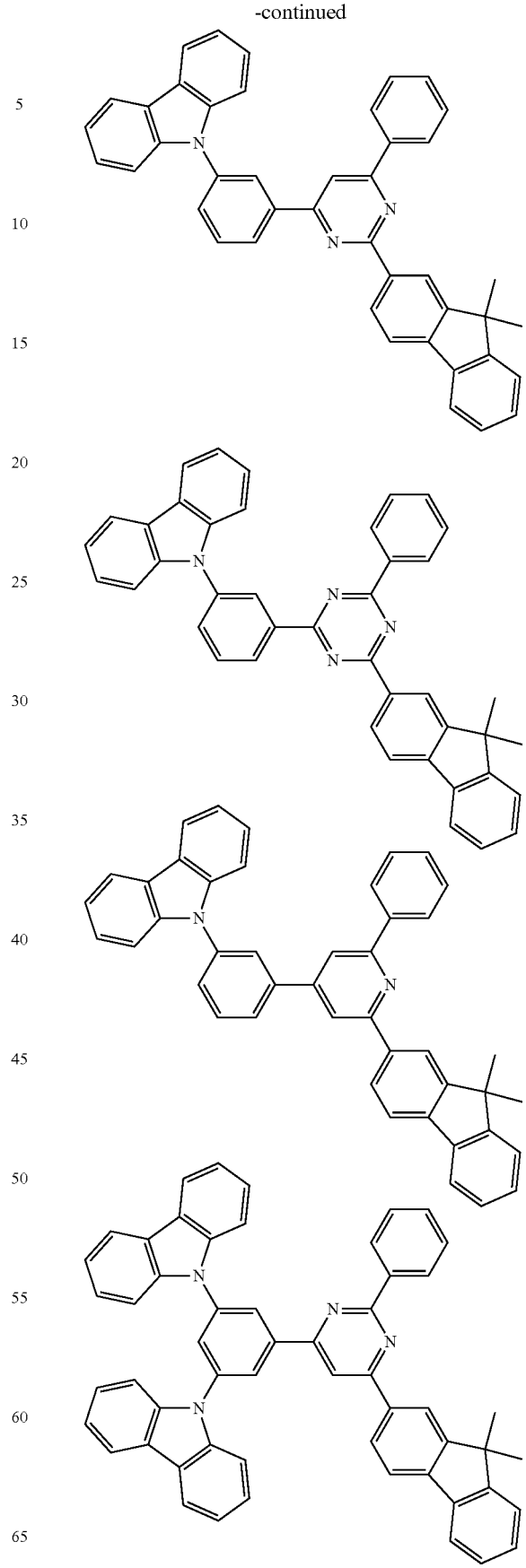

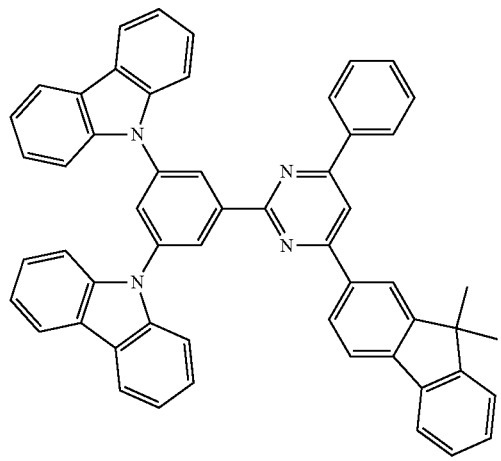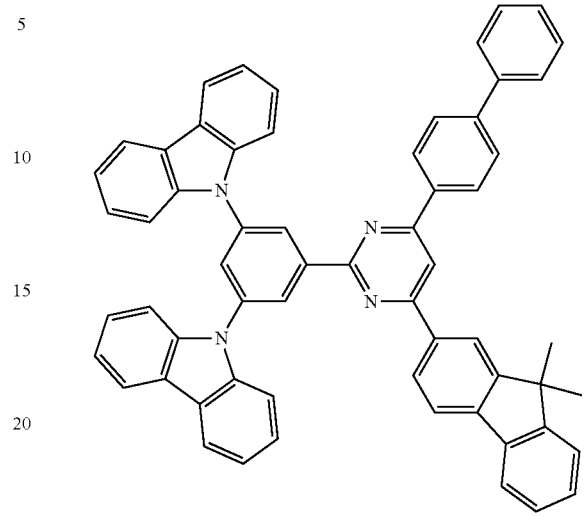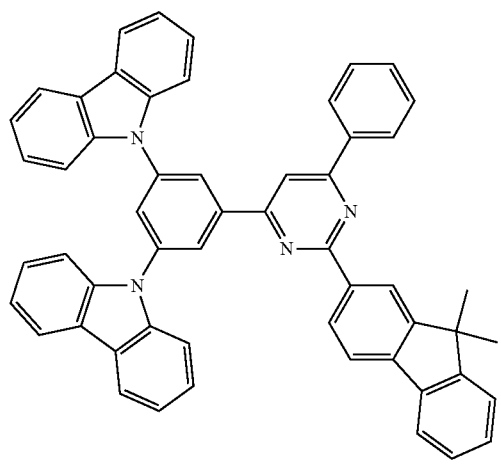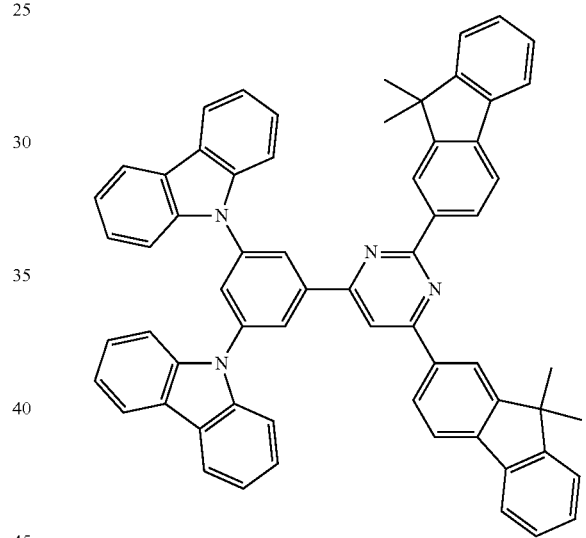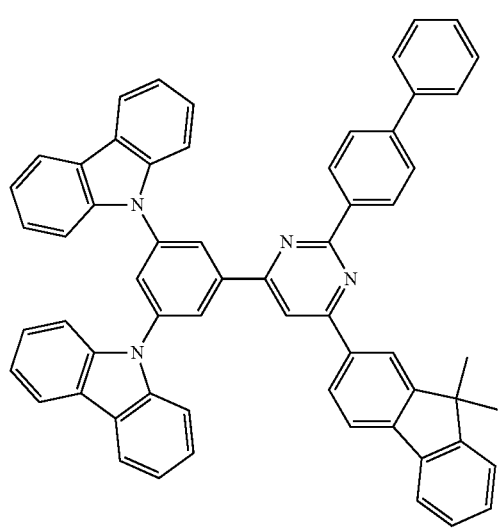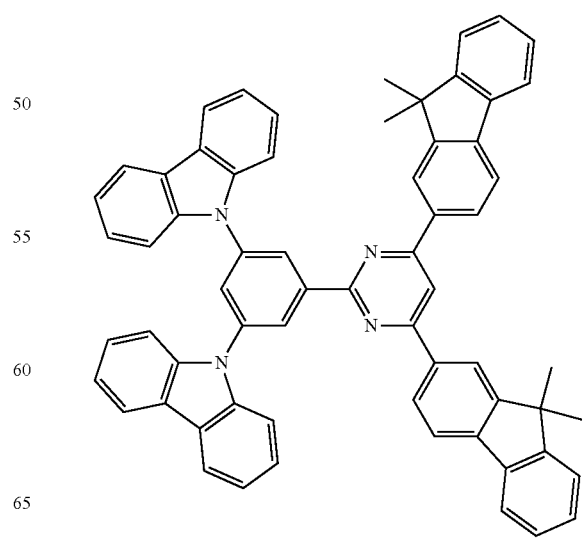

[Chemical Formula 16]
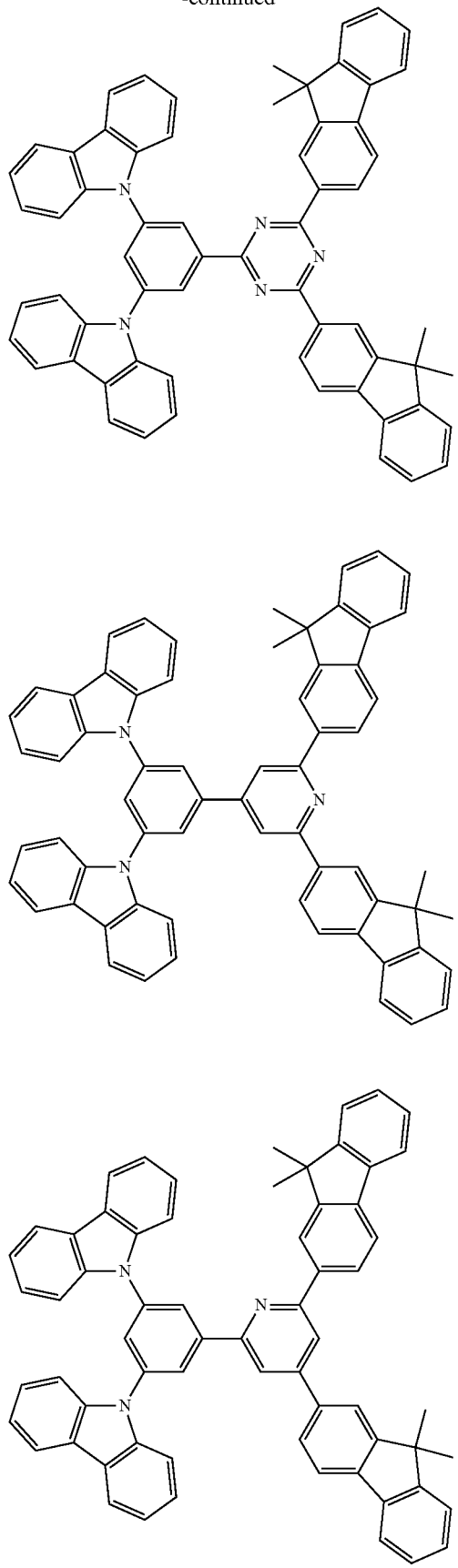
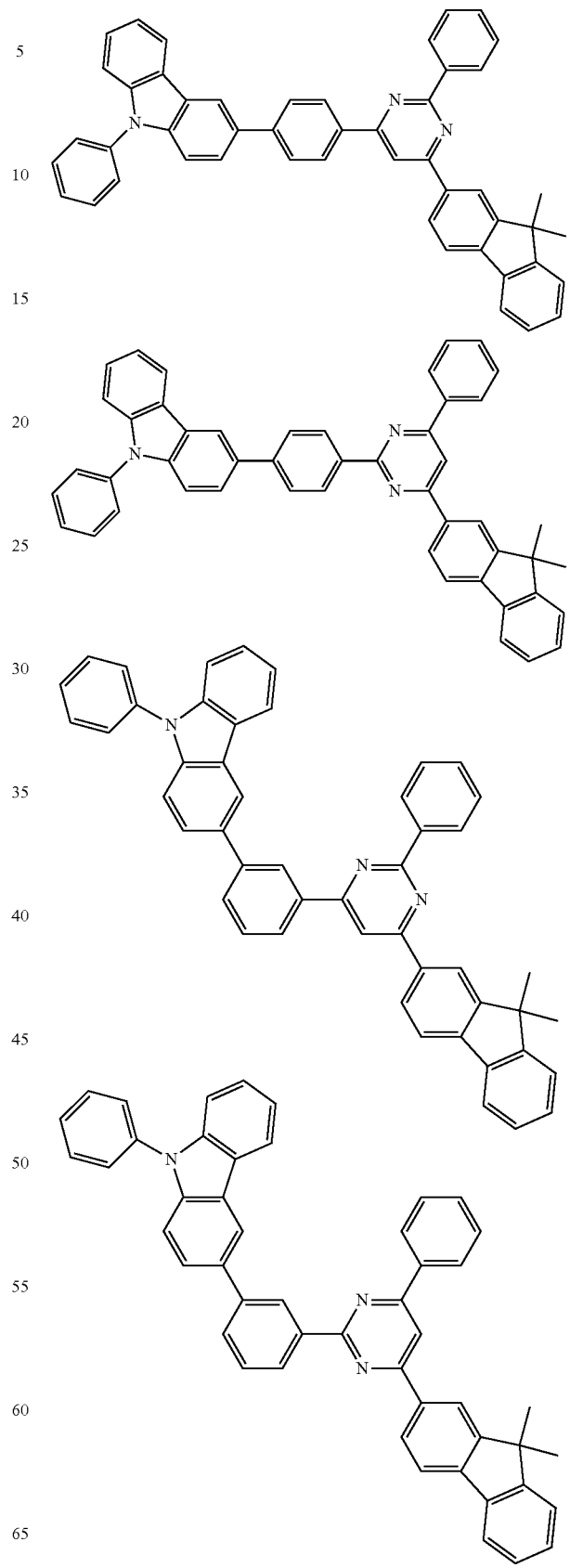

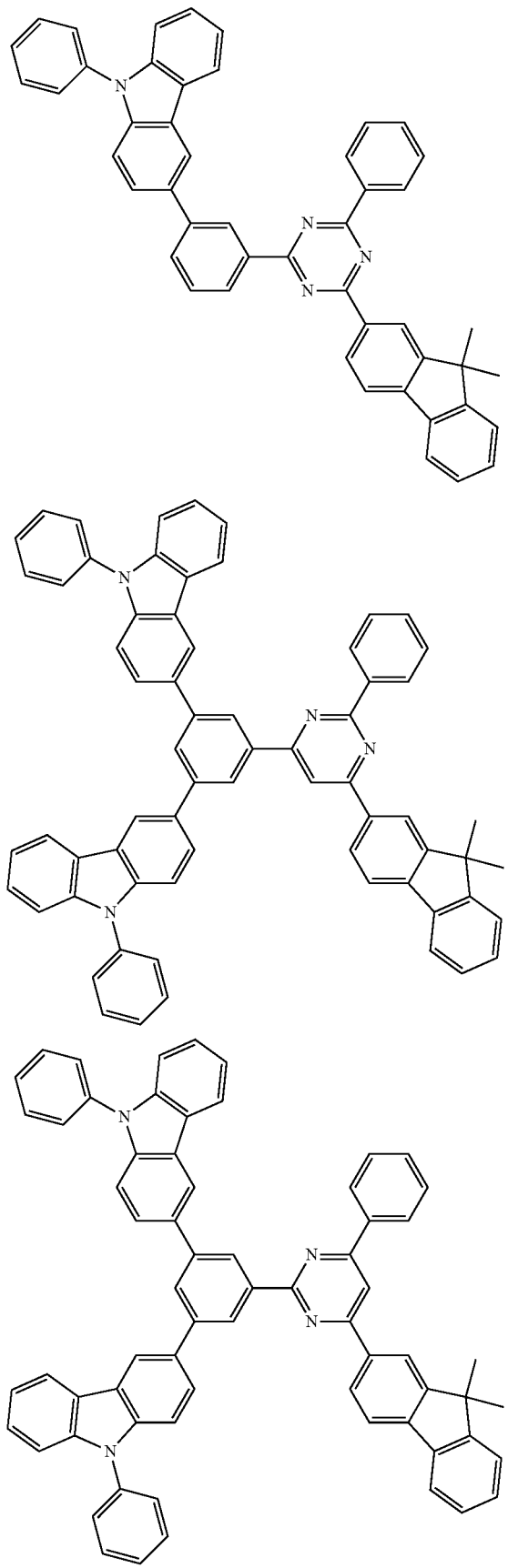
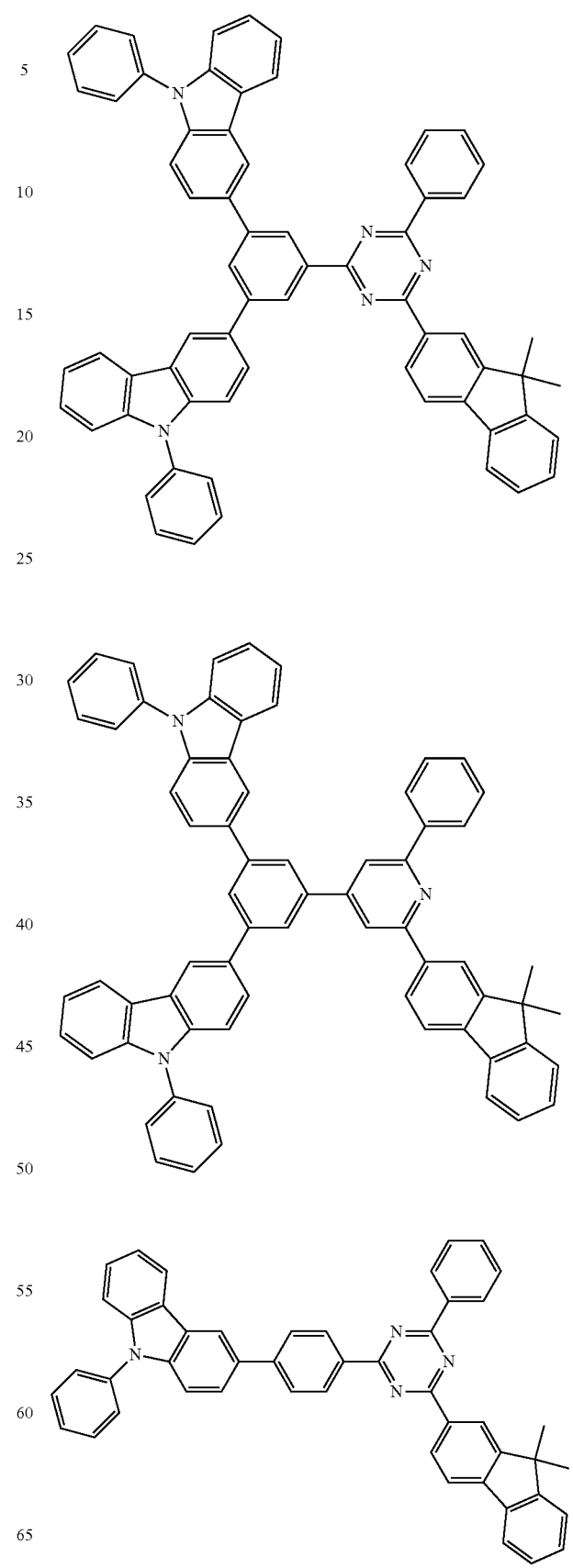

-continued
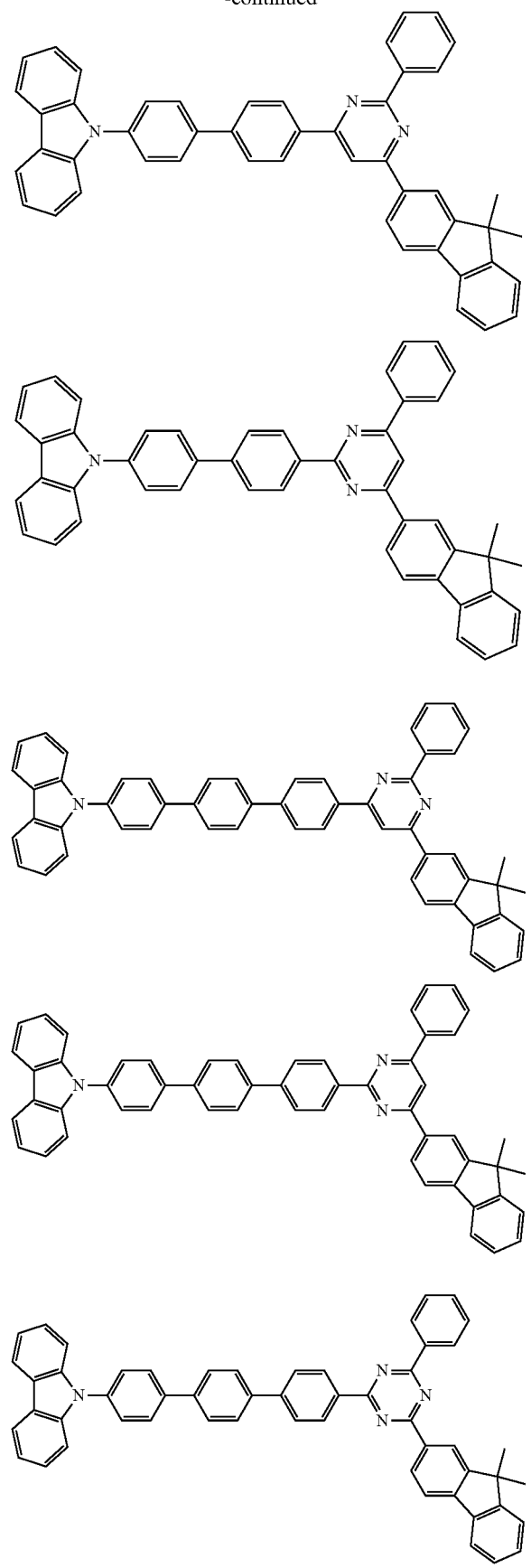
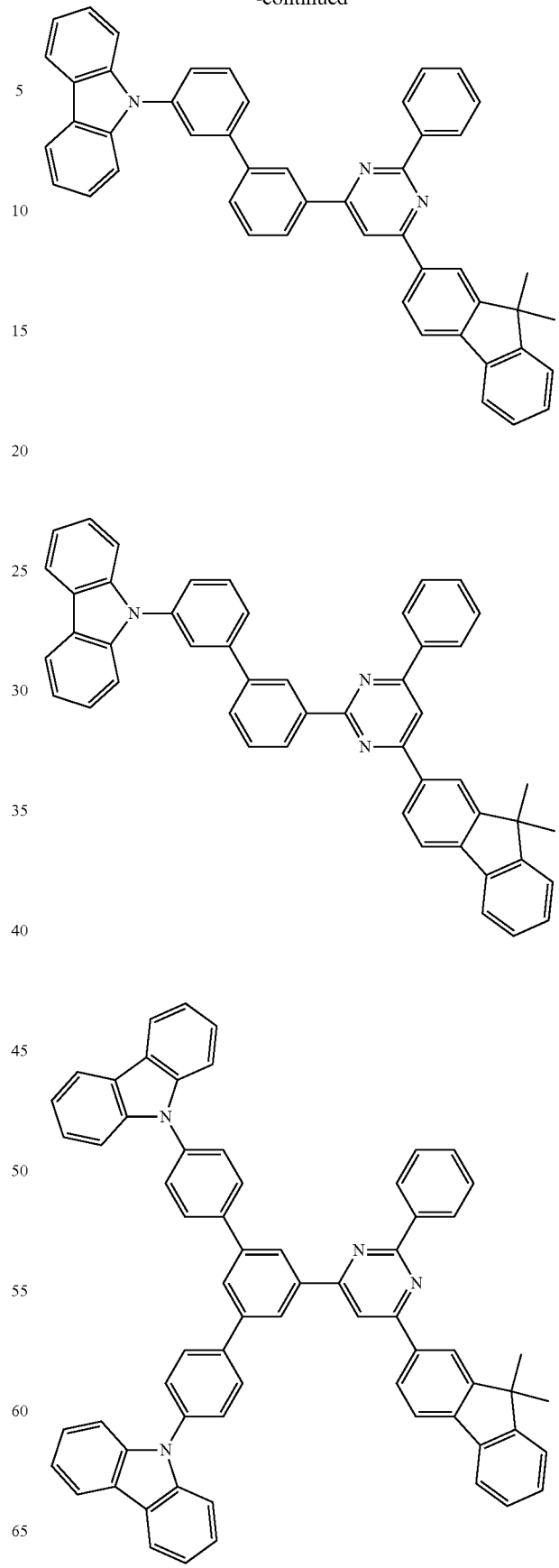

27
-continued
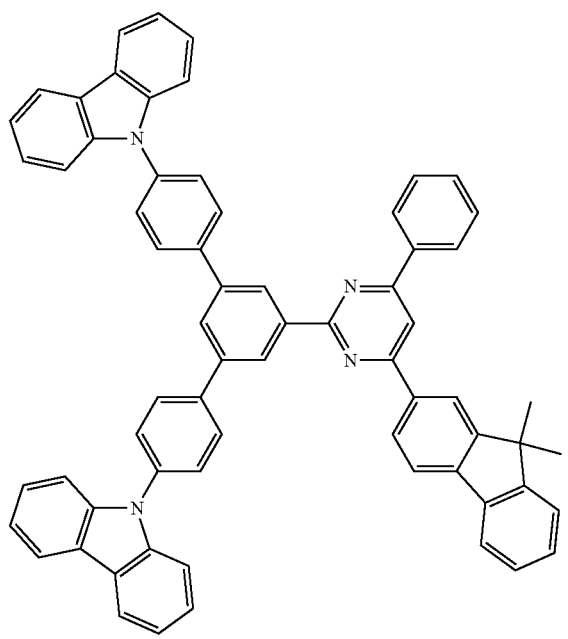
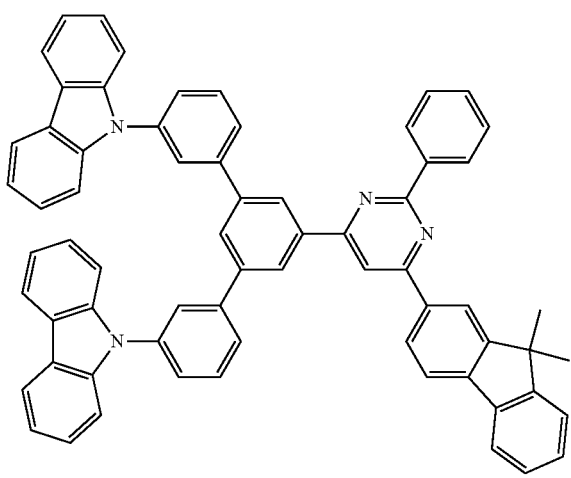
[Chemical Formula 17]
28
-continued
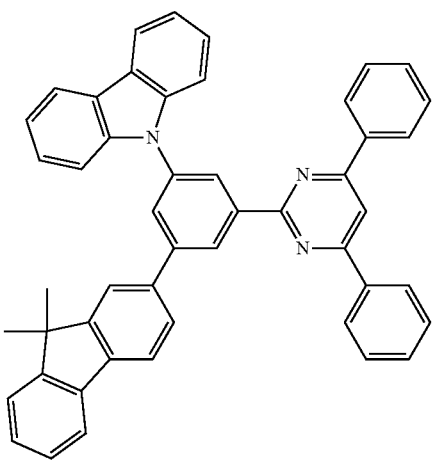
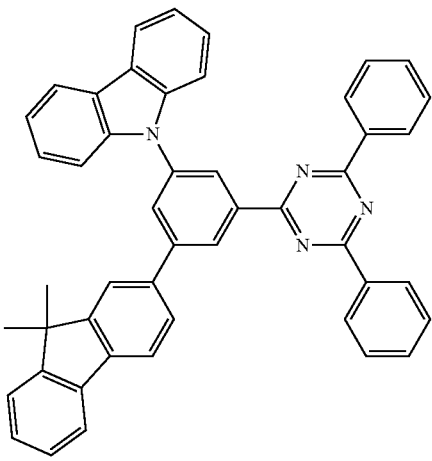
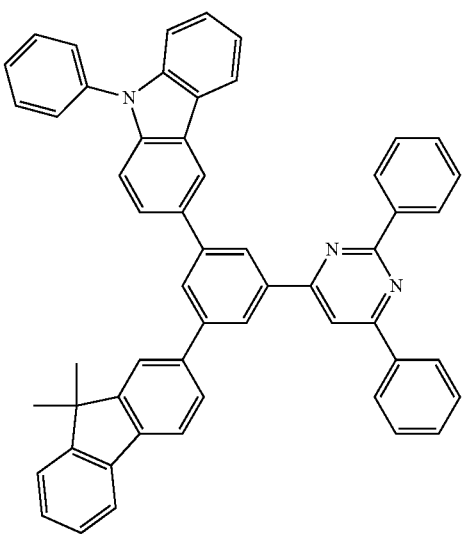

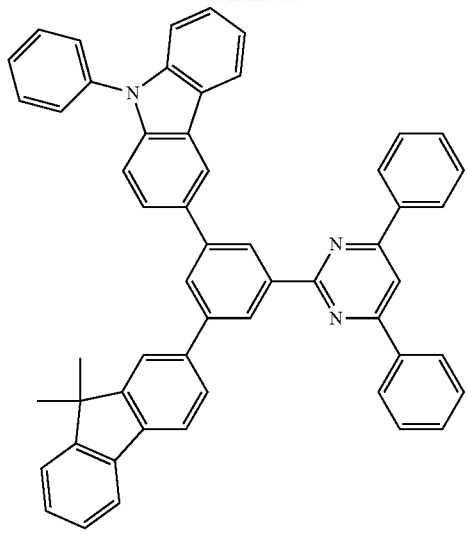
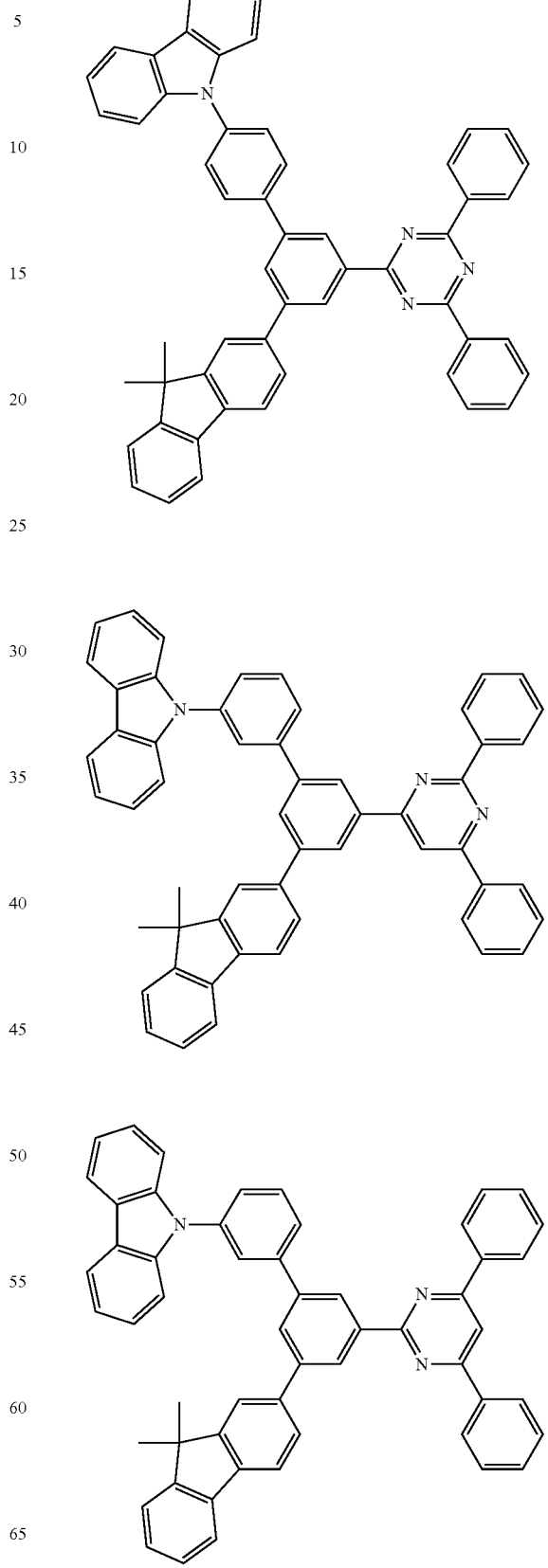

-continued
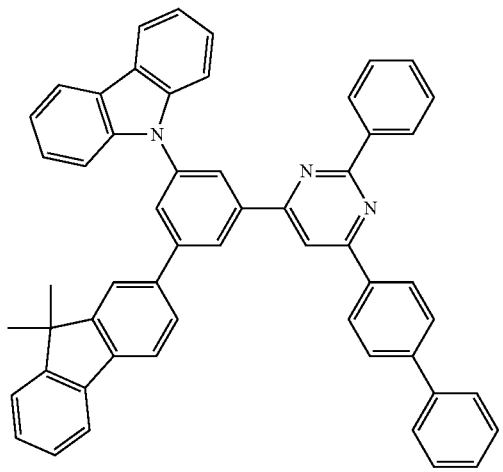
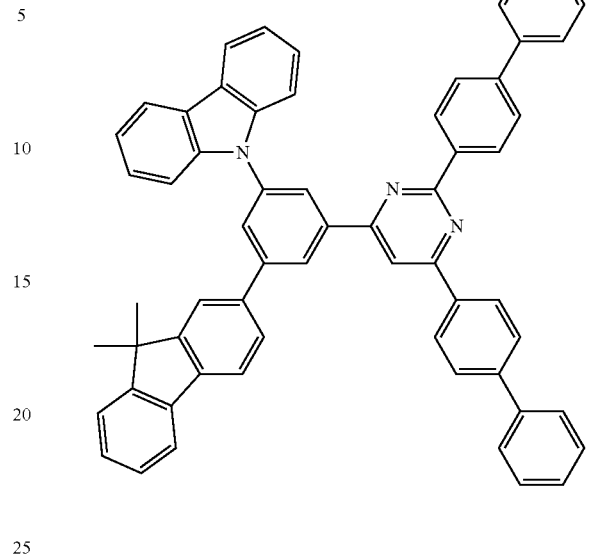
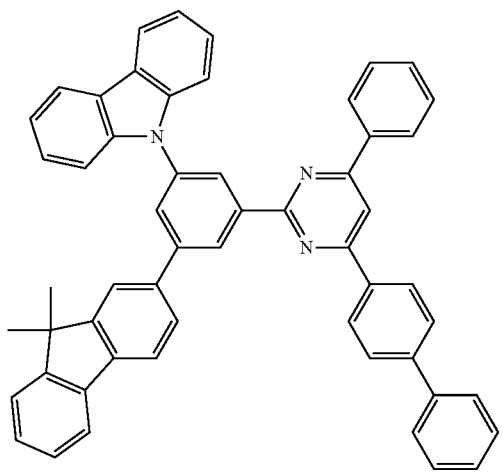
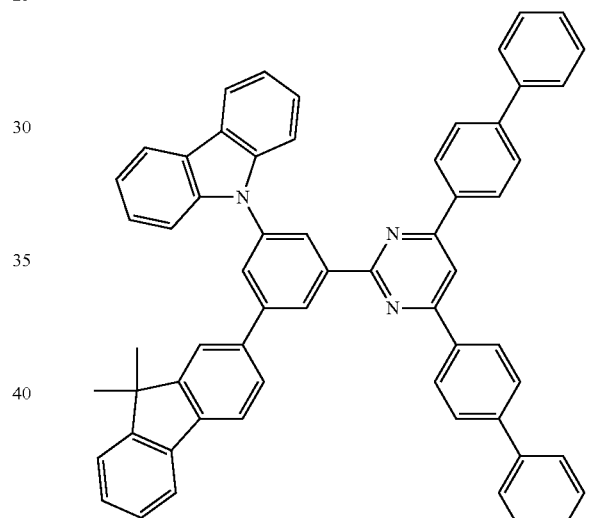
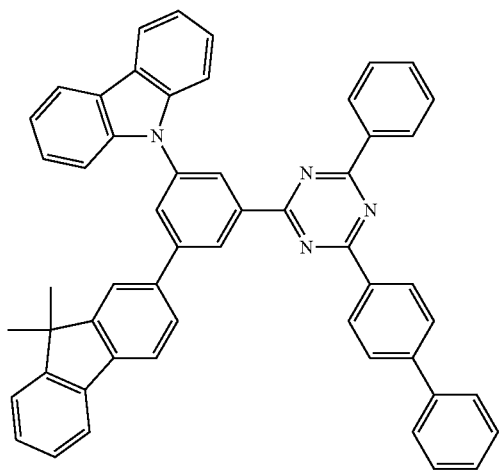
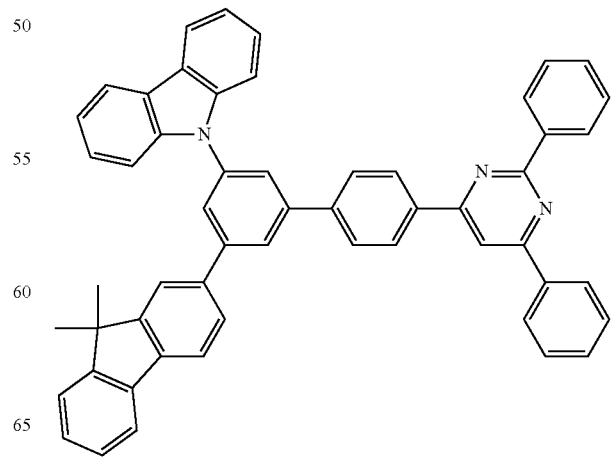

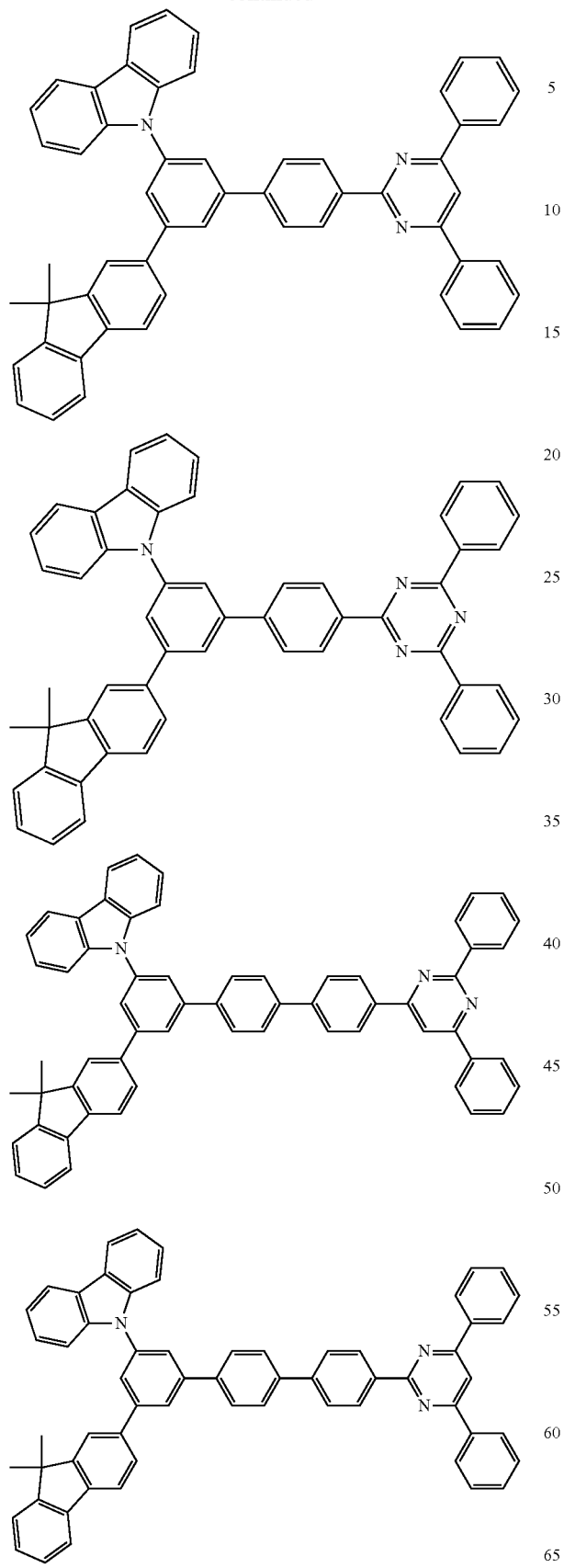
[Chemical Formula 18]

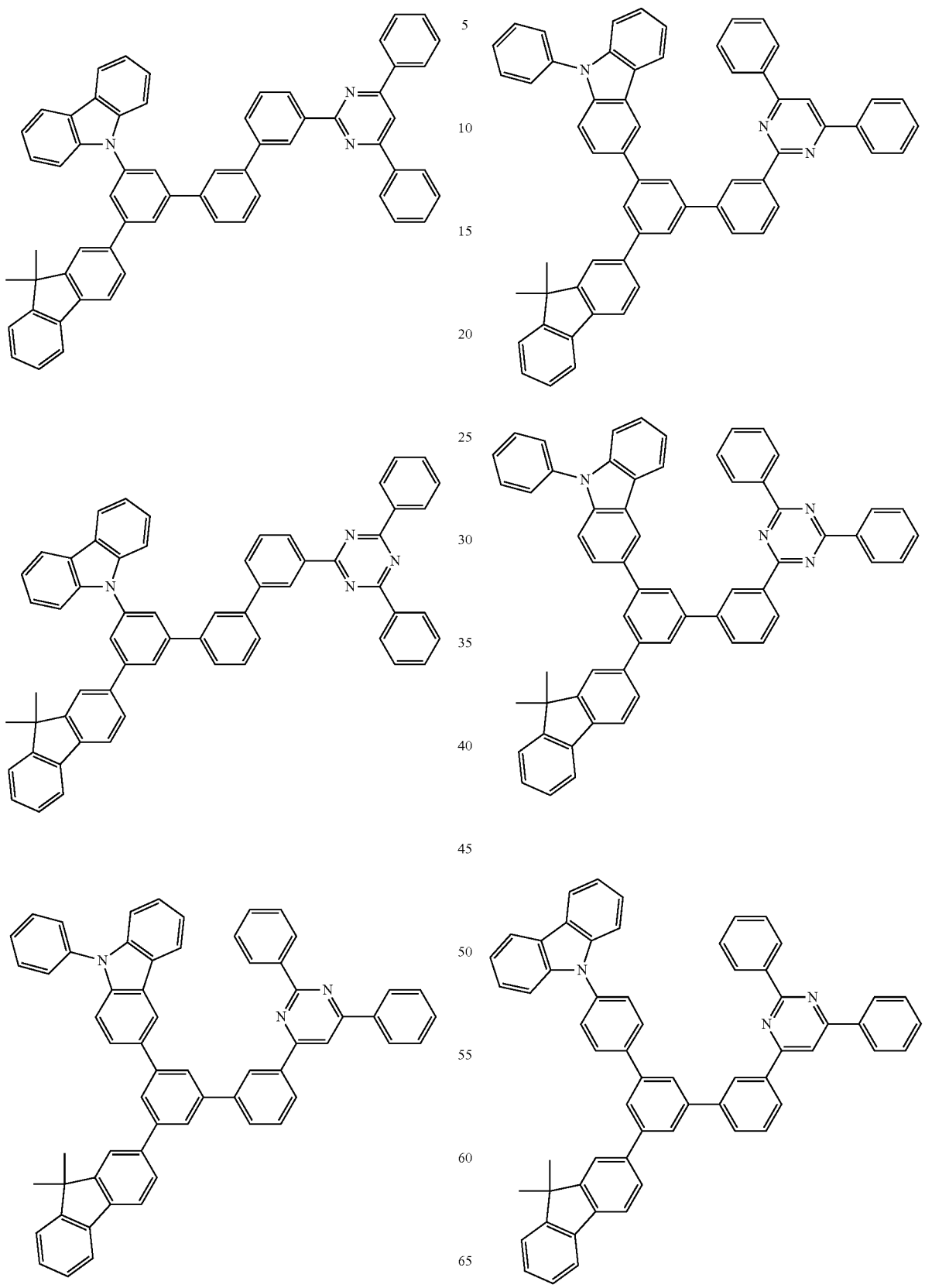

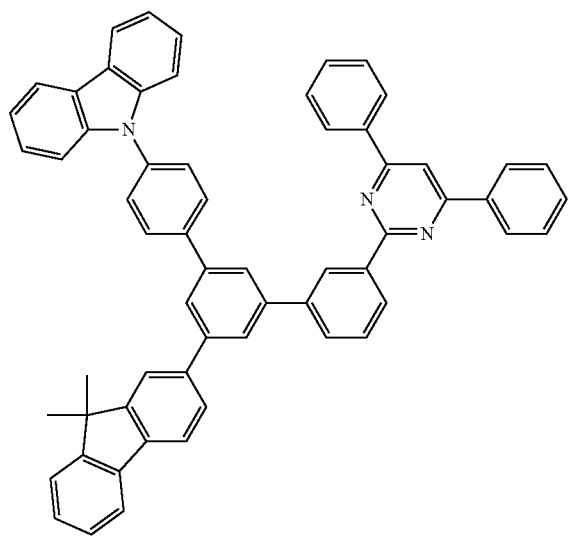
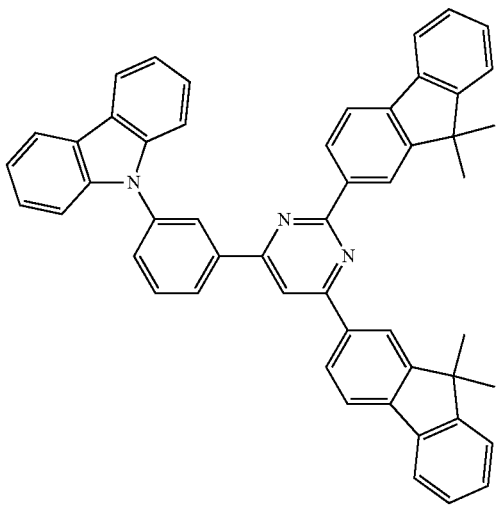
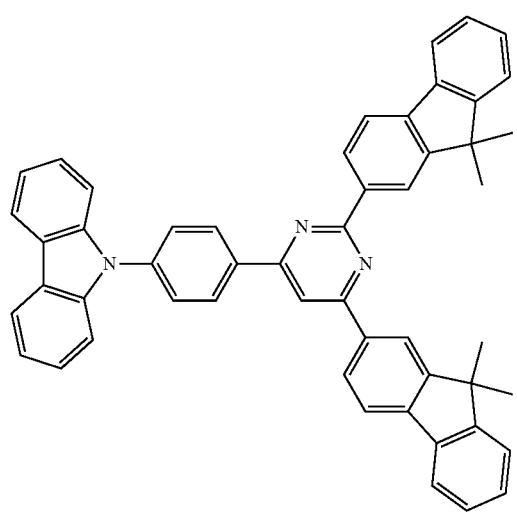
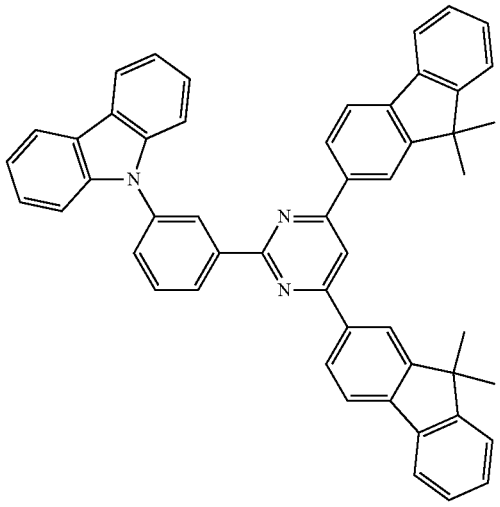
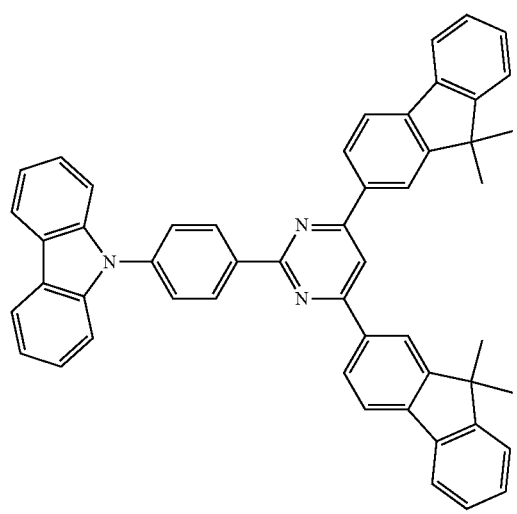
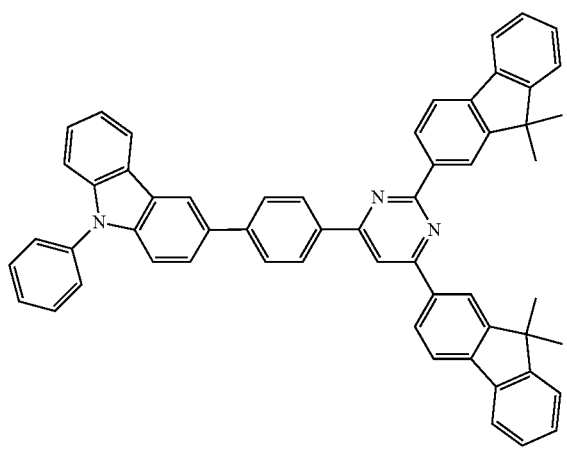

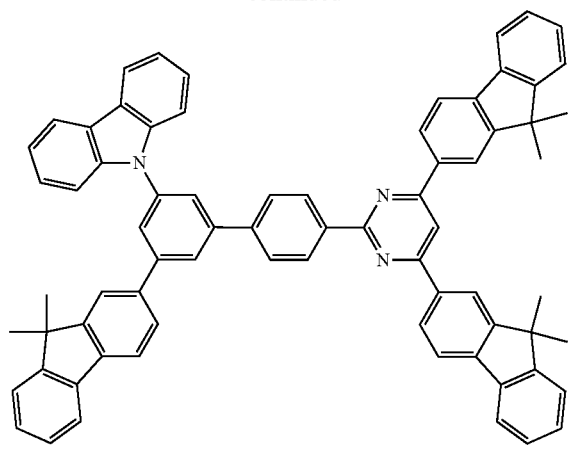
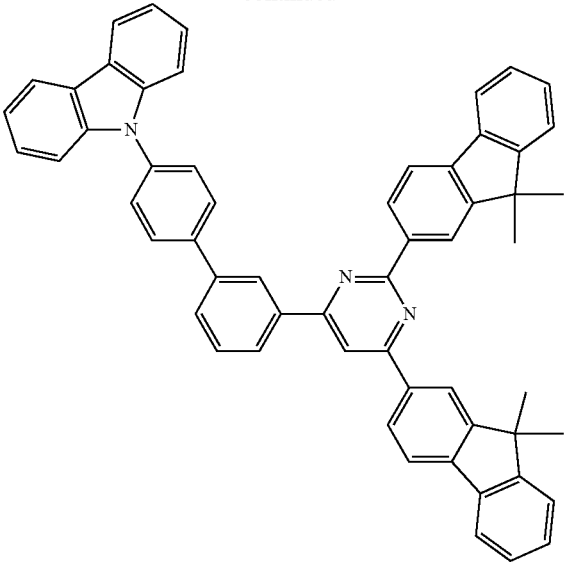
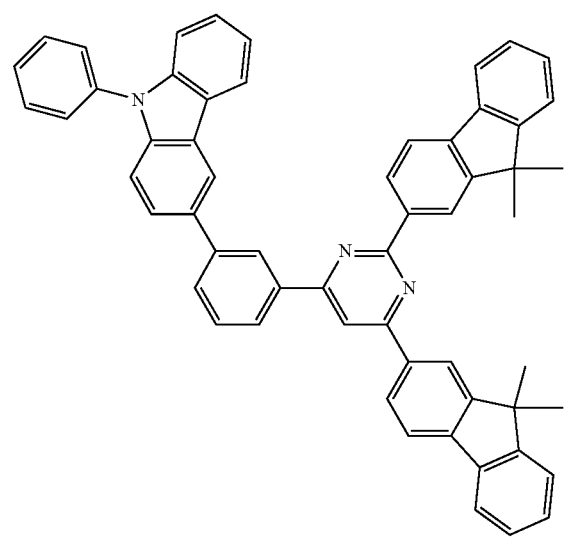
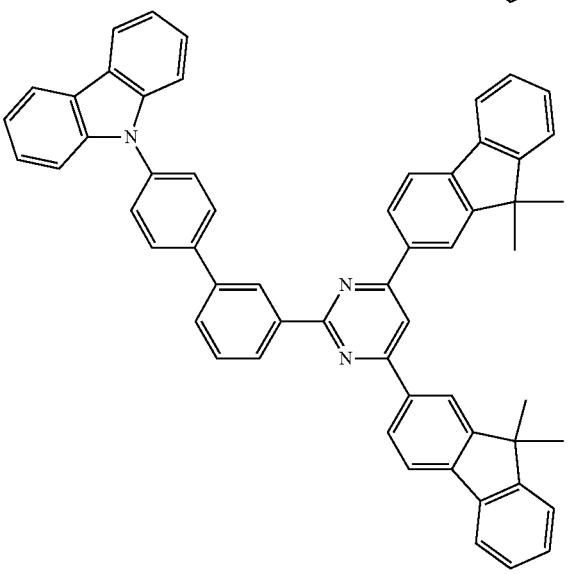
[Chemical Formula 19]
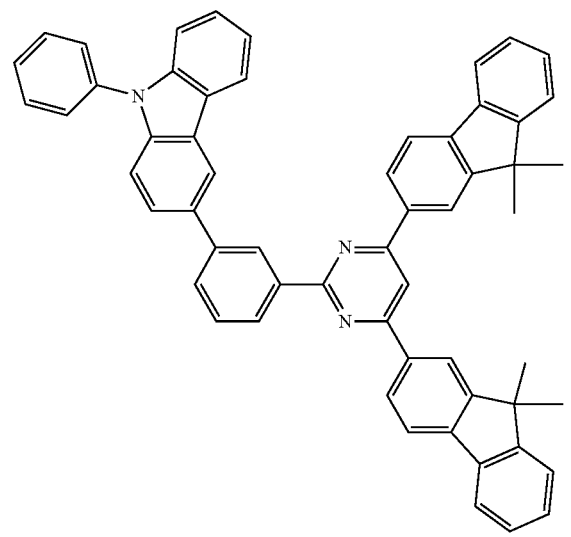
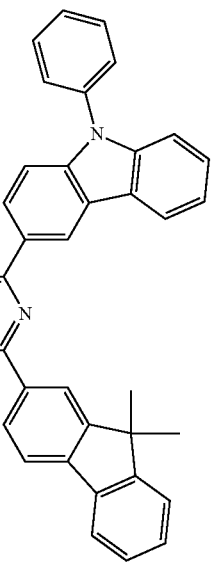

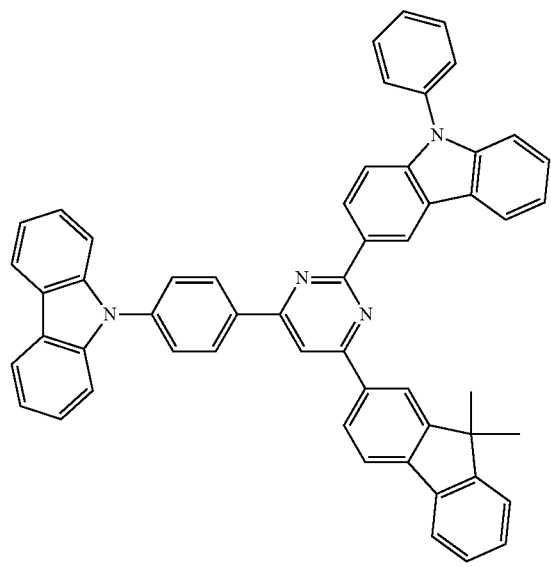
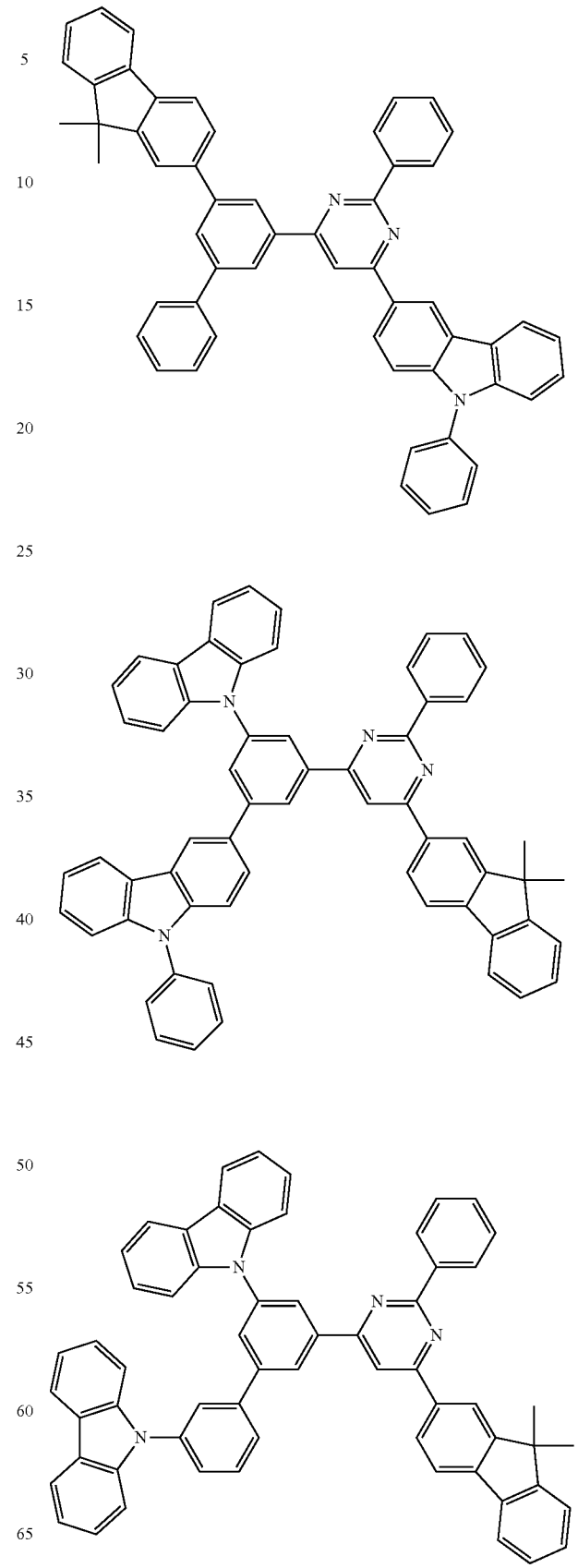

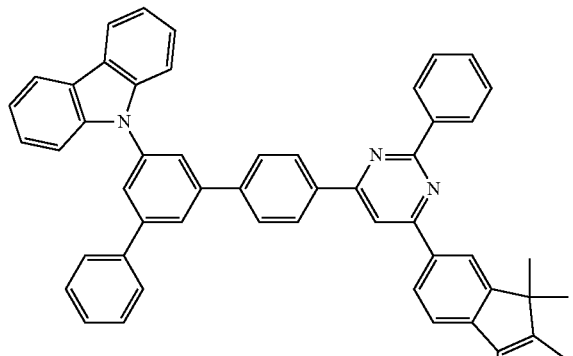
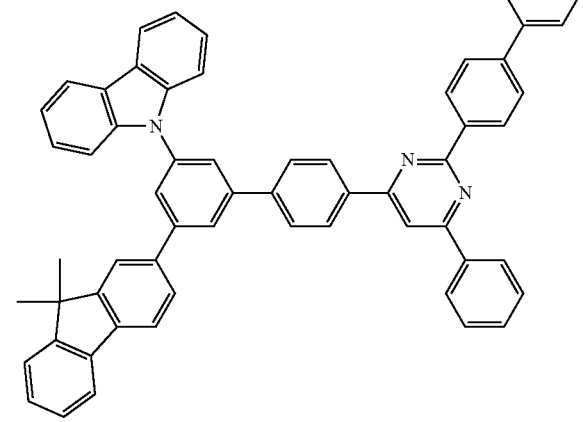
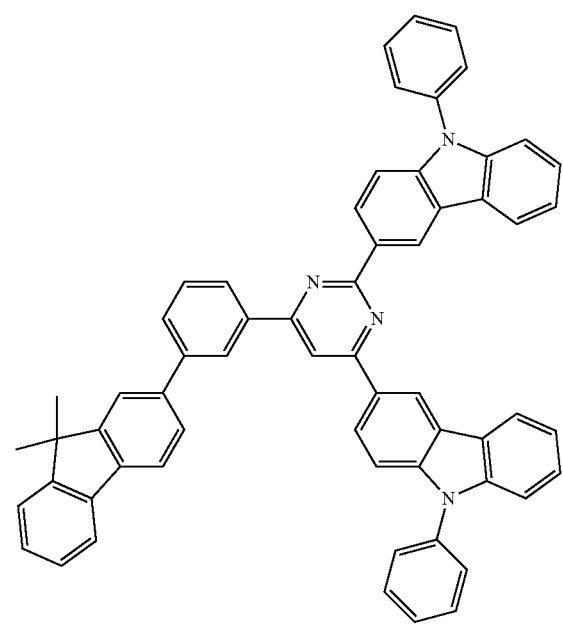
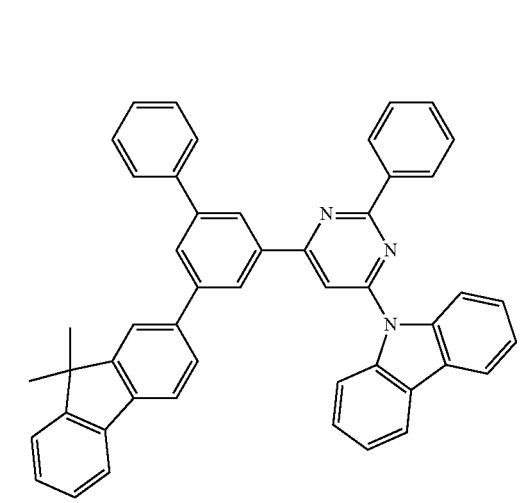
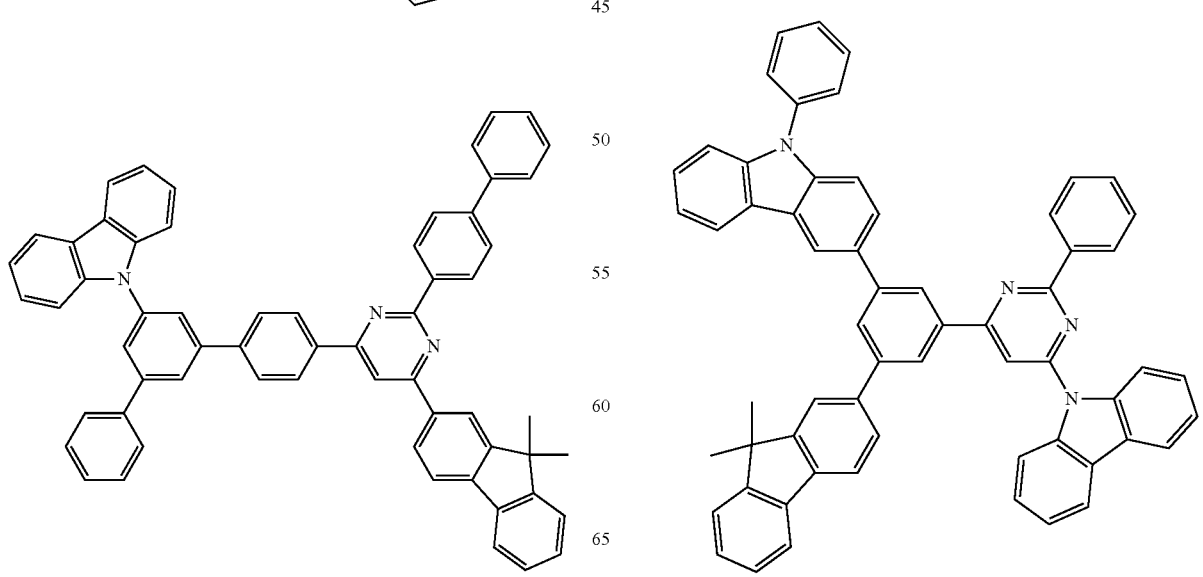
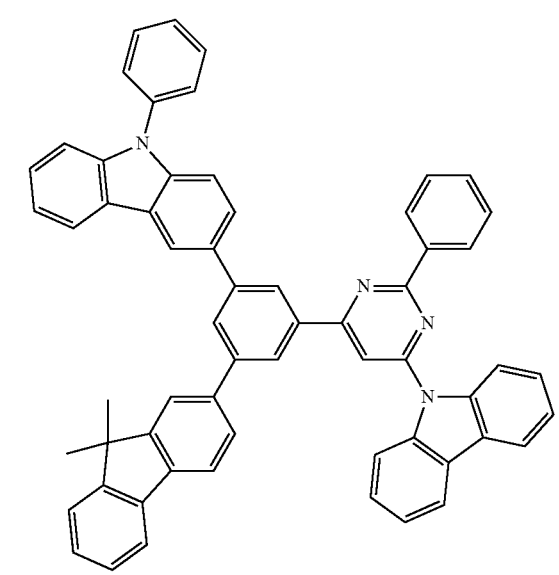

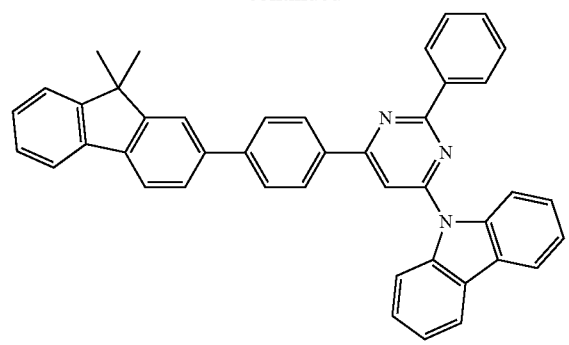
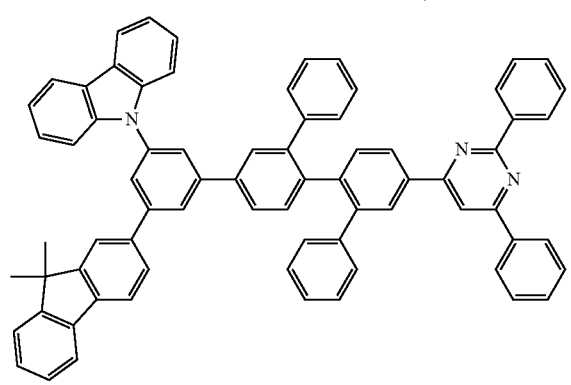
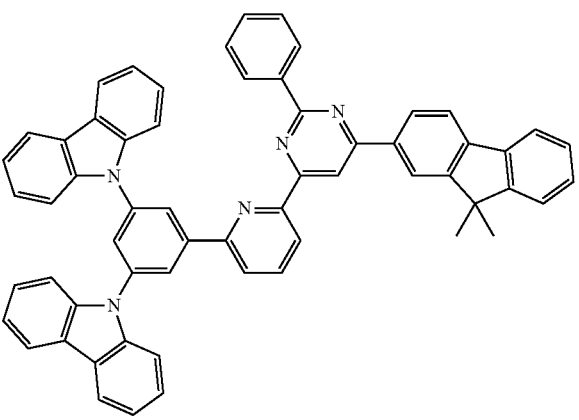
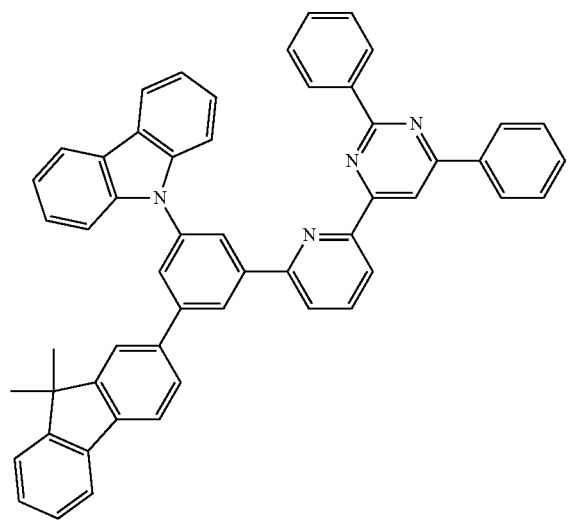
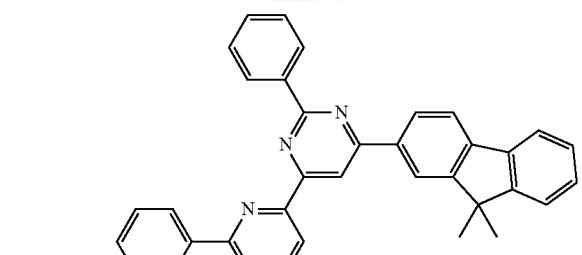
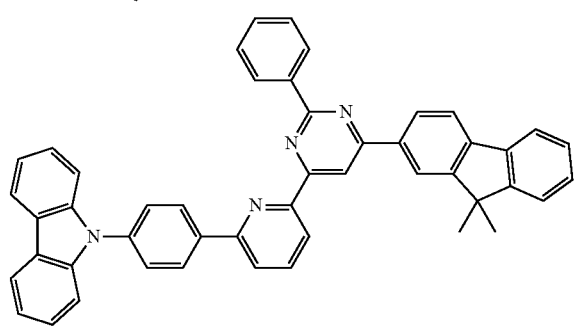
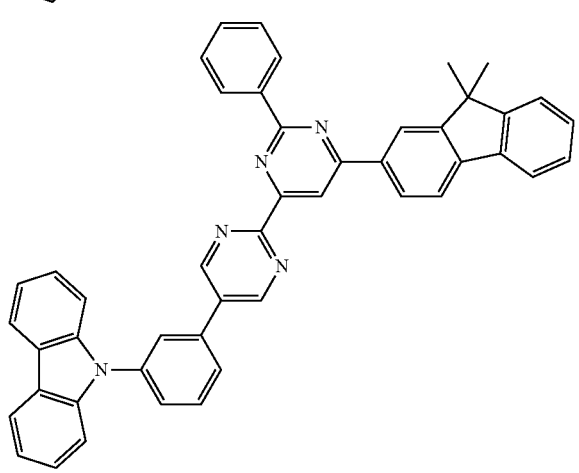
[Chemical Formula 20]
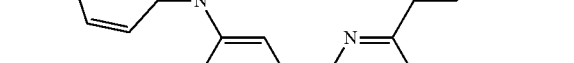

47
-continued
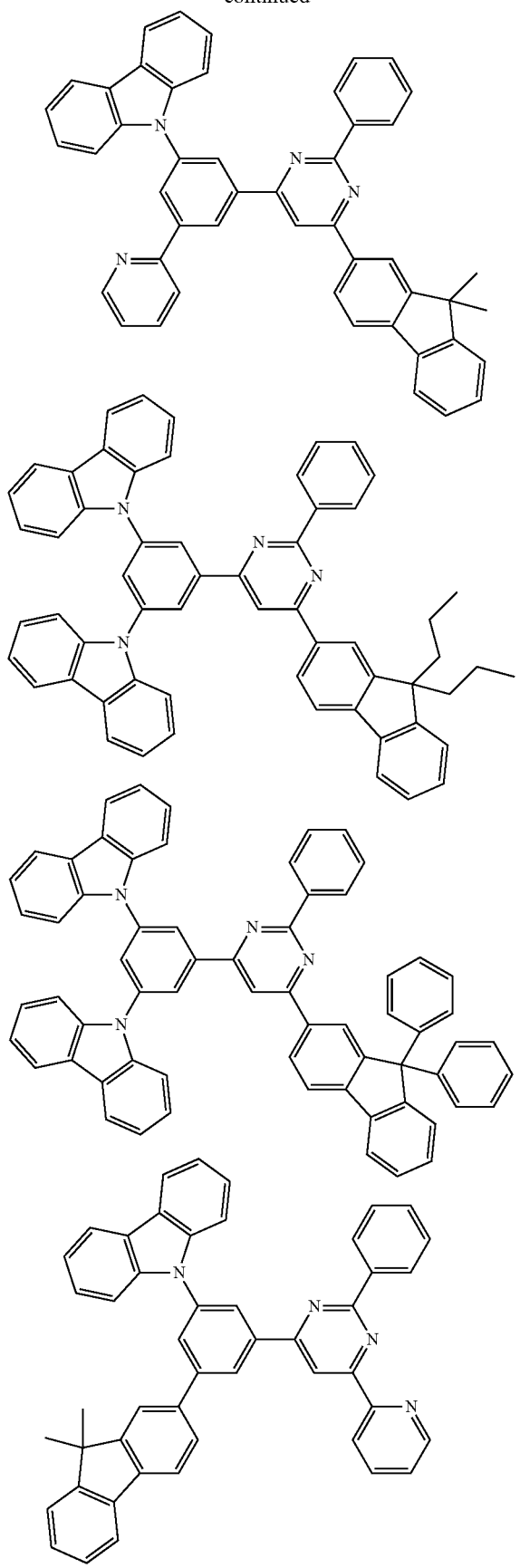
48
-continued
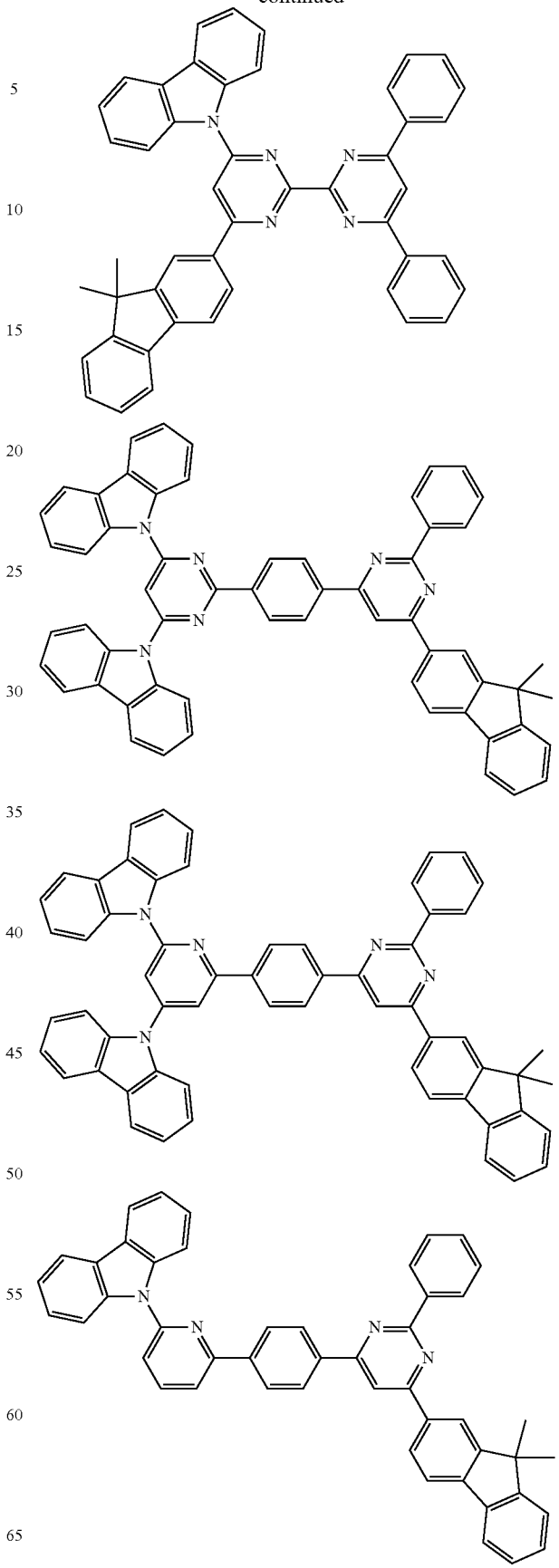

49
-continued
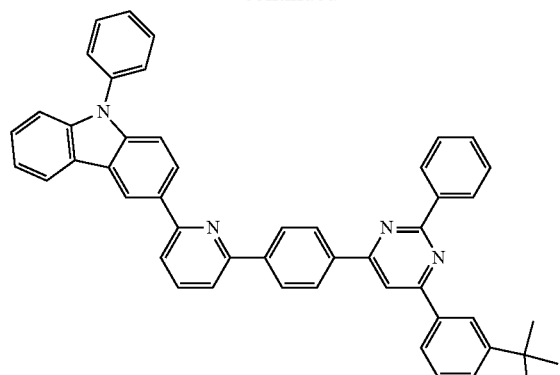
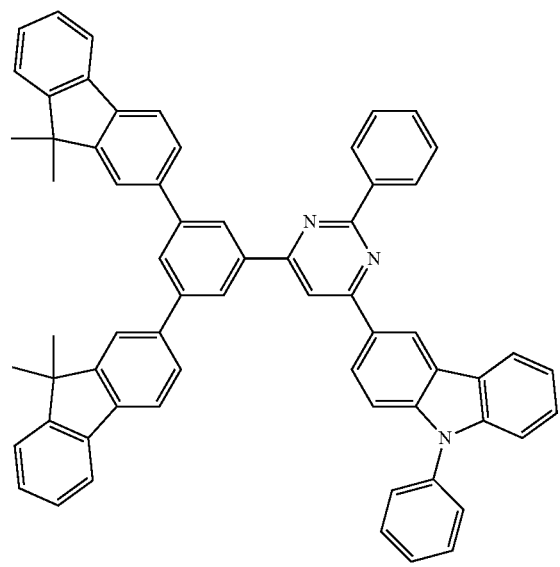
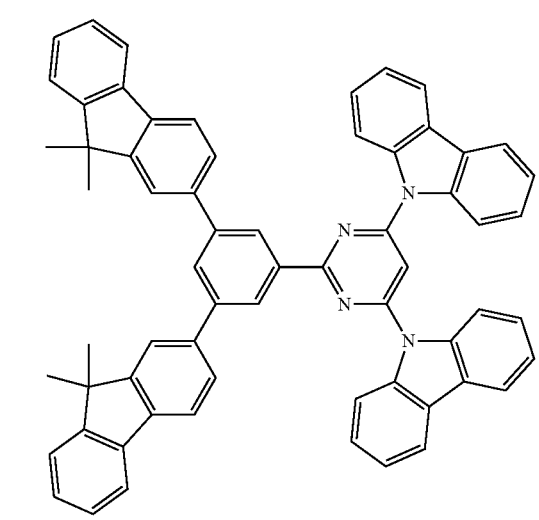
50
-continued
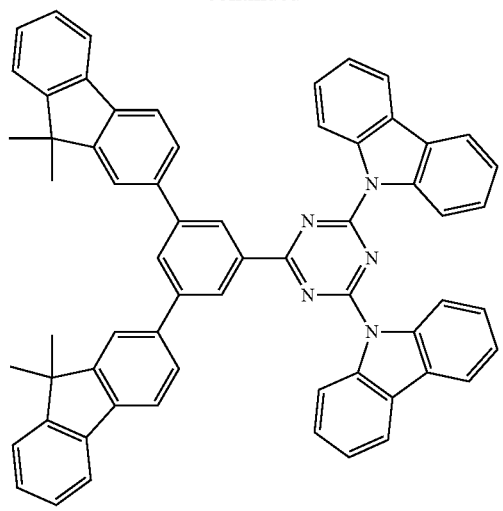
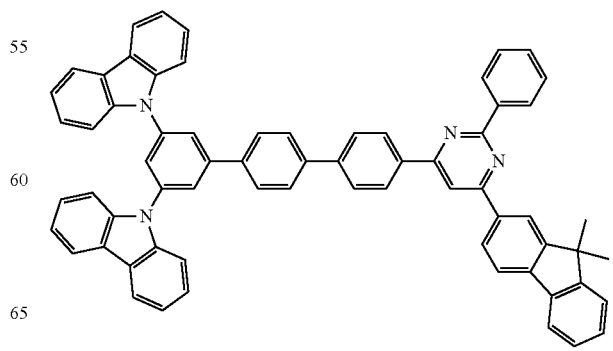

51
-continued
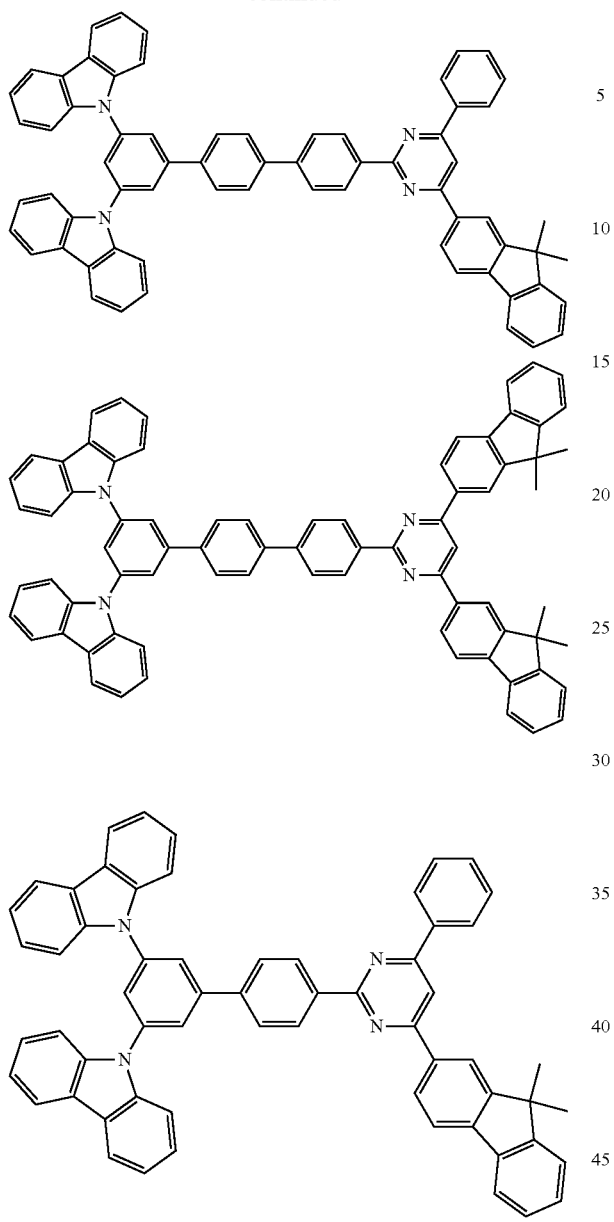
[Chemical Formula 21]
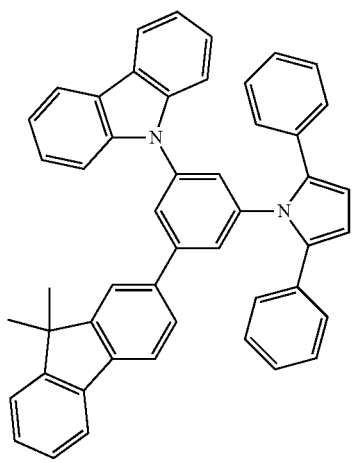
52
-continued
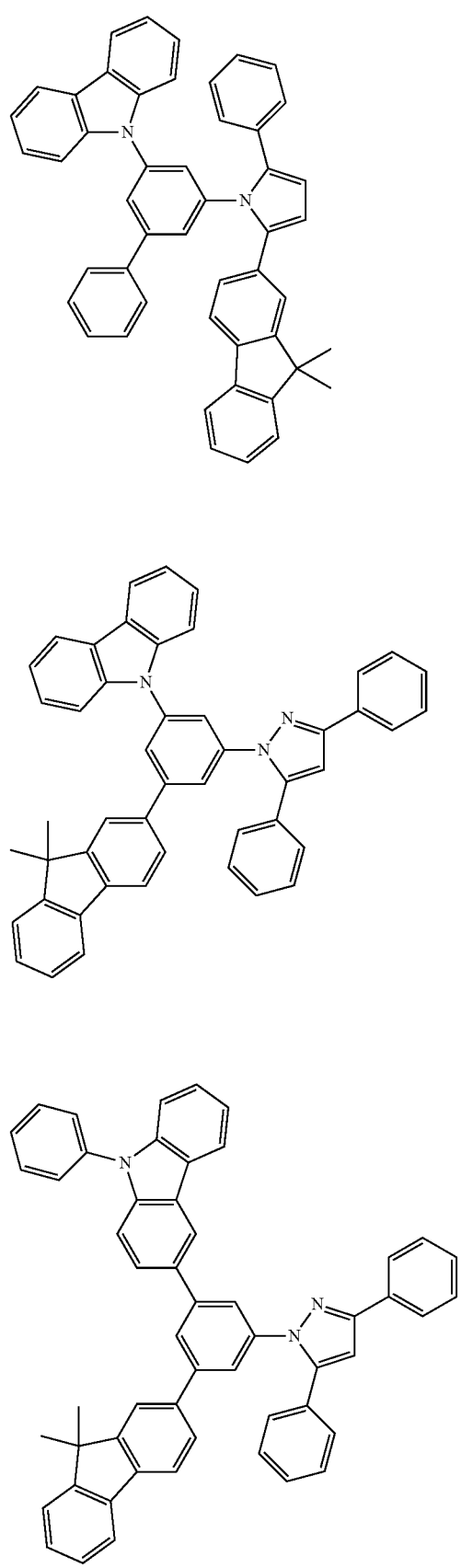

53
-continued
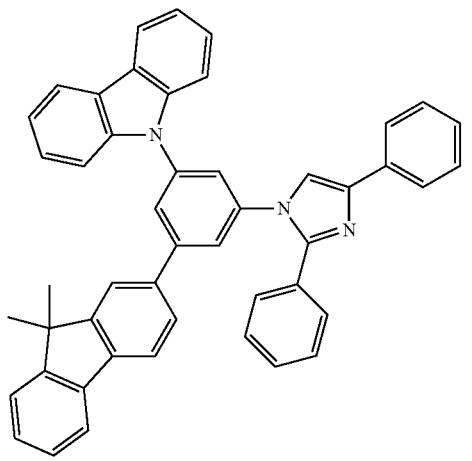
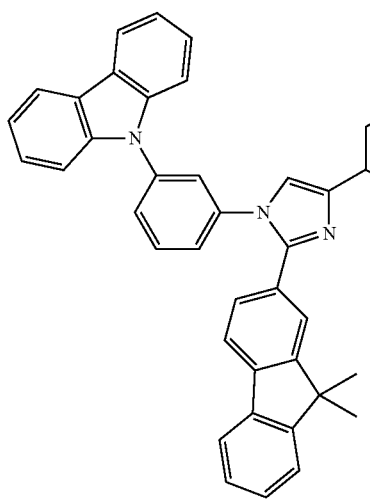
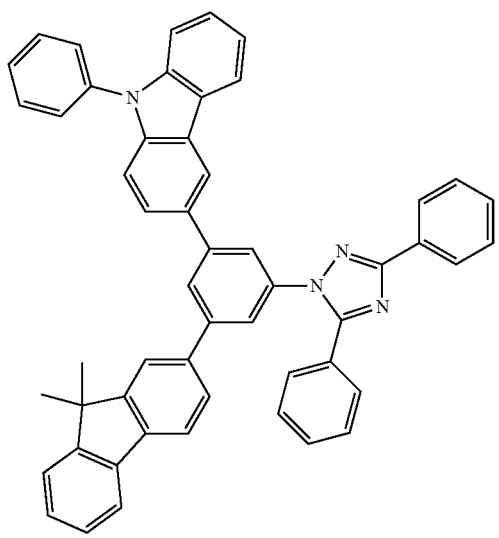
54
-continued
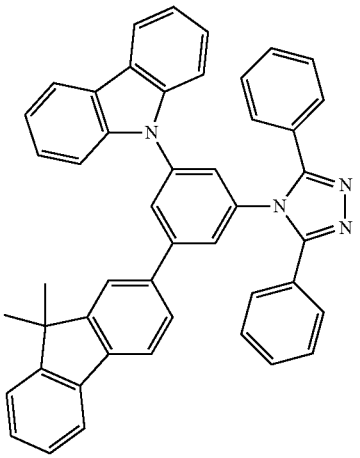
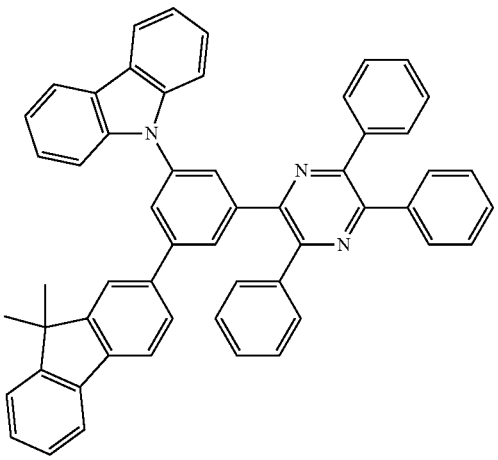
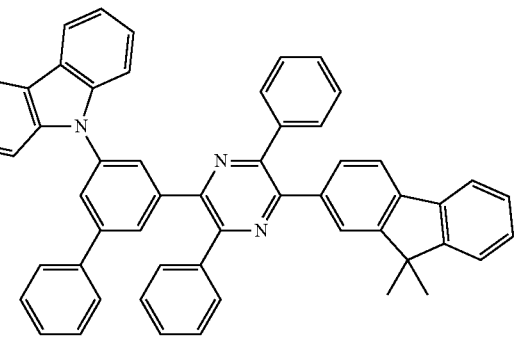
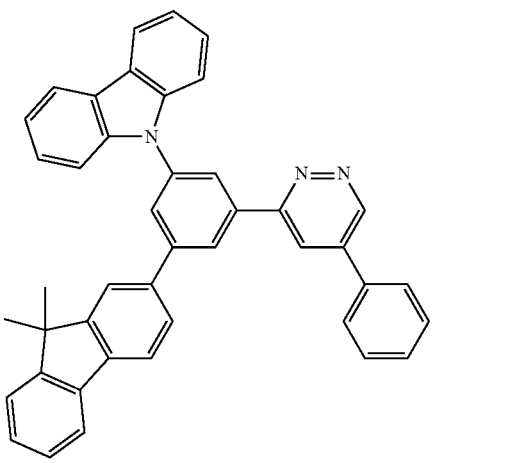

55
-continued
56
-continued
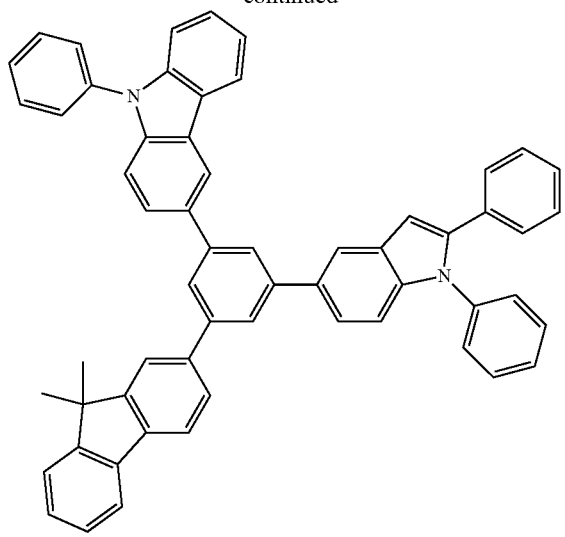
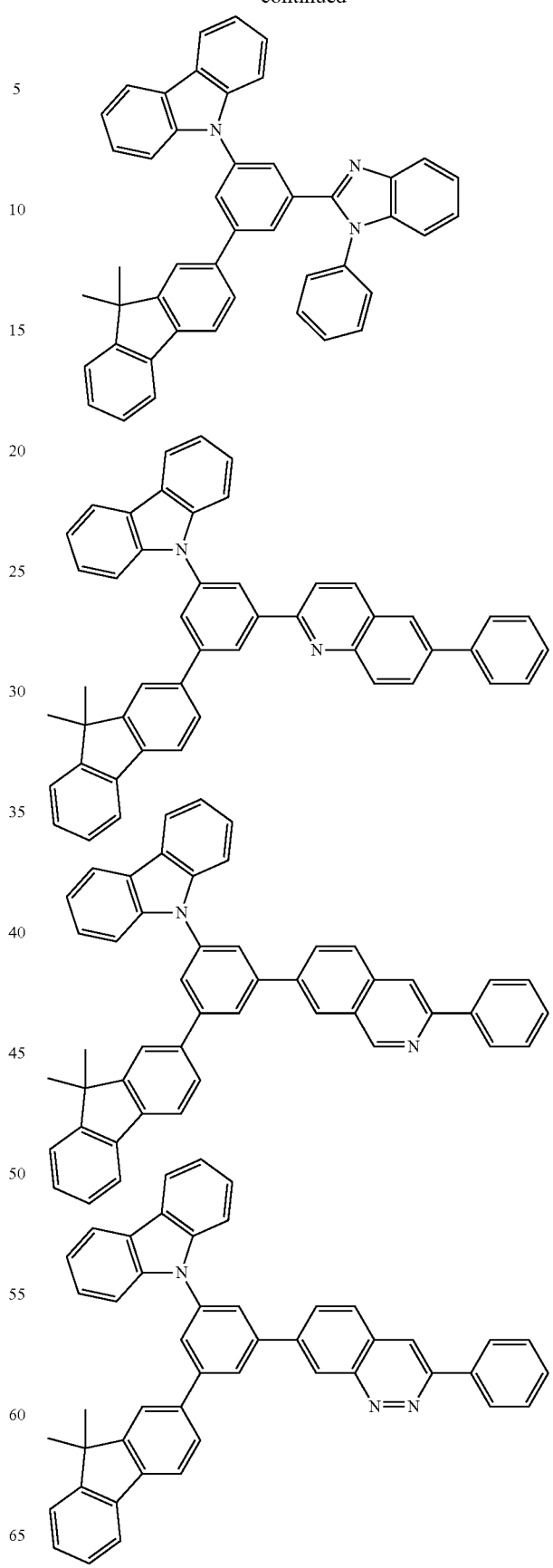

57
-continued
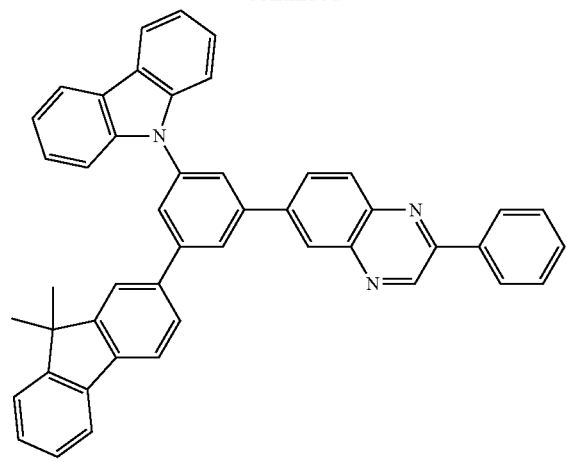
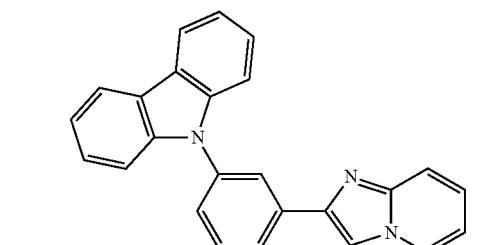
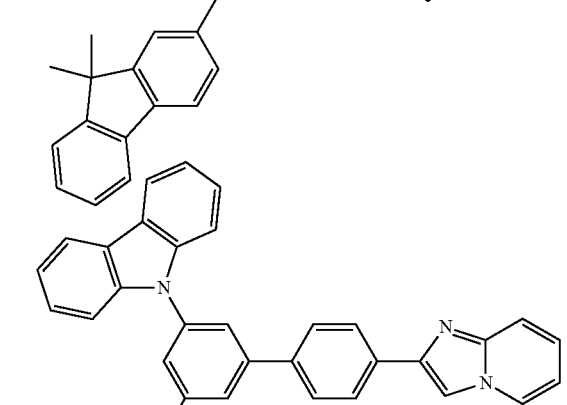
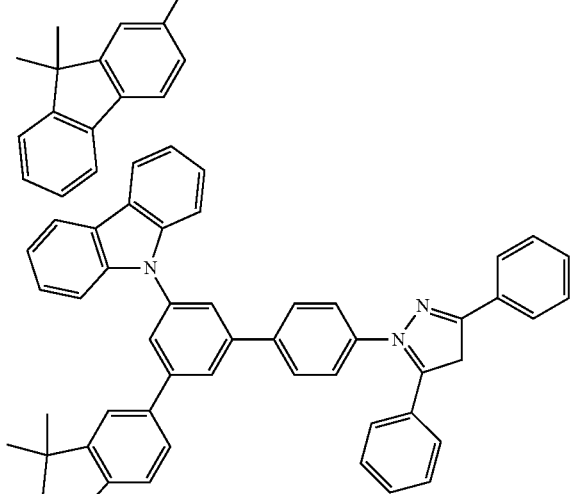
58
-continued
[Chemical Formula 22]
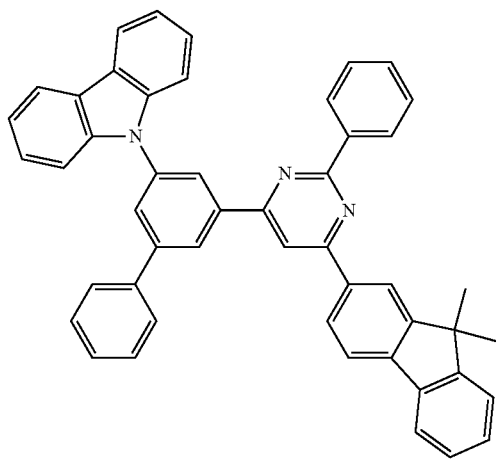
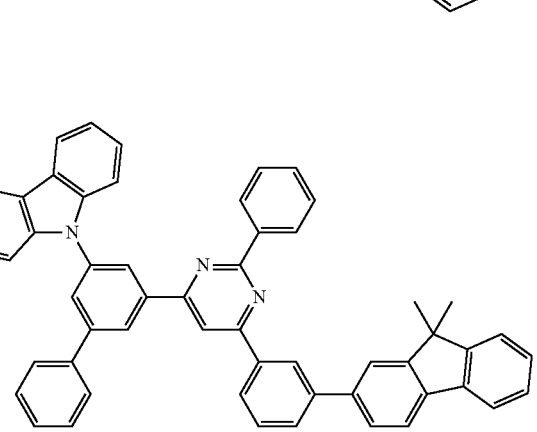
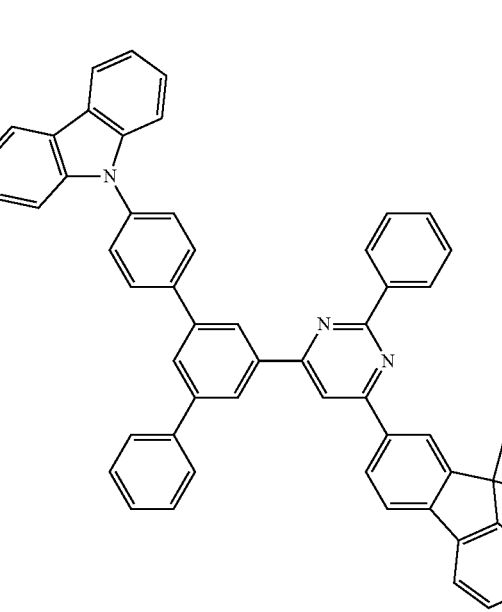

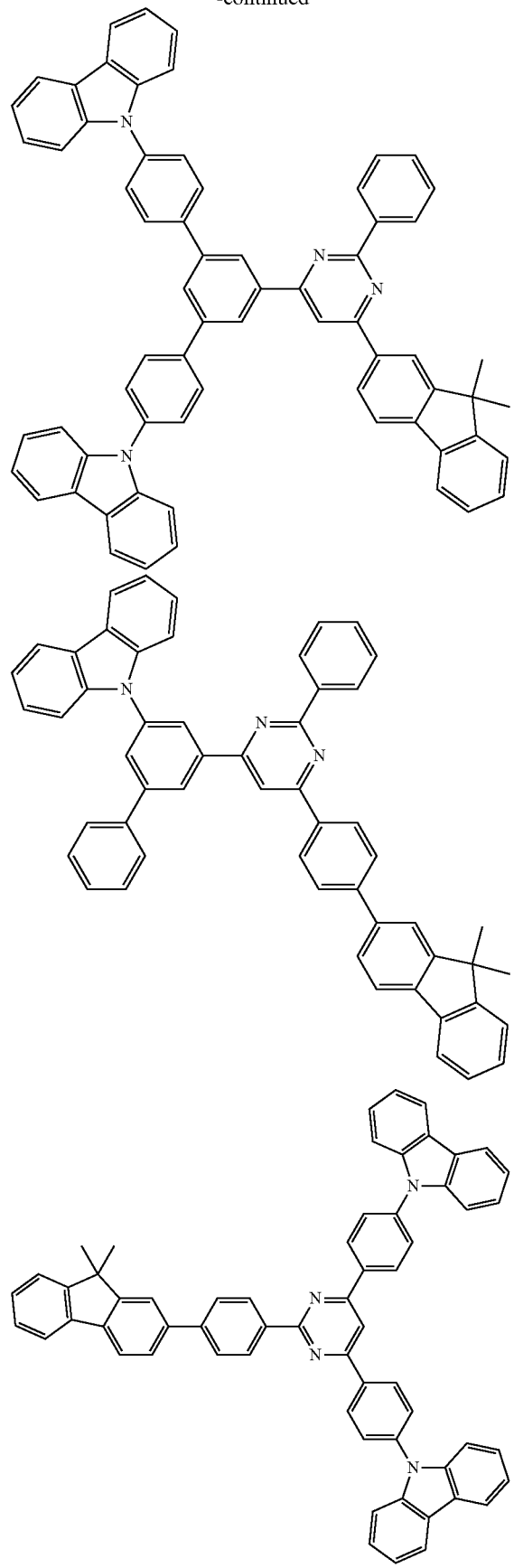
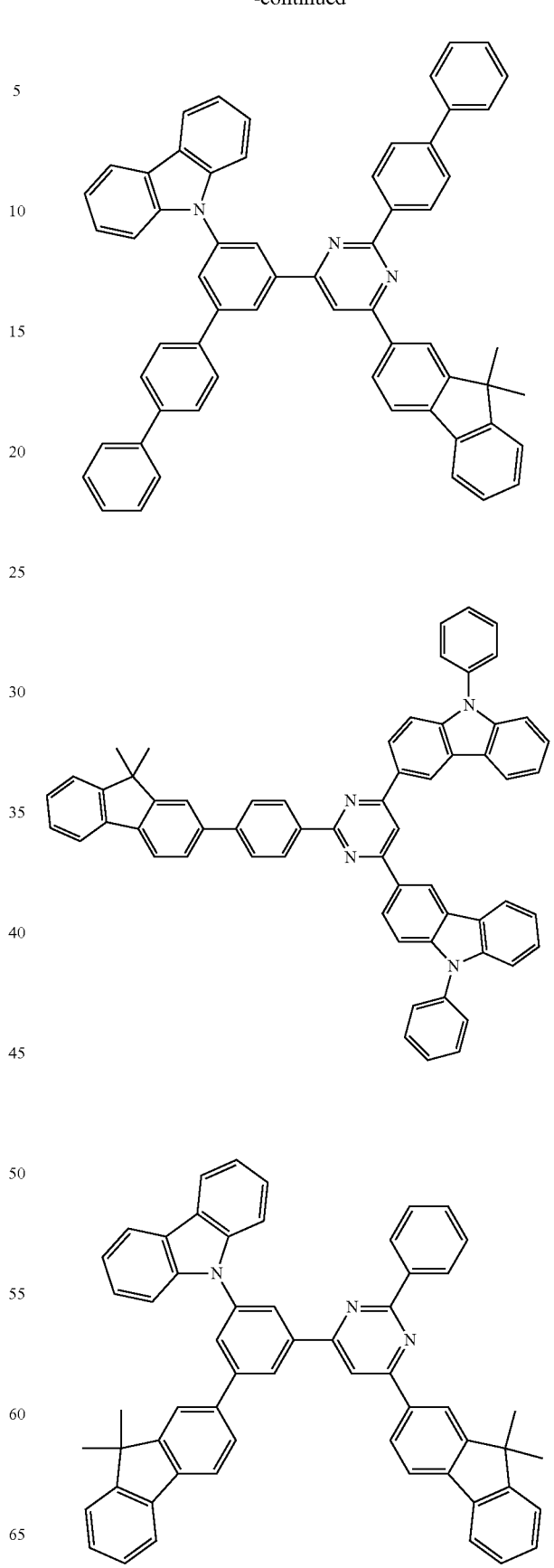

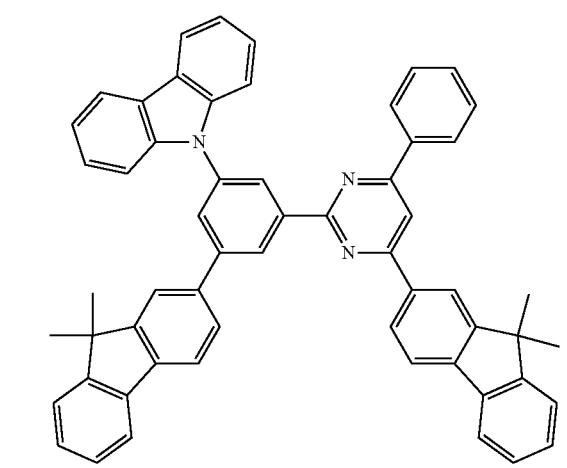
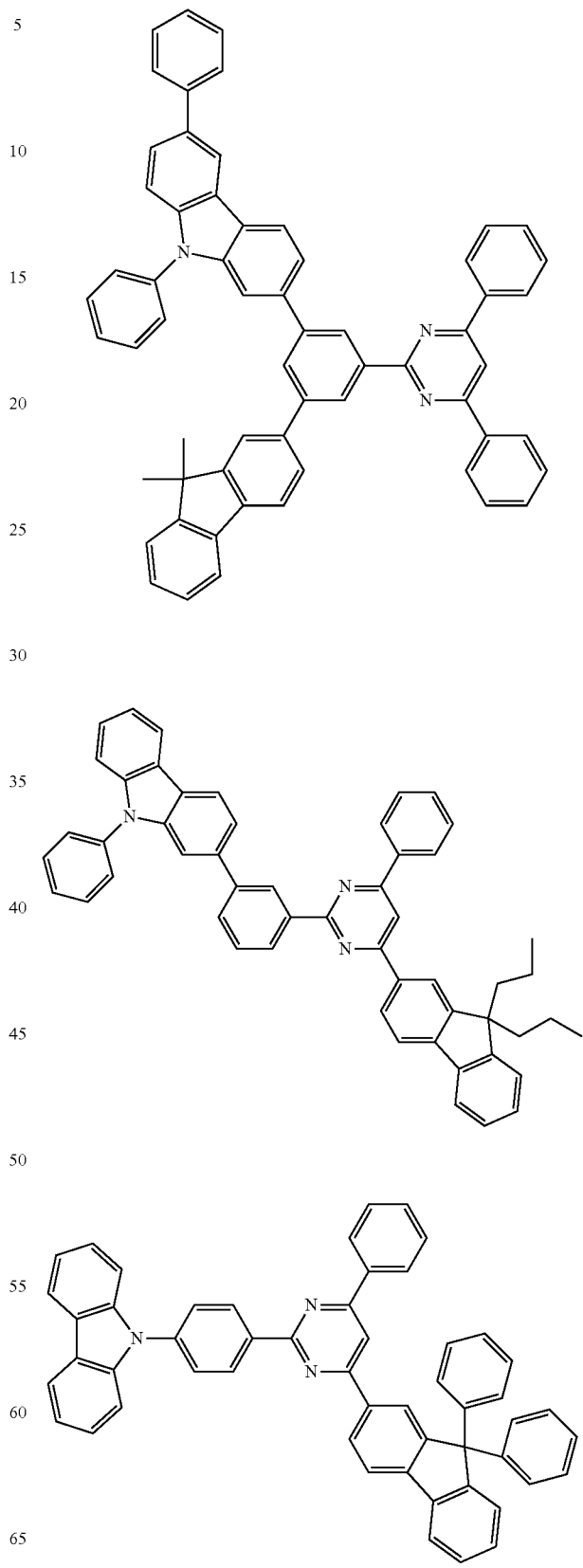

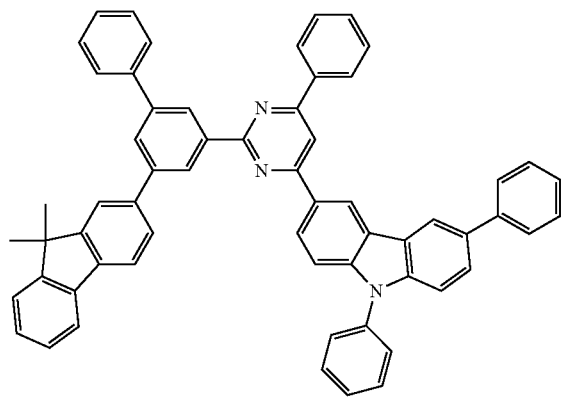
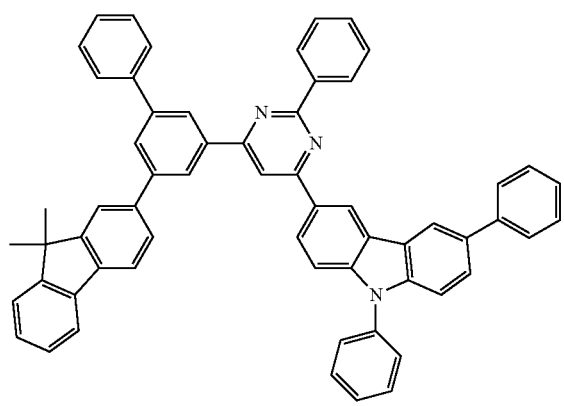
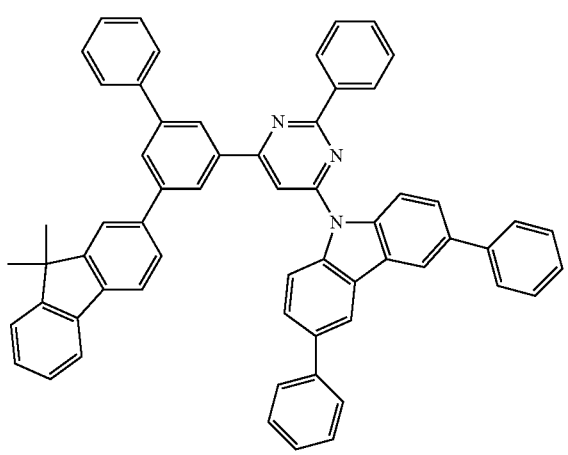
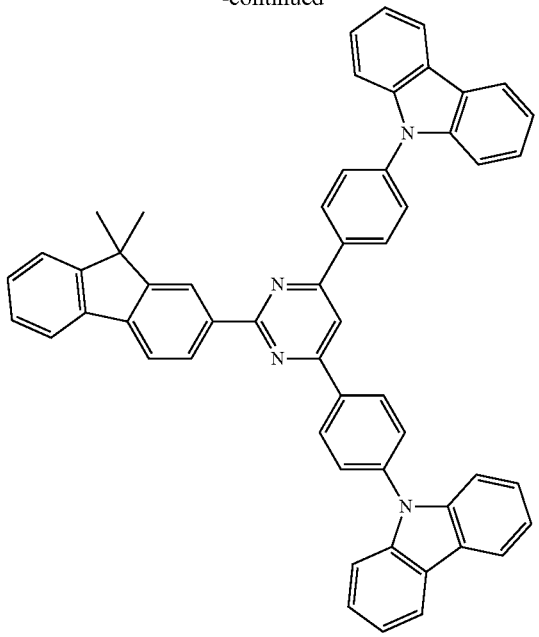
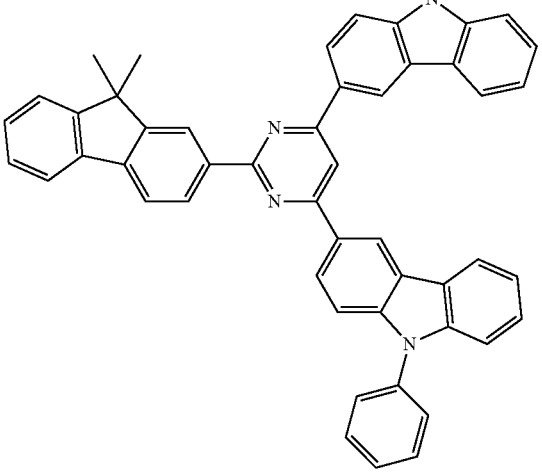
[Chemical Formula 23]
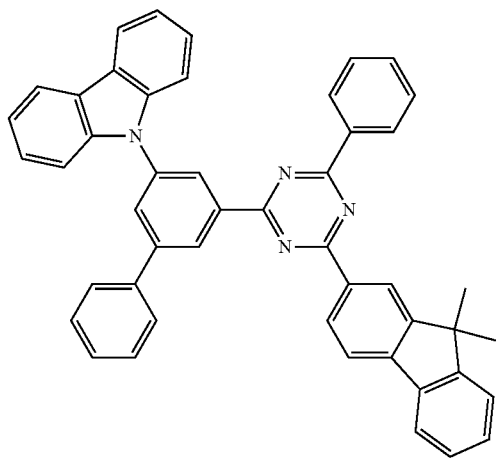

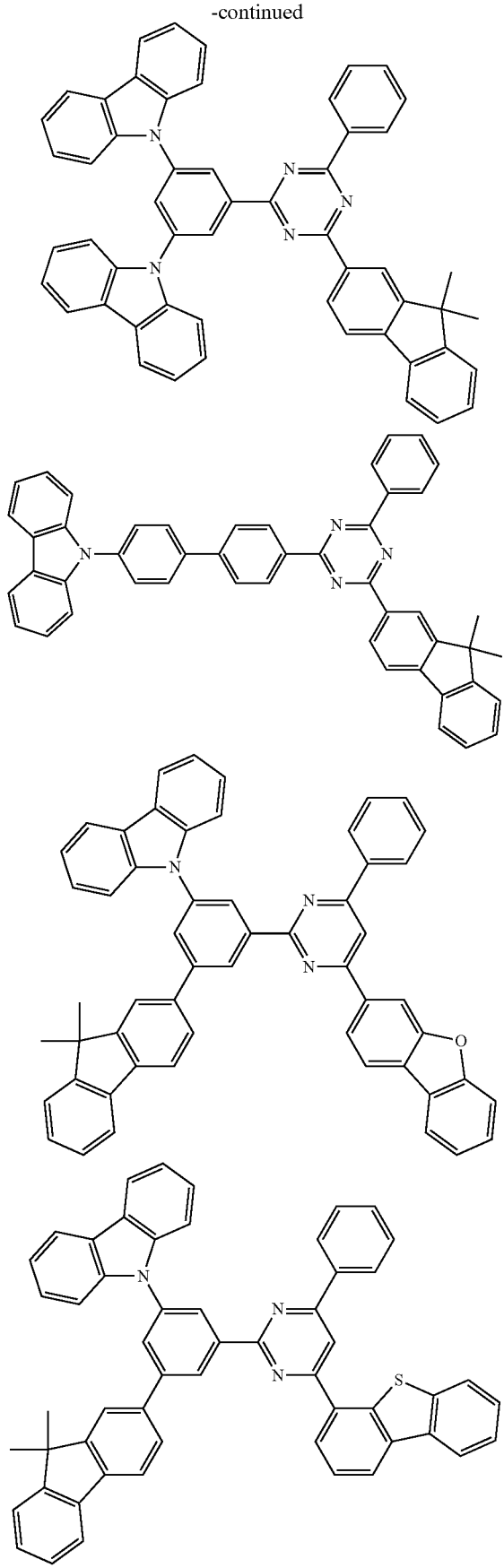
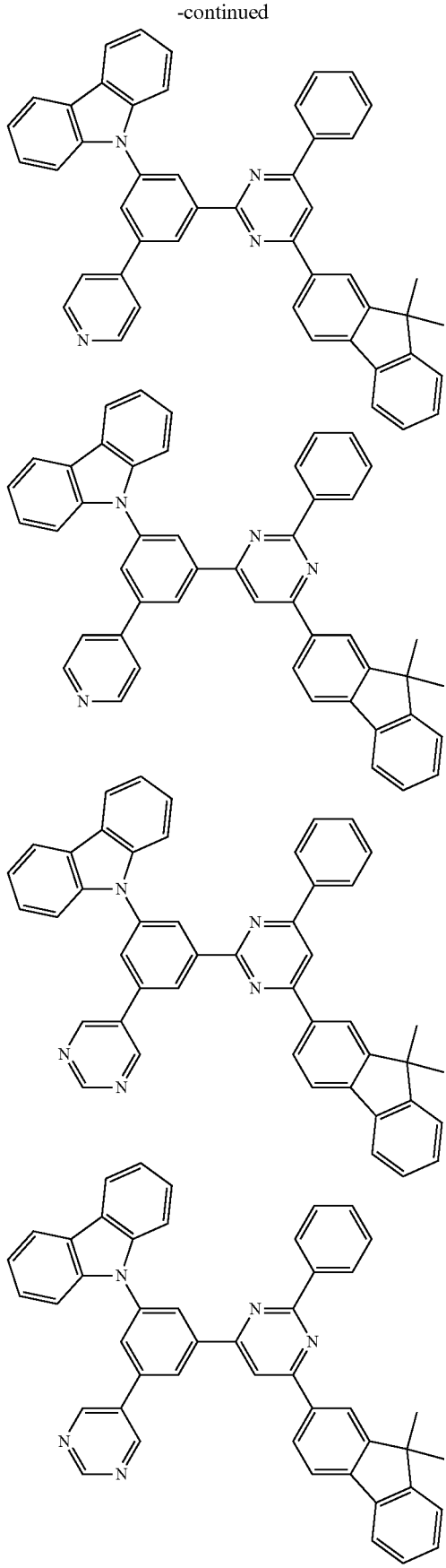

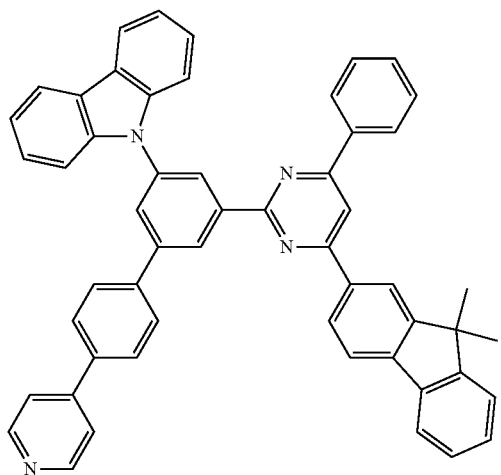
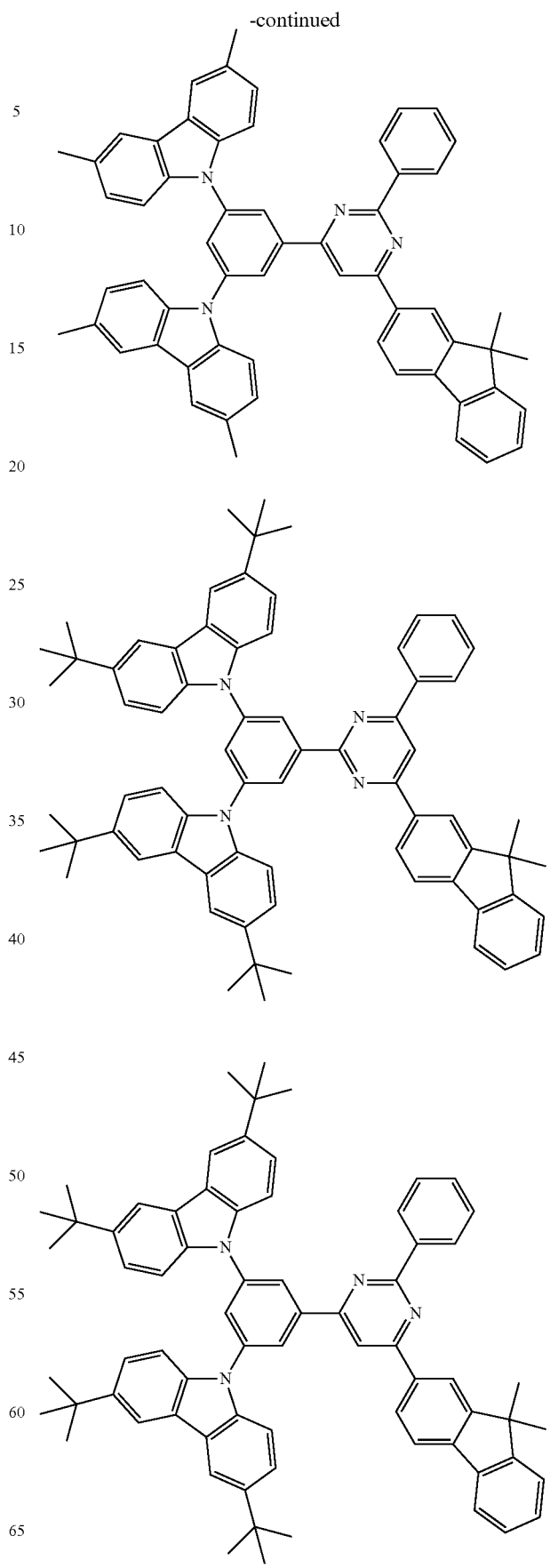

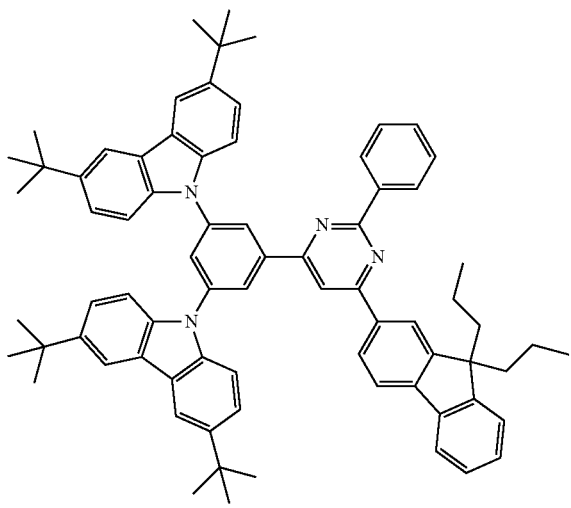
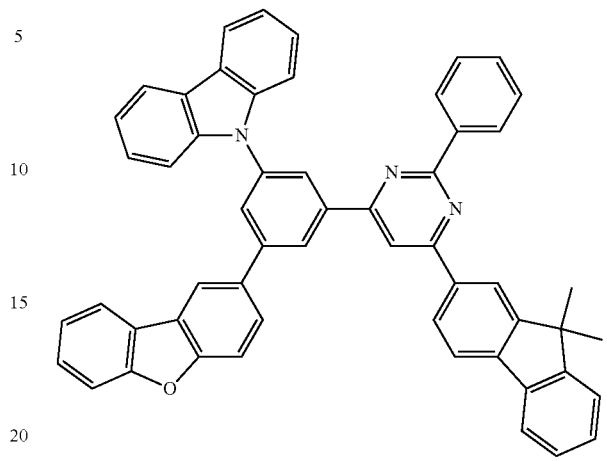
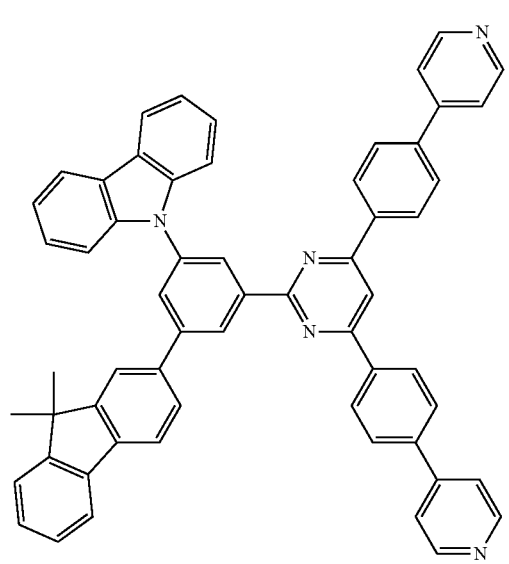
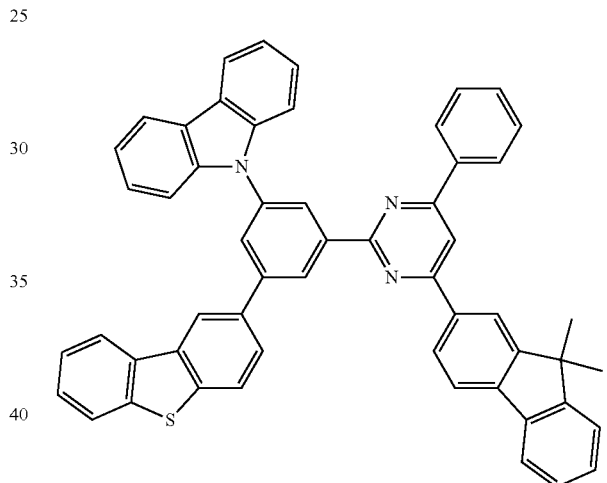
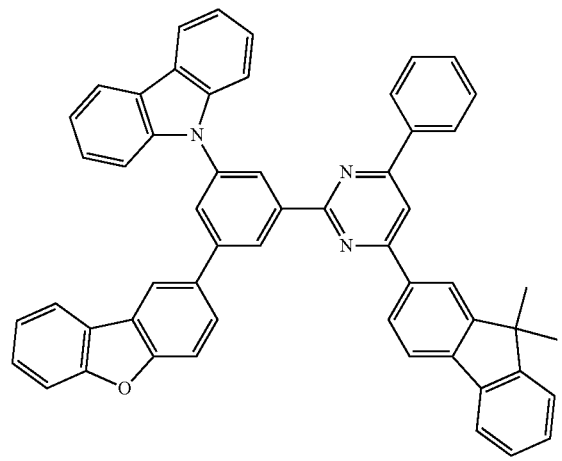
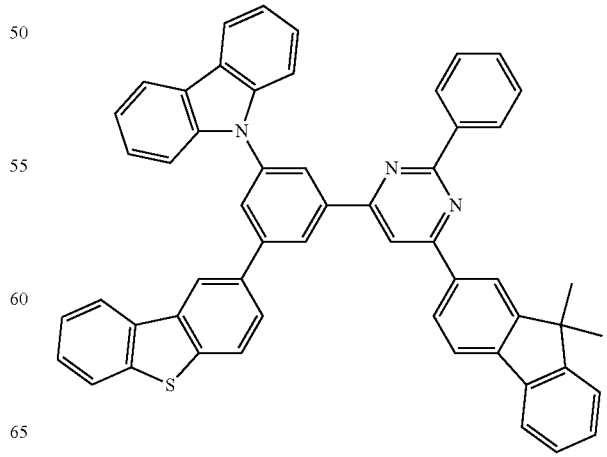

[Chemical Formula 24]
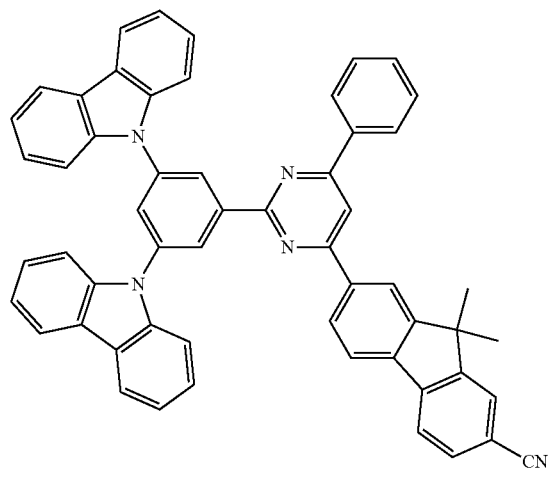
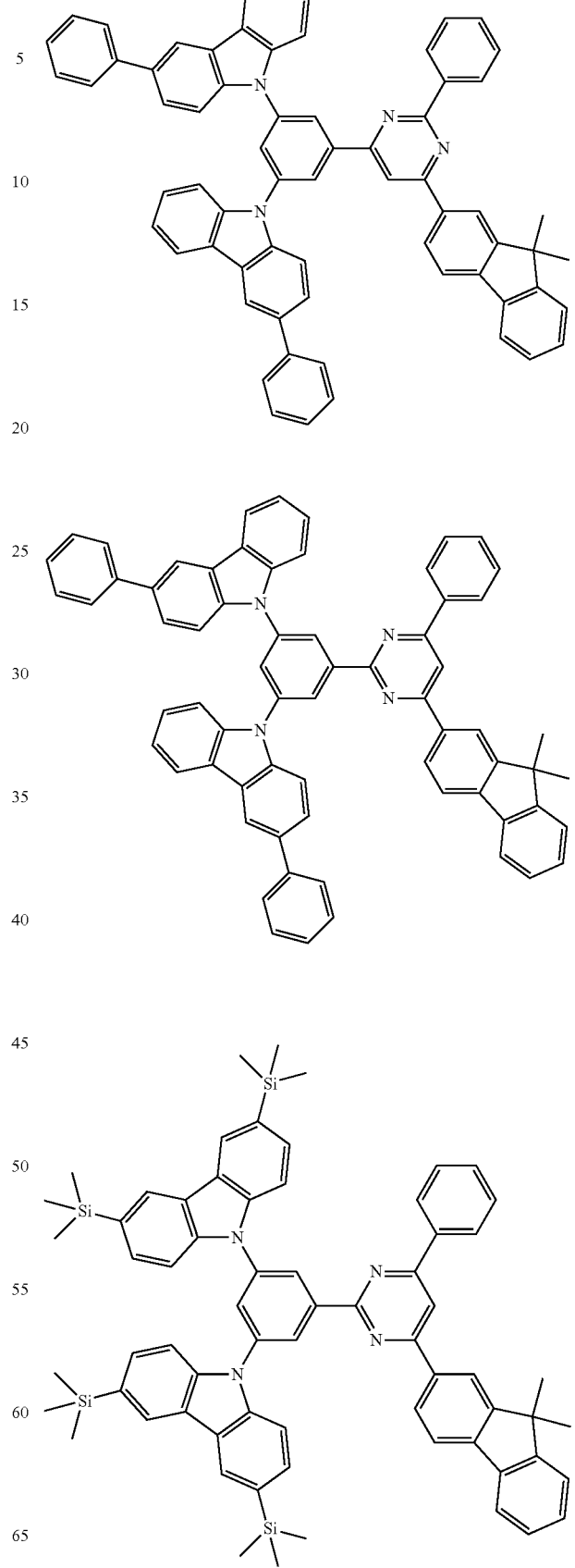

73
-continued
74
-continued
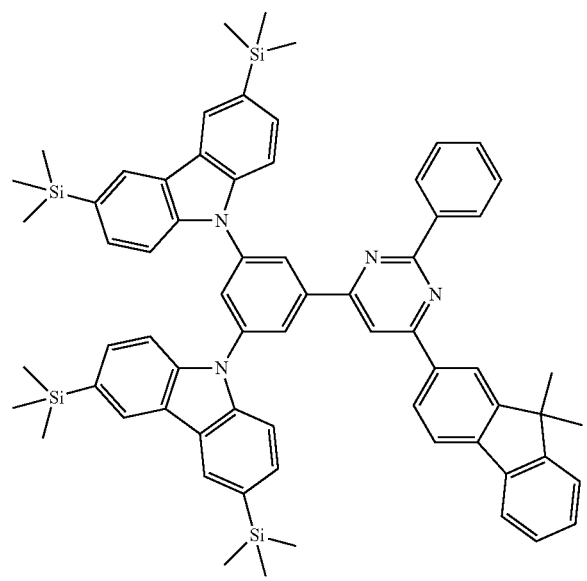
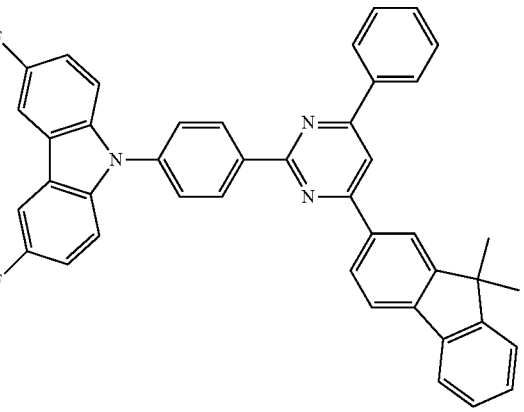
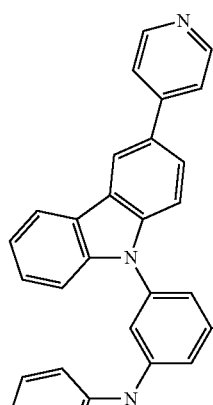
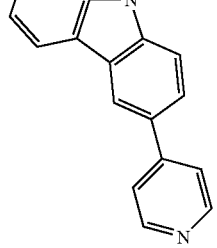
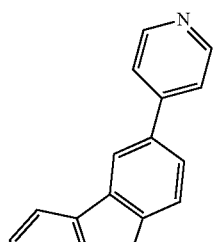
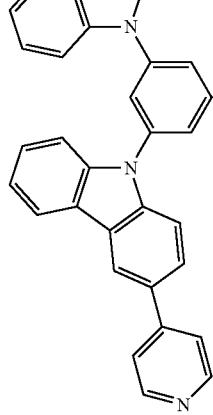

75
-continued
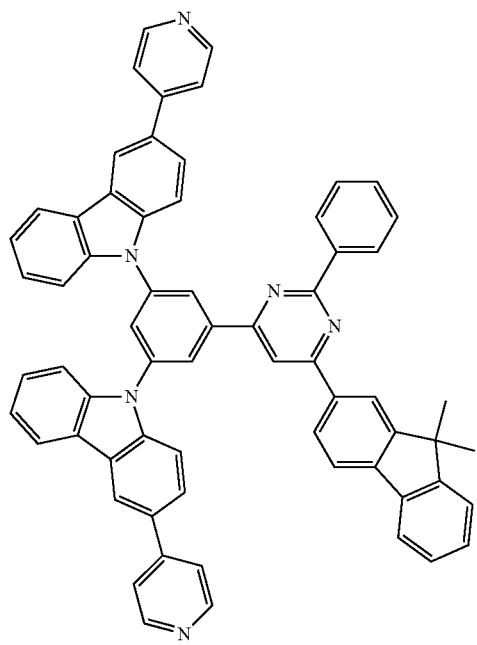
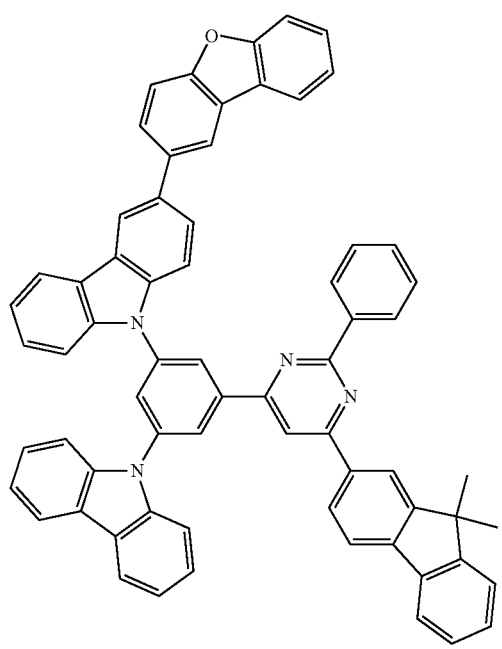
76
-continued
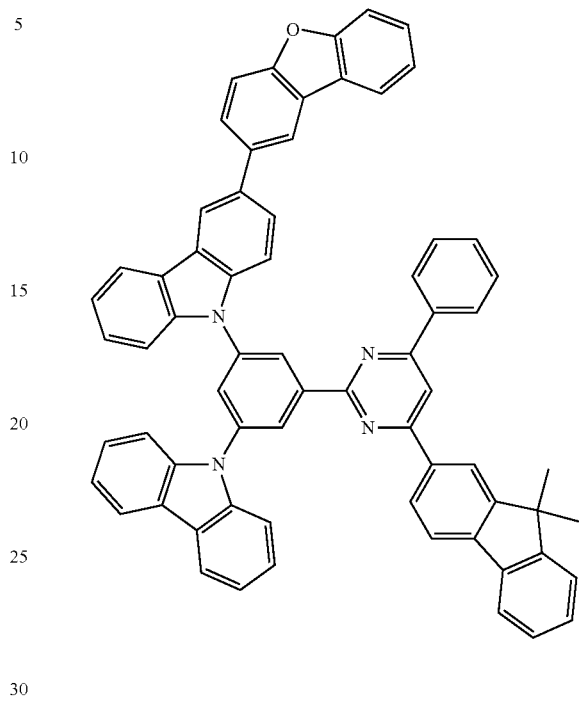

[Chemical Formula 25]
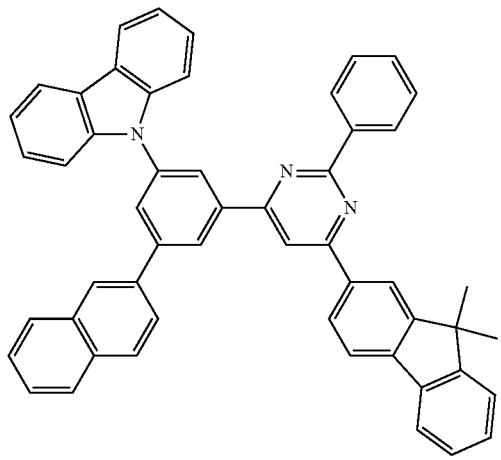
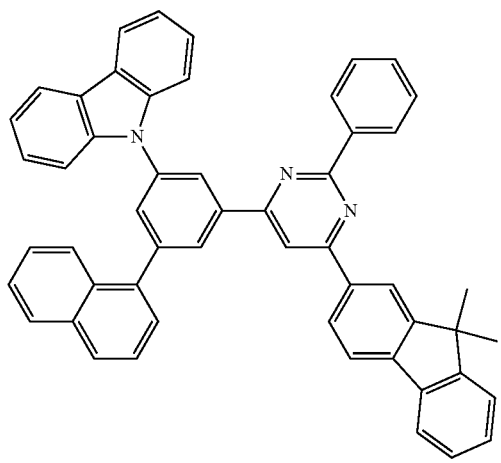
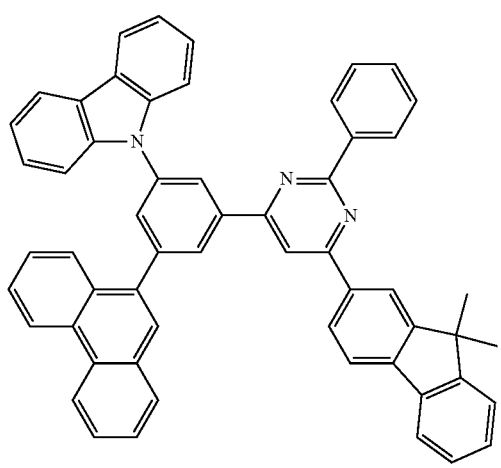
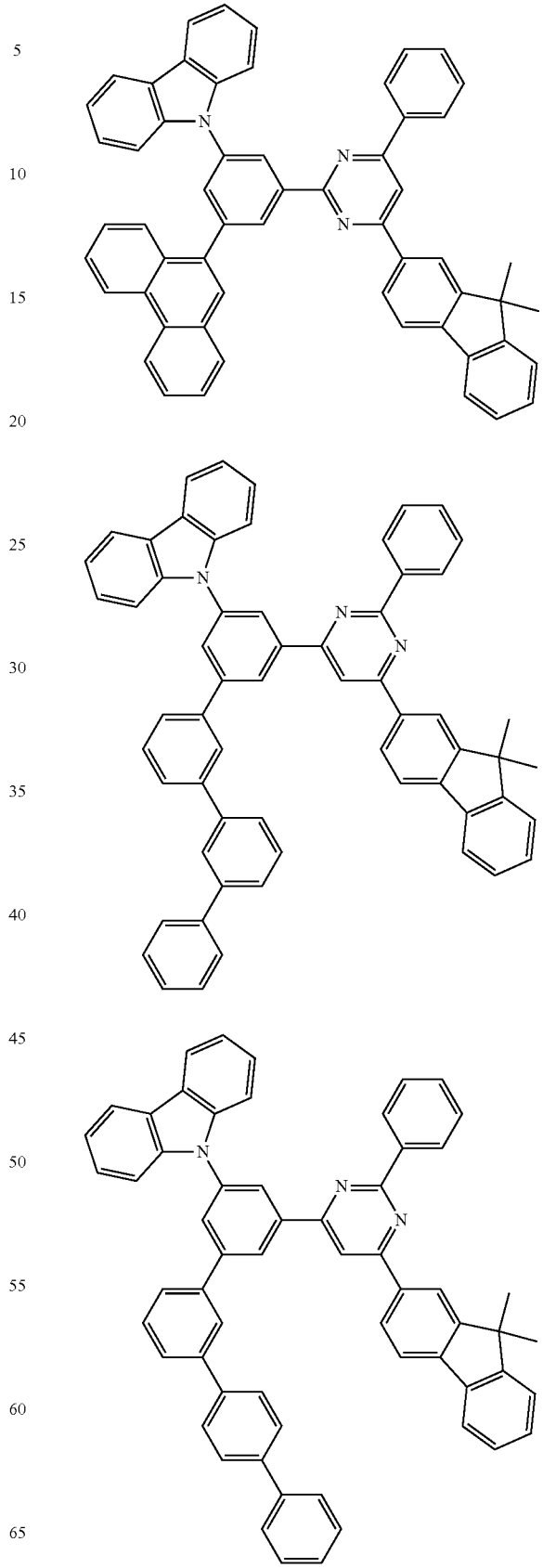

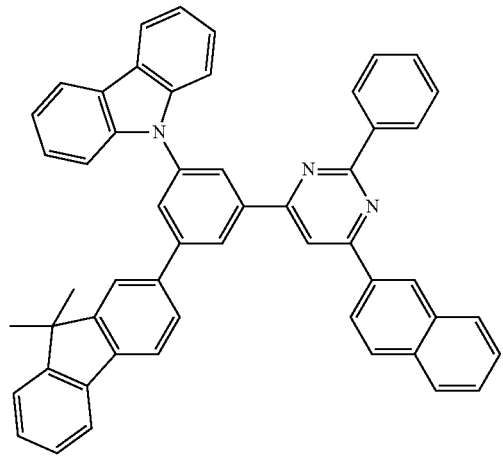
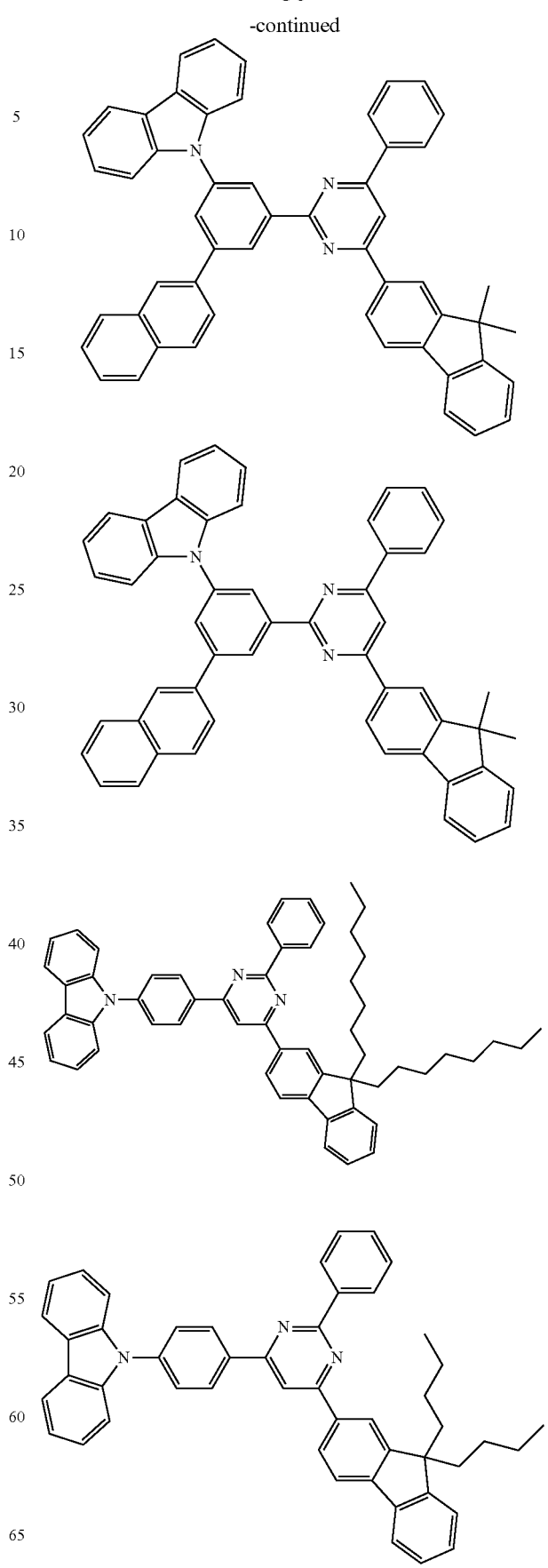

81
-continued
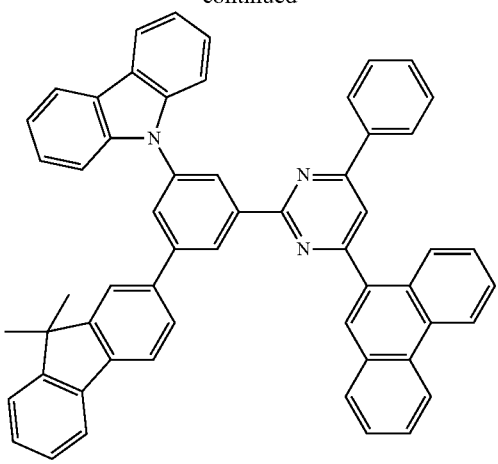
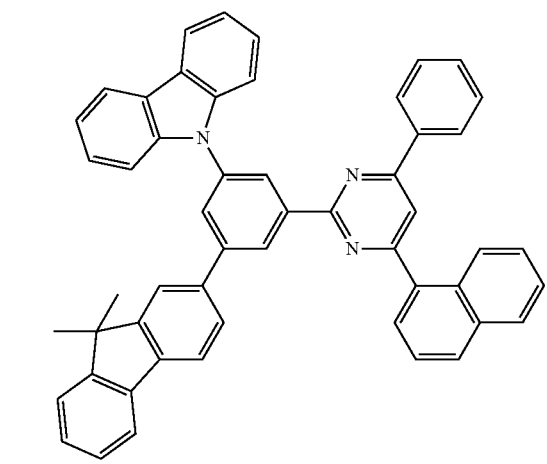
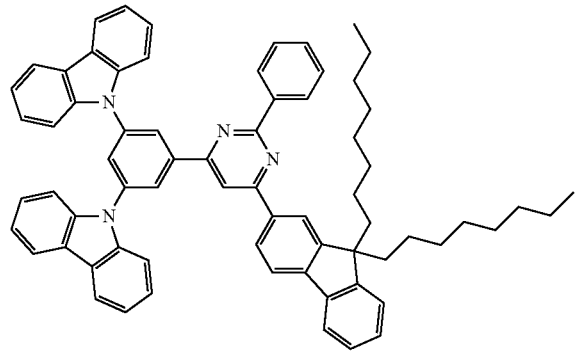
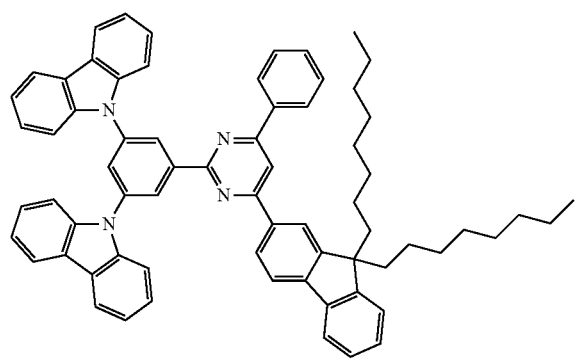
82
-continued
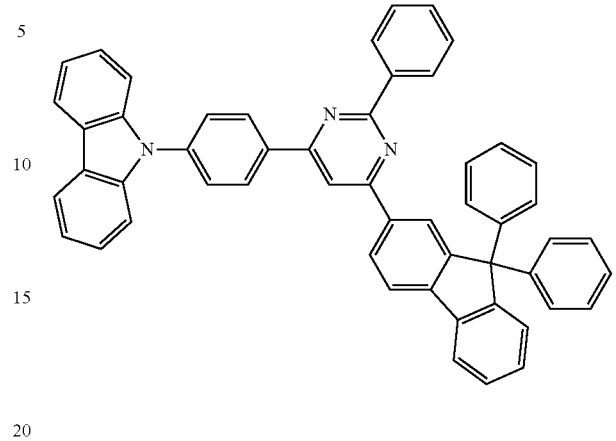
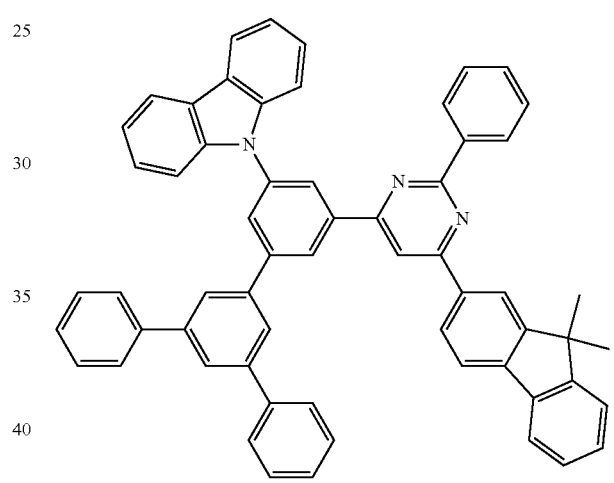
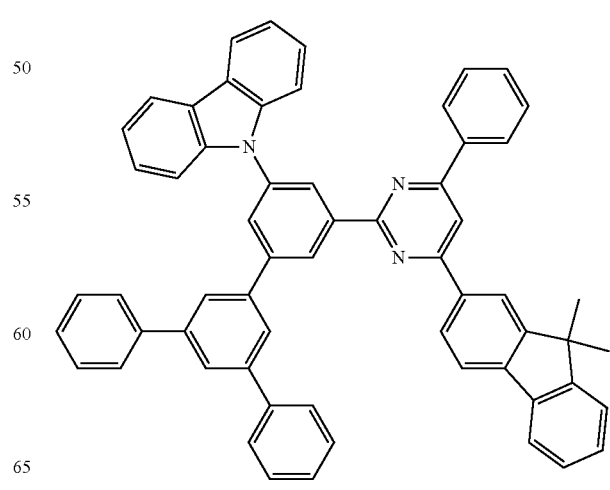

[Chemical Formula 26]
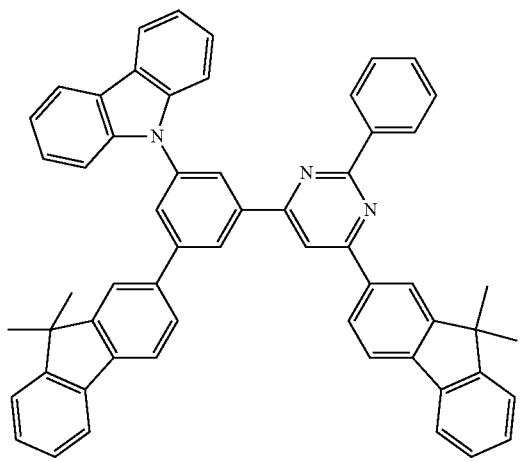
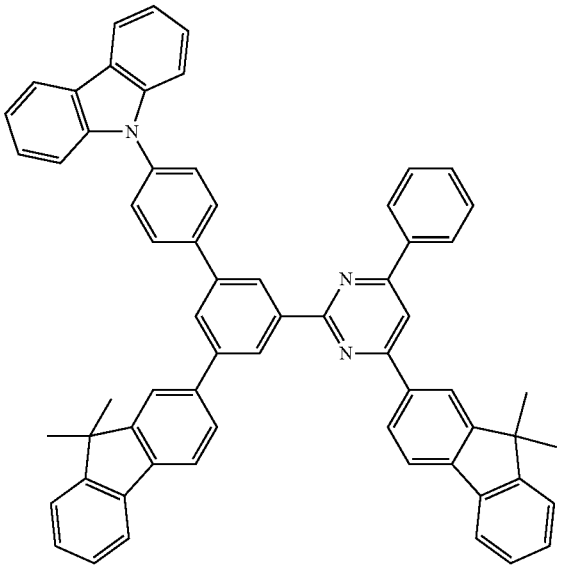
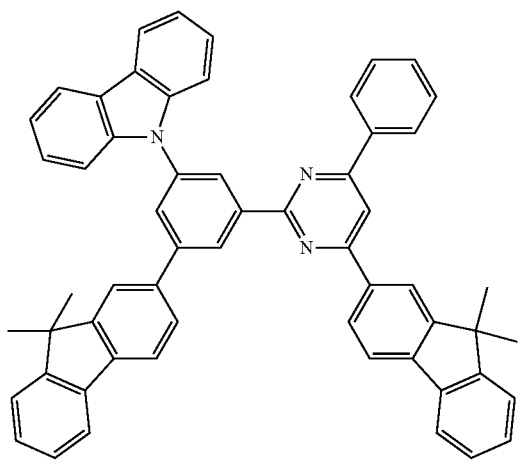
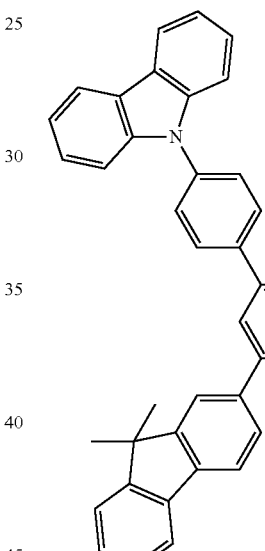
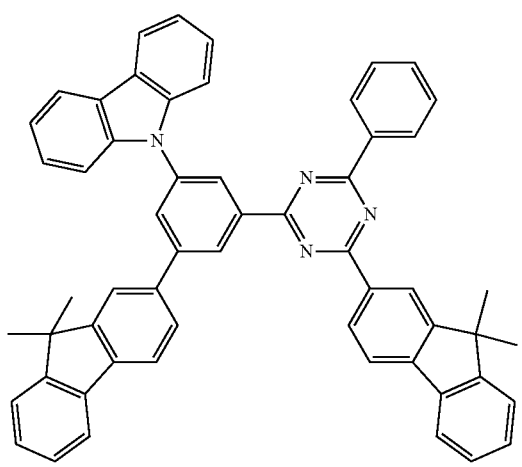
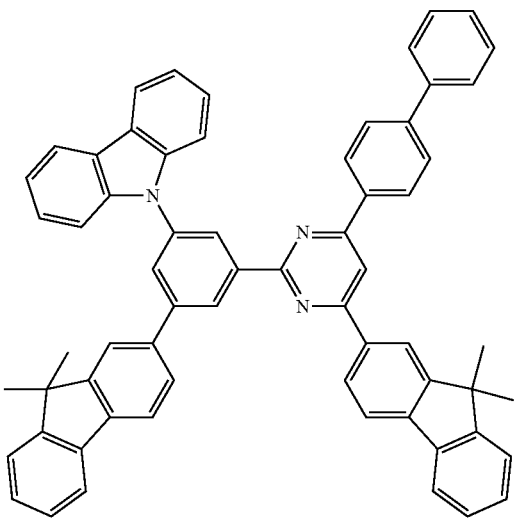

85
-continued
86
-continued
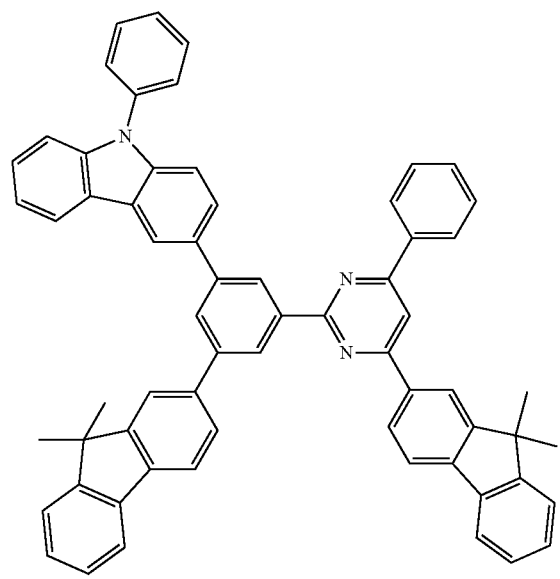
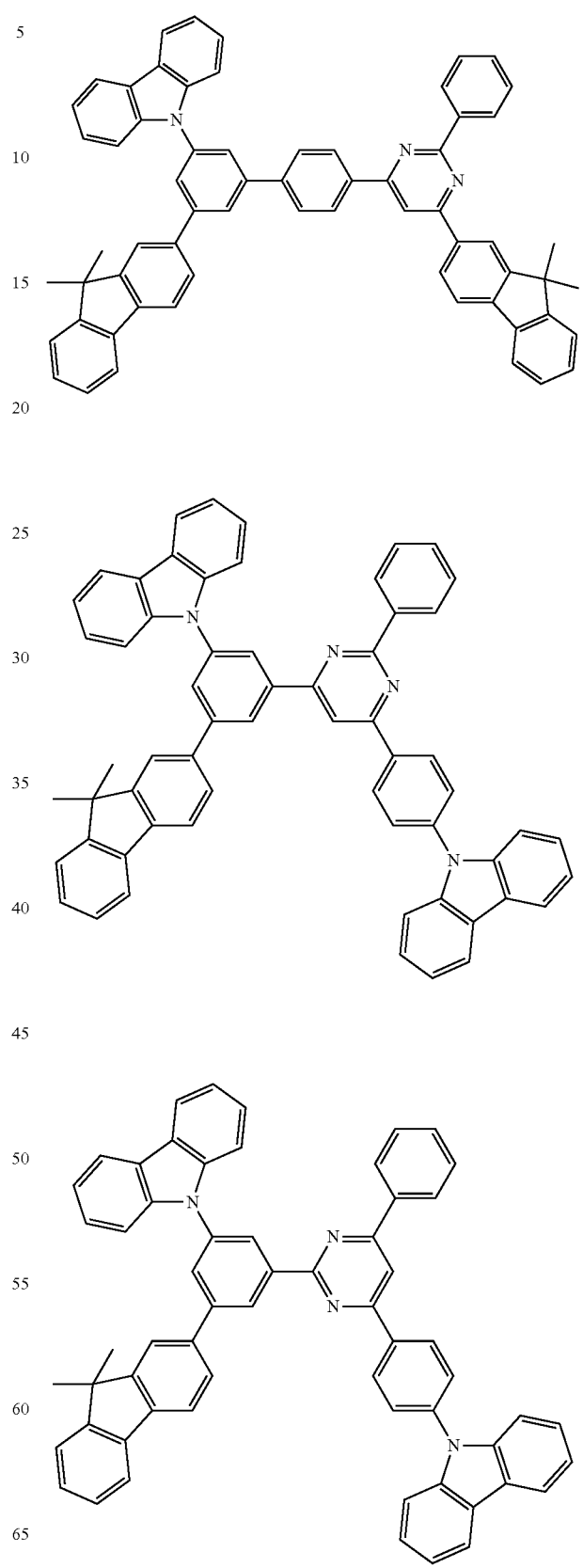

-continued

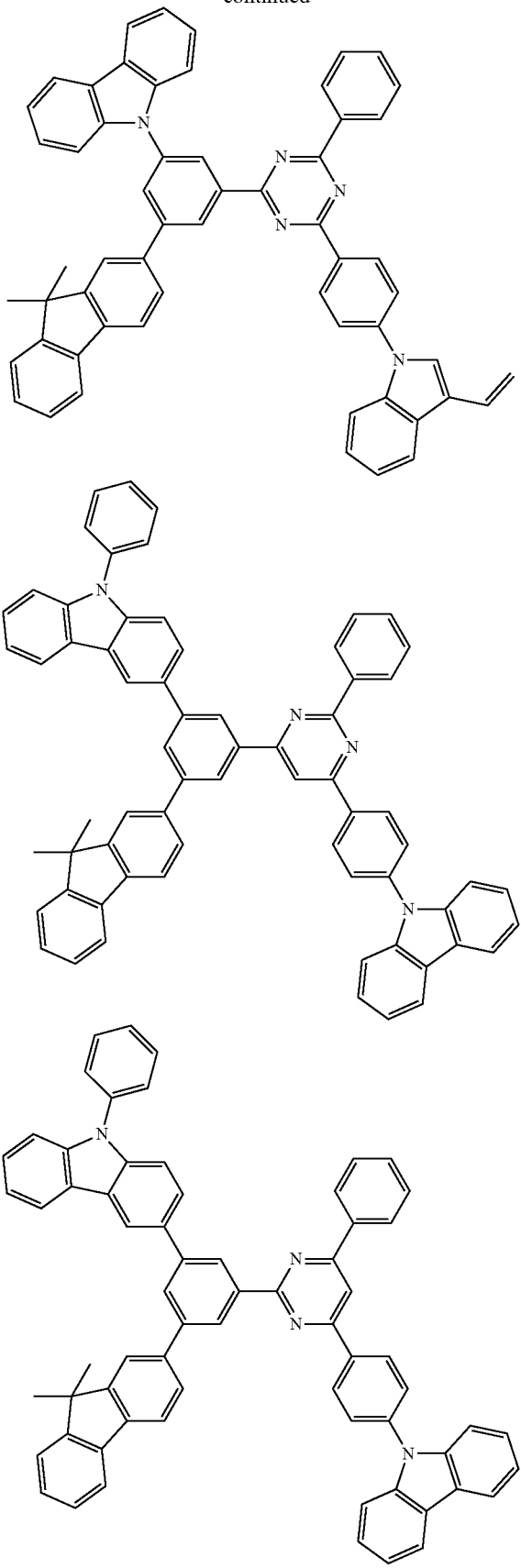

In the organic EL device according to this exemplary embodiment, the emitting layer preferably contains the fluorene-containing aromatic compound as a host material. In addition, the emitting layer is preferably formed of a host material and a phosphorescent material while the host material is the fluorene-containing aromatic compound.

The fluorene-containing aromatic compound may be a host material used with a phosphorescent material, or may be an electron transporting material used with a phosphorescent material. The fluorene-containing aromatic compound preferably has an excited triplet energy of 2.2 eV to 3.2 eV, more preferably 2.4 eV to 3.2 eV.

The organic EL device according to this exemplary embodiment may preferably include an electron transporting layer that contains the organic-EL-device material according to this exemplary embodiment.

The organic EL device according to this exemplary embodiment may preferably include at least one of the electron transporting layer and the hole blocking layer that contains the organic-EL-device material according to this exemplary embodiment.

The organic EL device according to this exemplary embodiment may preferably include the hole transporting layer (hole injecting layer) that contains the organic-EL-device material according to this exemplary embodiment.

Phosphorescent Material

According to this exemplary embodiment, the phosphorescent material preferably contains a metal complex, and the metal complex preferably has a metal atom selected from Ir, Pt, Os, Au, Cu, Re and Ru, and a ligand. Particularly, the ligand preferably has an ortho-metal bond.

The phosphorescent material is preferably a compound containing a metal selected from iridium (Ir), osmium (Os) and platinum (Pt) because such a compound, which exhibits high phosphorescence quantum yield, can further enhance external quantum efficiency of the emitting device. The phosphorescent material is more preferably a metal complex such as an iridium complex, osmium complex or platinum complex, among which an iridium complex and platinum complex are more preferable and ortho metalation of an iridium complex is the most preferable.

Examples of such a preferable metal complex are shown below.

[Chemical Formula 27]

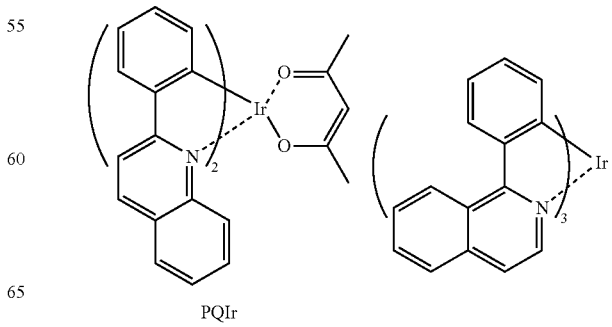

PQIr

89
-continued
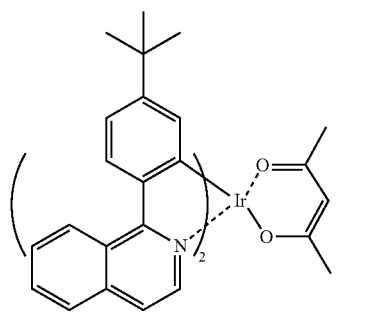
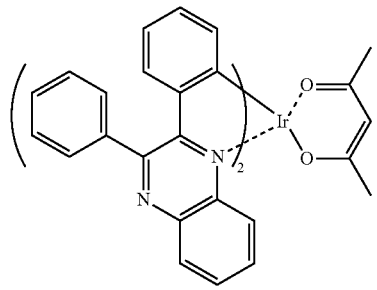
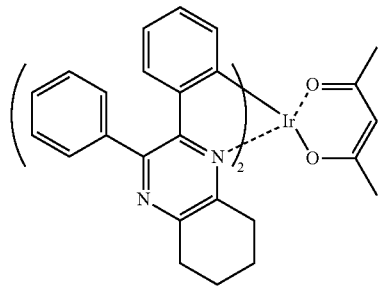
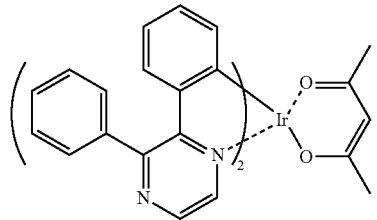
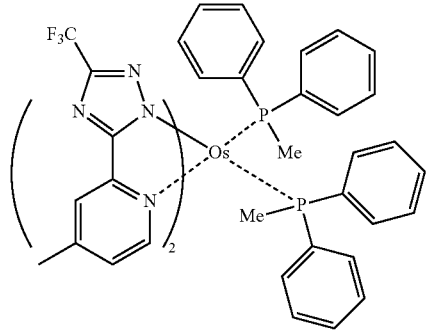
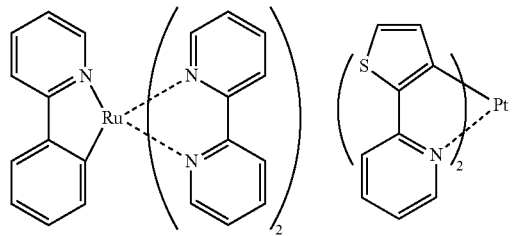
90
-continued
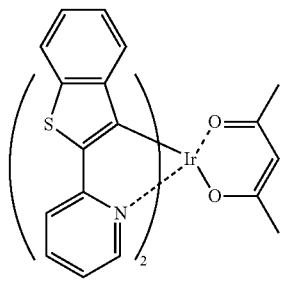
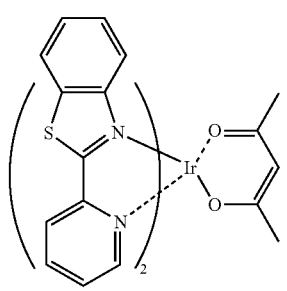
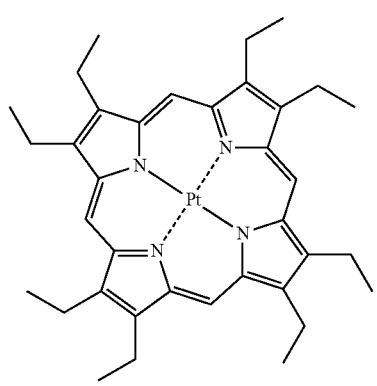
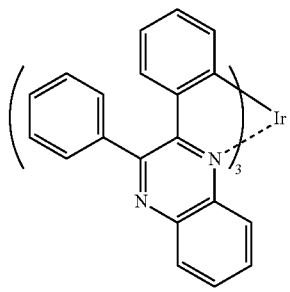
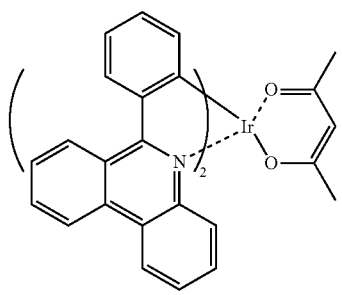

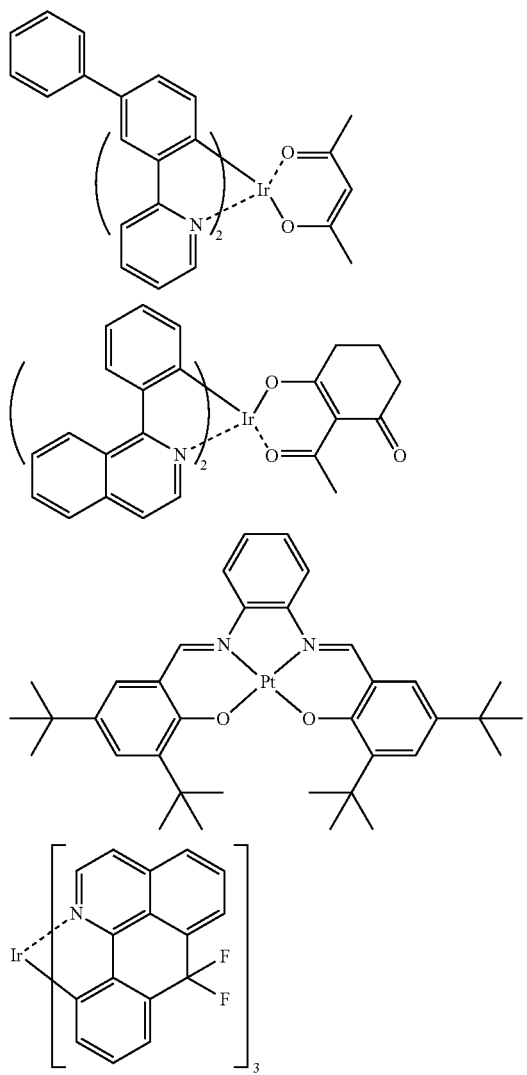
[Chemical Formula 28]
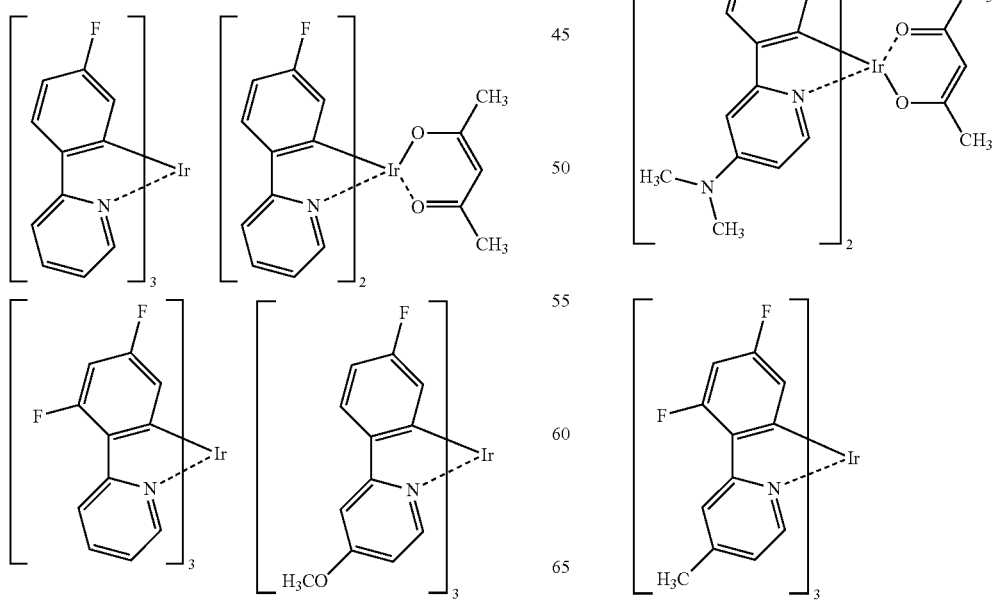

93
-continued
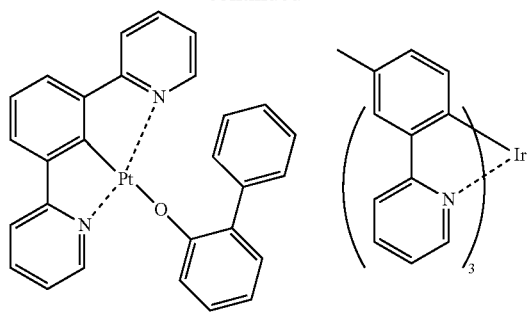
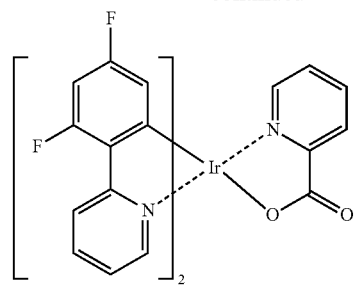
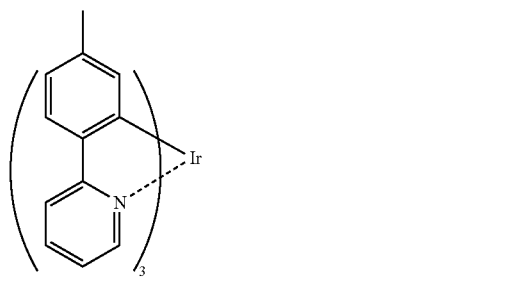
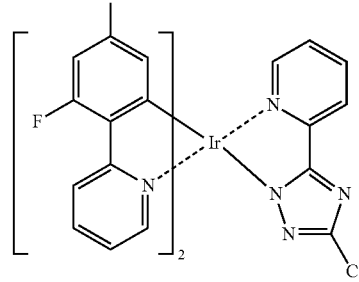
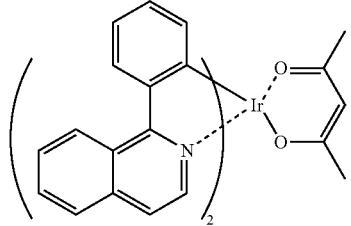
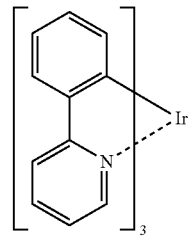
Ir (ppy)₃
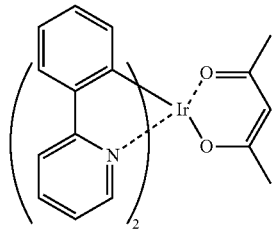
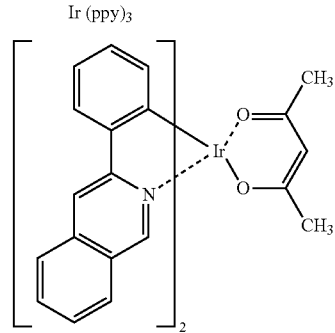
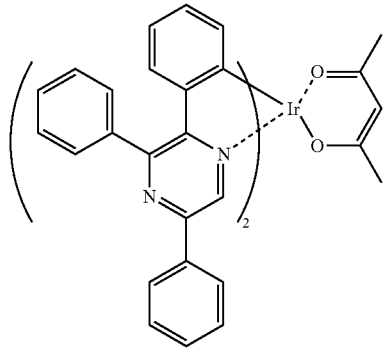
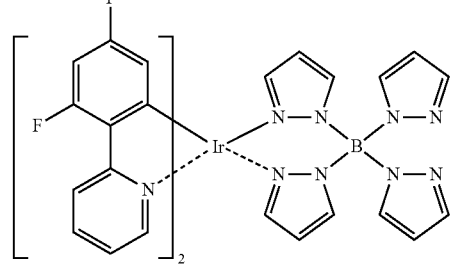
[Chemical Formula 29]
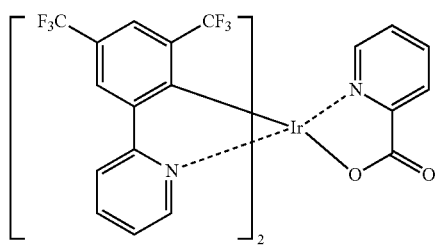
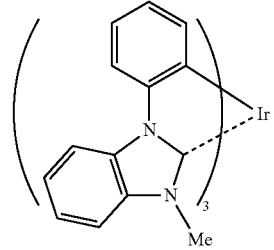
94
-continued

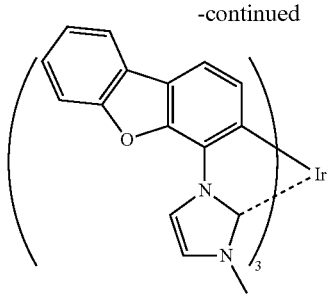
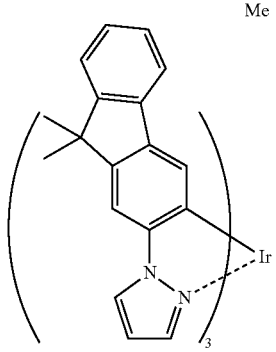
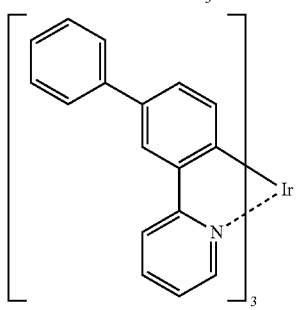
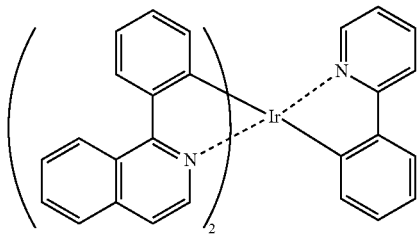
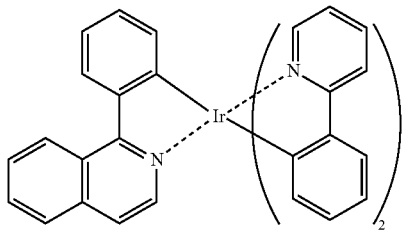
[Chemical Formula 30]
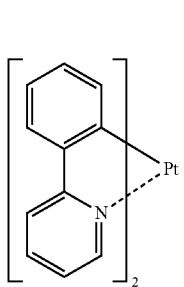
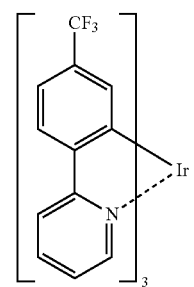
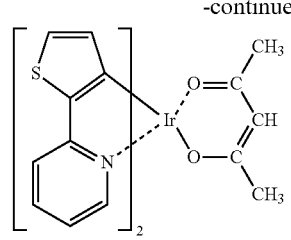
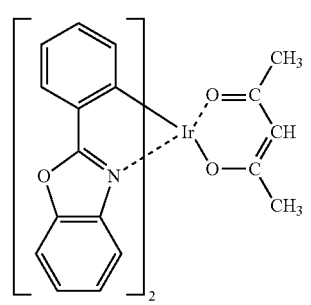
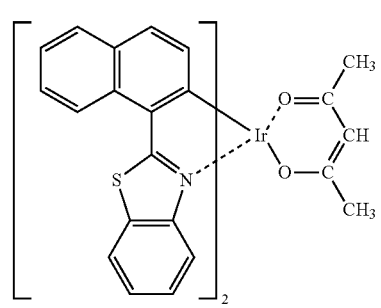
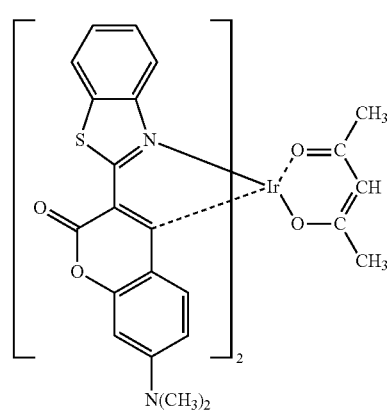
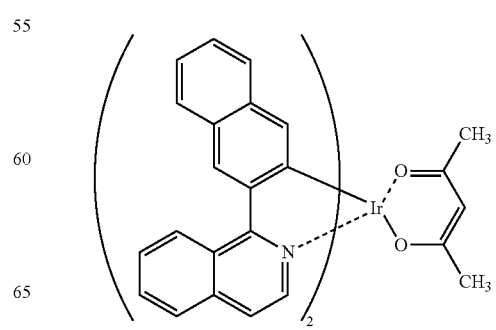

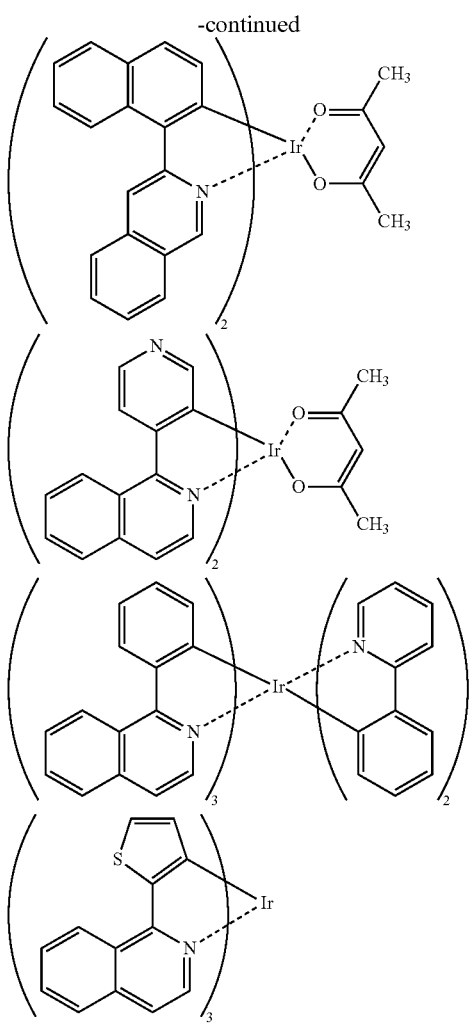

According to this exemplary embodiment, at least one of the phosphorescent material contained in the emitting layer preferably emits light with the maximum wavelength of 450 nm to 720 nm.

By doping the phosphorescent material (phosphorescent dopant) having such an emission wavelength to the specific host material used in this exemplary embodiment to form the emitting layer, the organic EL device can exhibit high efficiency.

Reduction-Causing Dopant

In the organic EL device according to this exemplary embodiment, a reductive dopant may be preferably contained in an interfacial region between the cathode and the organic thin-film layer.

With this structure, the organic EL device can emit light with enhanced luminance intensity and have a longer lifetime.

The reduction-causing dopant may be at least one compound selected from a group of an alkali metal, alkali metal complex, alkali metal compound, alkali earth metal, alkali earth metal complex, alkali earth metal complex compound, rare-earth metal, rare-earth metal complex, a rare-earth metal compound and the like.

Examples of the alkali metal are Na (work function: 2.36 eV), K (work function: 2.28 eV), Rb (work function: 2.16 eV), and Cs (work function: 1.95 eV), among which the alkali metal having a work function of 2.9 eV or less is particularly preferable. Among the above, the reduction-causing dopant is preferably K, Rb or Cs, more preferably Rb or Cs, the most preferably Cs.

Examples of the alkali earth metal are Ca (work function: 2.9 eV), Sr (work function: 2.0 eV to 2.5 eV), and Ba (work function: 2.52 eV), among which the alkali earth metal having a work function of 2.9 eV or less is particularly preferable.

Examples of the rare-earth metal are Sc, Y, Ce, Tb, and Yb, among which the rare-earth metal having a work function of 2.9 eV or less is particularly preferable.

Since the above preferred metals have particularly high reducibility, addition of a relatively small amount of the metals to an electron injecting zone can enhance luminance intensity and lifetime of the organic EL device.

Examples of the alkali metal compound are an alkali oxide such as $Li_2O$, $Cs_2O$ or $K_2O$, and an alkali halogen compound such as LiF, NaF, CsF or KF, among which LiF, $Li_2O$ and NaF are preferable.

Examples of the alkali earth metal compound are BaO, SrO, CaO, and a mixture thereof such as $Ba_xSr_{1-x}O$ ($0<x<1$) or $Ba_xCa_{1-x}O$ ($0<x<1$), among which BaO, SrO and CaO are preferable.

Examples of the rare-earth metal compound are $YbF_3$, $ScF_3$, $ScO_3$, $Y_2O_3$, $Ce_2O_3$, $GdF_3$, $TbF_3$ and the like, among which $YbF_3$, $ScF_3$ and $TbF_3$ are preferable.

The alkali metal complex, alkali earth metal complex and rare-earth metal complex are subject to no limitation as long as they contain at least one metal ion of an alkali metal ion, an alkali earth metal ion and a rare-earth metal ion. The ligand is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The reduction-causing dopant is added to preferably form a layer or an island pattern in the interfacial region. The layer of the reduction-causing dopant or the island pattern of the reduction-causing dopant is preferably formed by depositing the reduction-causing dopant by resistance heating deposition while an emitting material for forming the interfacial region or an organic substance as an electron-injecting material are simultaneously deposited, so that the reduction-causing dopant is dispersed in the organic substance. Dispersion concentration at which the reduction-causing dopant is dispersed in the organic substance is a mole ratio (organic substance to reduction-causing dopant) of 100:1 to 1:100, preferably 5:1 to 1:5.

When the reduction-causing dopant forms the layer, the emitting material or the electron injecting material for forming the organic layer of the interfacial region is initially layered, and the reduction-causing dopant is subsequently deposited singularly thereon by resistance heating deposition to form a preferably 0.1 nm- to 15 nm-thick layer.

When the reduction-causing dopant forms the island pattern, the emitting material or the electron injecting material for forming the organic layer of the interfacial region is initially formed in an island shape, and the reduction-causing dopant is subsequently deposited singularly thereon by resistance heating deposition to form a preferably 0.05 nm- to 1 nm-thick island shape.

A ratio of the main component to the reduction-causing dopant in the organic EL device according to this exemplary embodiment is preferably a mole ratio (main component to reductive dopant) of 5:1 to 1:5, more preferably 2:1 to 1:2.

Electron Injecting Layer and Electron Transporting Layer

The electron injecting layer or the electron transporting layer, which aids injection of the electrons into the emitting layer, has a large electron mobility. The electron injecting layer is provided for adjusting energy level, by which, for instance, sudden changes in the energy level can be reduced.

The organic EL device according to this exemplary embodiment preferably includes the electron injecting layer between the emitting layer and the cathode, and the electron injecting layer preferably contains a nitrogen-containing cyclic derivative as a main component. The electron injecting layer may serve as an electron transporting layer.

It should be noted that "as a main component" means that the nitrogen-containing cyclic derivative is contained in the electron injecting layer at a content of 50 mass % or more.

A preferable example of an electron transporting material for forming the electron injecting layer is an aromatic heterocyclic compound having at least one heteroatom in a molecule. Particularly, a nitrogen-containing cyclic derivative is preferable. The nitrogen-containing cyclic derivative is preferably an aromatic ring having a nitrogen-containing six-membered or five-membered ring skeleton, or a fused aromatic cyclic compound having a nitrogen-containing six-membered or five-membered ring skeleton.

The nitrogen-containing cyclic derivative is preferably exemplified by a nitrogen-containing cyclic metal chelate complex represented by the following formula (A).

[Chemical Formula 31]

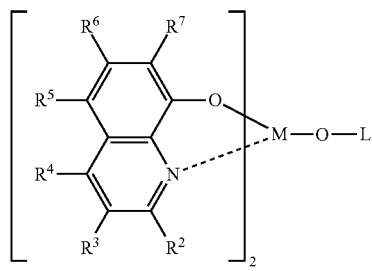

(A)

$R^2$ to $R^7$ in the formula (A) each independently represent a hydrogen atom, halogen atom, oxy group, amino group, hydrocarbon group having 1 to 40 carbon atoms, alkoxy group, aryloxy group, alkoxycarbonyl group, or heterocyclic group. These groups may be substituted or unsubstituted.

Examples of the halogen atom include fluorine, chlorine, bromine, and iodine. In addition, examples of the substituted or unsubstituted amino group include an alkylamino group, an arylamino group, and an aralkylamino group.

The alkoxycarbonyl group is represented by —COOY'. Examples of Y' are the same as the examples of the alkyl group. The alkylamino group and the aralkylamino group are represented by —NQ$^1$Q$^2$. Examples for each of Q$^1$ and Q$^2$ are the same as the examples described in relation to the alkyl group and the aralkyl group, and preferred examples for each of Q$^1$ and Q$^2$ are also the same as those described in relation to the alkyl group and the aralkyl group. Either one of Q$^1$ and Q$^2$ may be a hydrogen atom.

The arylamino group is represented by —NAr$^1$Ar$^2$. Examples for each of Ar$^1$ and Ar$^2$ are the same as the examples described in relation to the non-fused aryl group and the fused aryl group. Either one of Ar$^1$ and Ar$^2$ may be a hydrogen atom.

M represents aluminum (Al), gallium (Ga) or indium (In), among which In is preferable.

L in the formula (A) represents a group represented by a formula (A') or (A") below.

[Chemical Formula 32]

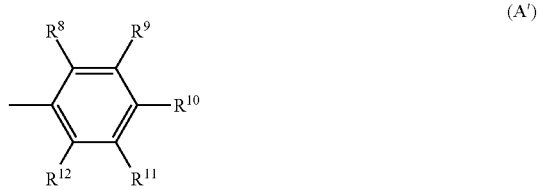

(A')

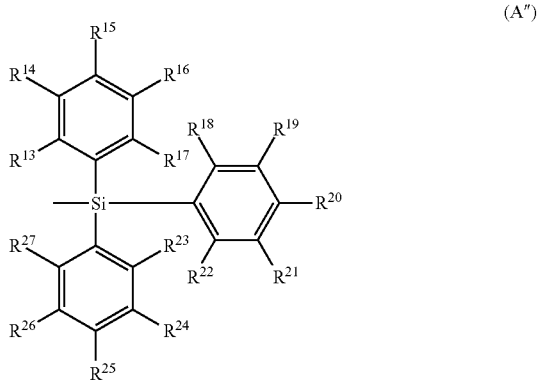

(A")

In the formula (A'), $R^8$ to $R^{12}$ each independently represent a hydrogen atom or a substituted or unsubstituted hydrocarbon group having 1 to 40 carbon atoms. Adjacent groups may form a cyclic structure. In the formula (A"), $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulae (A') and (A") are the same as those of $R^2$ to $R^7$.

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group, and a diphenylpropane-4,4'-diyl group.

In the exemplary embodiment of the invention, the aromatic compound represented by the formulae (1) and (3) to (5) is preferably contained as the electron transporting layer.

As an electron transporting compound for the electron injecting layer or the electron transporting layer, 8-hydroxyquinoline or a metal complex of its derivative, an oxadiazole derivative, and a nitrogen-containing heterocyclic derivative are preferable. A specific example of the 8-hydroxyquinoline or the metal complex of its derivative is a metal chelate oxinoid compound containing a chelate of oxine (typically 8-quinolinol or 8-hydroxyquinoline). For instance, tris(8-quinolinol)aluminum can be used. Examples of the oxadiazole derivative are as follows.

[Chemical Formula 33]

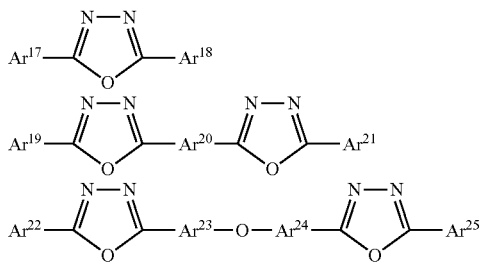

In the formula, $Ar^{17}$, $Ar^{18}$, $Ar^{19}$, $Ar^{21}$, $Ar^{22}$ and $Ar^{25}$ each represent a substituted or unsubstituted aryl group. $Ar^{17}$, $Ar^{19}$ and $Ar^{22}$ may be the same as or different from $Ar^{18}$, $Ar^{21}$ and $Ar^{25}$ respectively. $Ar^{20}$, $Ar^{23}$ and $Ar^{24}$ each represent a substituted or unsubstituted arylene group. $Ar^{23}$ and $Ar^{24}$ may be mutually the same or different.

Examples of the arylene group are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group.

Such an electron transporting compound is preferably an electron transporting compound that can be favorably formed into a thin film(s). Examples of the electron transporting compound are as follows.

[Chemical Formula 35]

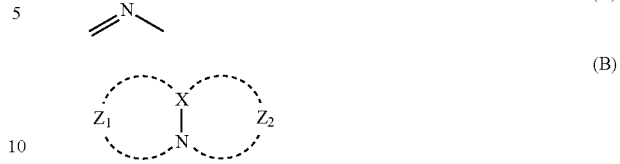

(A)

(B)

In the formula (B), X represents a carbon atom or a nitrogen atom. $Z_1$ and $Z_2$ each independently represent an atom group from which a nitrogen-containing heterocycle can be formed.

Preferably, the nitrogen-containing heterocyclic derivative is an organic compound having a nitrogen-containing aromatic polycyclic group having a five-membered ring or six-membered ring. Further, when the nitrogen-containing heterocyclic derivative is such a nitrogen-containing aromatic polycyclic group that contains plural nitrogen atoms, the nitrogen-containing heterocyclic derivative is preferably a nitrogen-containing aromatic polycyclic organic compound having a skeleton formed by a combination of the skeletons respectively represented by the formulae (A) and (B), or by a combination of the skeletons respectively represented by the formulae (A) and (C).

[Chemical Formula 34]

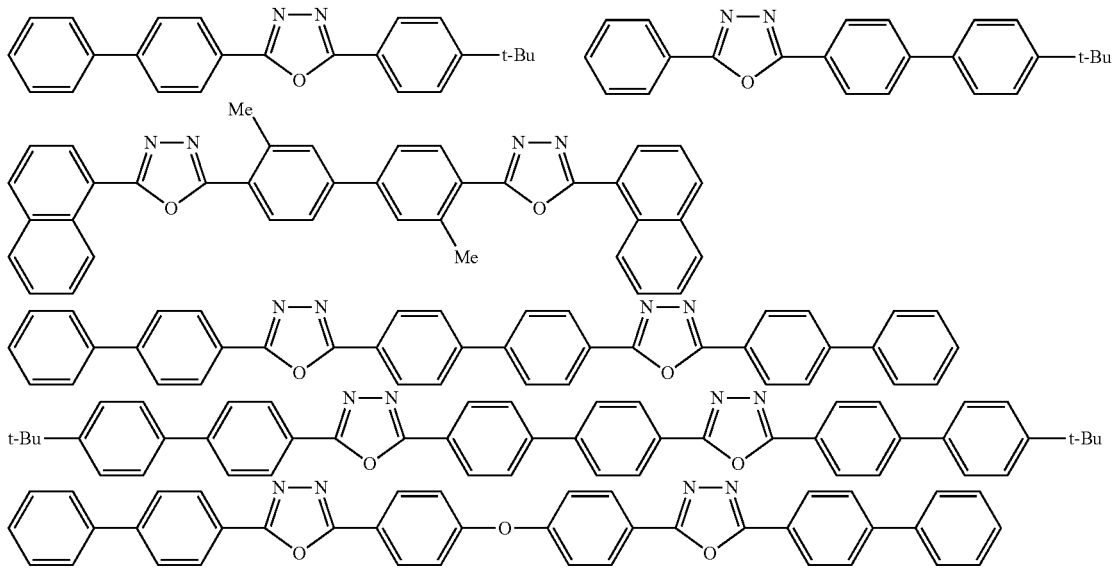

An example of the nitrogen-containing heterocyclic derivative as the electron transporting compound is a nitrogen-containing compound that is not a metal complex, the derivative being formed of an organic compound represented by one of the following general formulae. Examples of the nitrogen-containing heterocyclic derivative are a five-membered ring or six-membered ring derivative having a skeleton represented by the following formula (A) and a derivative having a structure represented by the following formula (B).

[Chemical Formula 36]

(C)

A nitrogen-containing group of the nitrogen-containing aromatic polycyclic organic compound is selected from nitrogen-containing heterocyclic groups respectively represented by the following general formulae.

[Chemical Formula 37]

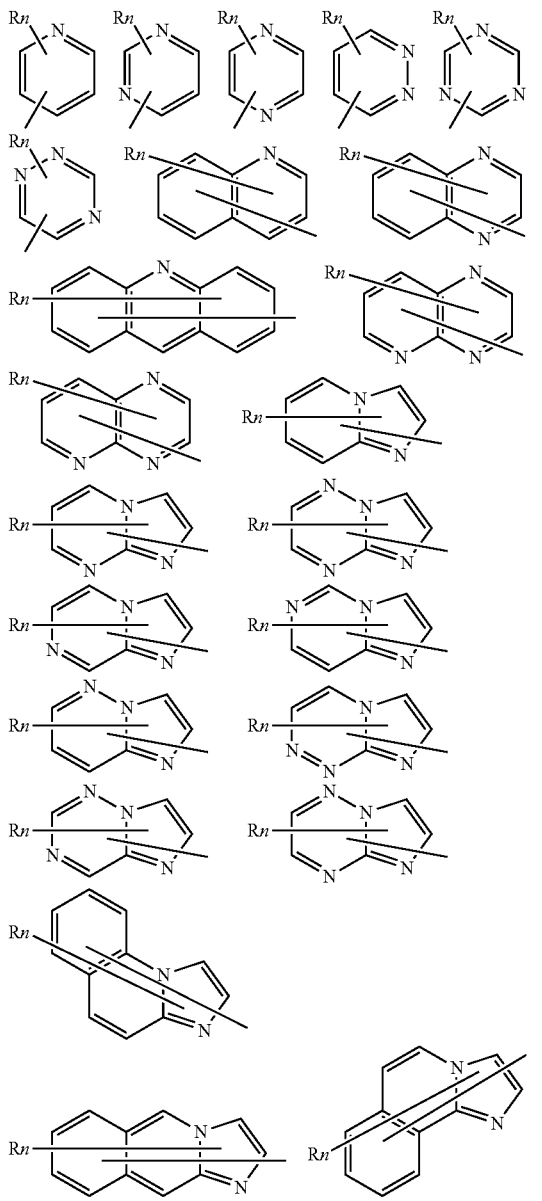

the formulae: R represents an aryl group having 6 to 40 carbon atoms, heteroaryl group having 3 to 40 carbon atoms, alkyl group having 1 to 20 carbon atoms or alkoxy group having 1 to 20 carbon atoms; and n represents an integer in a range of 0 to 5. When n is an integer of 2 or more, plural R may be mutually the same or different.

A preferable specific compound is a nitrogen-containing heterocyclic derivative represented by the following formula.

HAr-L$^1$-Ar$^1$—Ar$^2$

In the formula: HAr represents a substituted or unsubstituted nitrogen-containing heterocycle having 3 to 40 carbon atoms; L$^1$ represents a single bond, substituted or unsubstituted arylene group having 6 to 40 carbon atoms, or substituted or unsubstituted heteroarylene group having 3 to 40 carbon atoms; Ar$^1$ represents a substituted or unsubstituted divalent aromatic hydrocarbon group having 6 to 40 carbon atoms; and Ar$^e$ represents a substituted or unsubstituted aryl group having 6 to 40 carbon atoms, or substituted or unsubstituted heteroaryl group having 3 to 40 carbon atoms.

HAr is exemplarily selected from the following group.

[Chemical Formula 38]

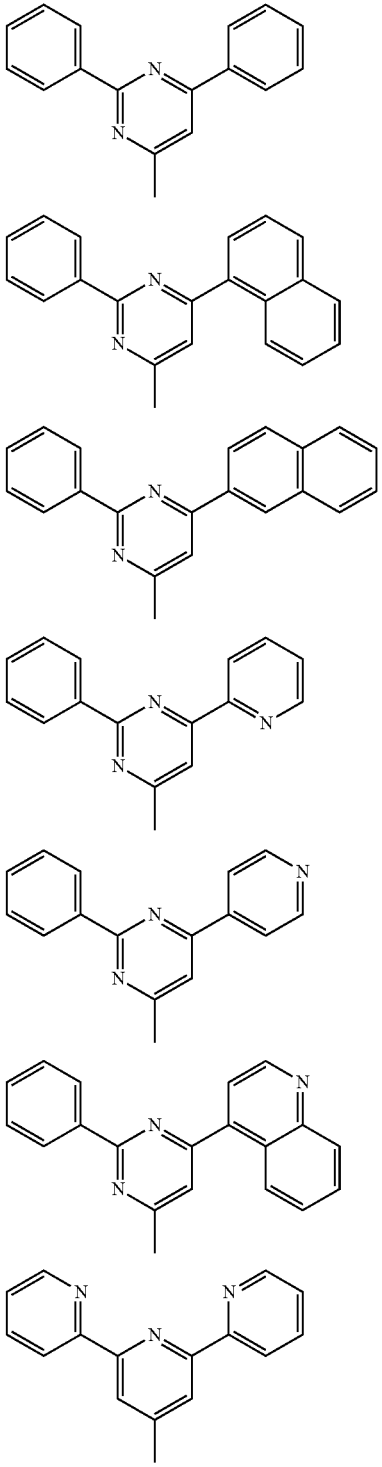

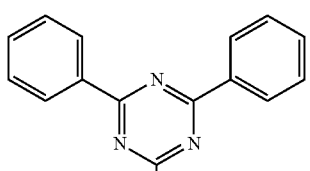
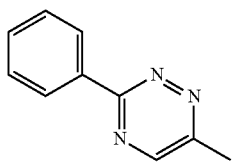
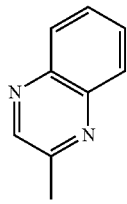
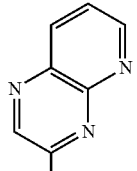
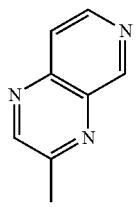
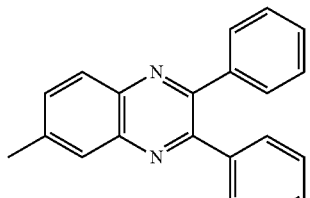
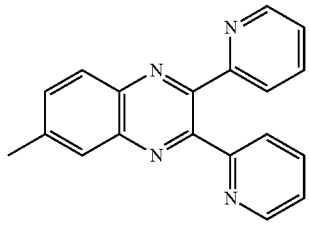
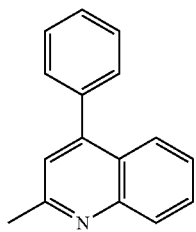

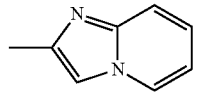
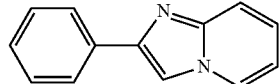
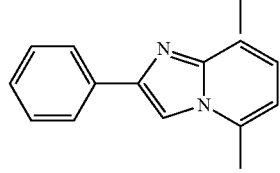
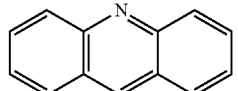

$L^1$ is exemplarily selected from the following group.

[Chemical Formula 39]

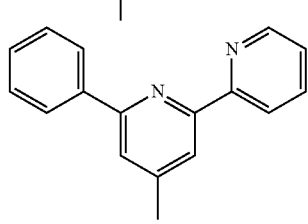

$Ar^1$ is exemplarily selected from the following arylanthranil group.

[Chemical Formula 40]

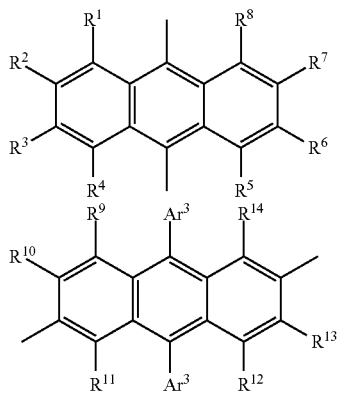

In the formula: $R^1$ to $R^{14}$ each independently represent a hydrogen atom, halogen atom, alkyl group having 1 to 20 carbon atoms, alkoxy group having 1 to 20 carbon atoms, aryloxy group having 6 to 40 carbon atoms, substituted or unsubstituted aryl group having 6 to 40 carbon atoms, or heteroaryl group having 3 to 40 carbon atoms; and $Ar^3$ represents a substituted or unsubstituted aryl group having 6 to 40 carbon atoms, or a heteroaryl group having 3 to 40 carbon atoms.

All of $R^1$ to $R^8$ of a nitrogen-containing heterocyclic derivative may be hydrogen atoms.

$Ar^2$ is exemplarily selected from the following group.

[Chemical Formula 41]

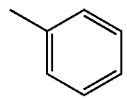

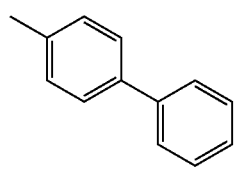

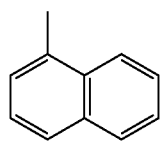

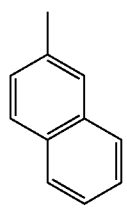

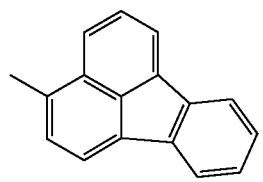

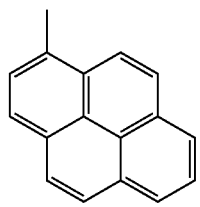

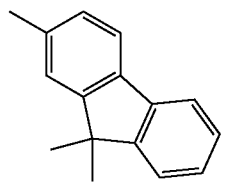

Other than the above, the following compound (see JP-A-9-3448) can be favorably used for the nitrogen-containing aromatic polycyclic organic compound as the electron transporting compound.

[Chemical Formula 42]

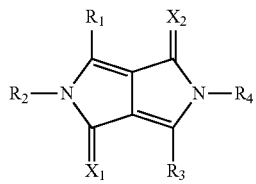

In the formula: $R_1$ to $R_4$ each independently represent a hydrogen atom, substituted or unsubstituted aliphatic group, substituted or unsubstituted alicyclic group, substituted or unsubstituted carbocyclic aromatic cyclic group, or substituted or unsubstituted heterocyclic group; and $X_1$ and $X_2$ each independently represent an oxygen atom, sulfur atom or dicyanomethylene group.

The following compound (see JP-A-2000-173774) can also be favorably used for the electron transporting compound.

[Chemical Formula 43]

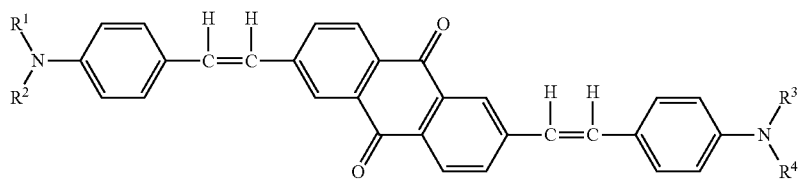

In the formula, $R^1$, $R^2$, $R^3$ and $R^4$, which may be mutually the same or different, each represent an aryl group represented by the following formula.

[Chemical Formula 44]

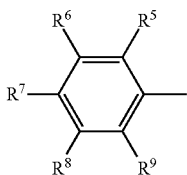

In the formula, $R^5$, $R^6$, $R^7$, $R^8$ and $R^9$, which may be mutually the same or different, each represent a hydrogen atom, saturated or unsaturated alkoxy group, alkyl group, amino group or alkylamino group. At least one of $R^5$, $R^6$, $R^7$, $R^8$ and $R^9$ represents a saturated or unsaturated alkoxy group, alkyl group, amino group or alkylamino group.

A polymer compound containing the nitrogen-containing heterocyclic group or a nitrogen-containing heterocyclic derivative may be used for the electron transporting compound.

The electron transporting layer preferably contains at least one of nitrogen-containing heterocycle derivatives respectively represented by the following formulae (201) to (203).

[Chemical Formula 45]

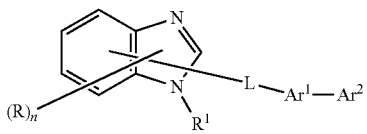  (201)

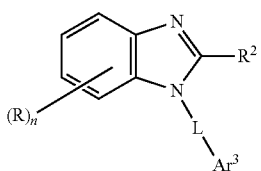  (202)

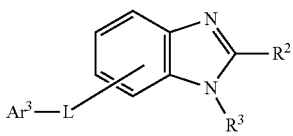  (203)

In the formulae (201) to (203), R represents a hydrogen atom, substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms. n represents an integer of 0 to 4. $R^1$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, or alkoxy group having 1 to 20 carbon atoms. $R^2$ and $R^3$ each independently represent a hydrogen atom, substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms. L represents a substituted or unsubstituted arylene group having 6 to 60 carbon atoms, substituted or unsubstituted pyridinylene group, substituted or unsubstituted quinolinylene group, or substituted or unsubstituted fluorenylene group. $Ar^1$ represents a substituted or unsubstituted arylene group having 6 to 60 carbon atoms, substituted or unsubstituted pyridinylene group, or substituted or unsubstituted quinolinylene group. $Ar^2$ represents substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms.

$Ar^3$ represents a substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, substituted or unsubstituted alkoxy group having 1 to 20 carbon atoms or a group represented by $-Ar^1-Ar^2$ ($Ar^1$ and $Ar^2$ may be the same as the above).

In the formulae (201) to (203), R represents a hydrogen atom, substituted or unsubstituted aryl group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms.

Although a thickness of the electron injecting layer or the electron transporting layer is subject to no limitation, the thickness is preferably 1 nm to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron injectability.

As the insulator, it is preferable to use at least one metal compound selected from the group consisting of an alkali metal chalcogenide, an alkali earth metal chalcogenide, a halogenide of alkali metal and a halogenide of alkali earth metal. When the electron injecting layer is formed from the alkali metal chalcogenide or the like, the electron injectability can preferably be further enhanced. Specifically, preferred examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferred examples of the halogenide of the alkali metal are LiF, NaF, KF, LiCl, KCl and NaCl. Preferred examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron injecting layer is preferably a microcrystalline or amorphous insulative film. When the electron injecting layer is formed of such insulative film, more uniform thin film can be formed, thereby reducing pixel defects such as a dark spot. Examples of such an inorganic compound are the alkali metal chalcogenide, alkali earth metal chalcogenide, halogenide of the alkali metal and halogenide of the alkali earth metal.

When the electron injecting layer contains such an insulator or semiconductor, a thickness thereof is preferably in a range of approximately 0.1 nm to 15 nm. The electron injecting layer according to this exemplary embodiment may preferably contain the above-described reduction-causing dopant.

Hole Injecting Layer and Hole Transporting Layer

The hole injecting layer or the hole transporting layer (including the hole injecting/transporting layer) may contain an aromatic amine compound such as an aromatic amine derivative represented by the following formula (I).

[Chemical Formula 46]

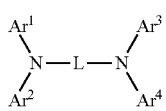

In the formula (I), $Ar^1$ to $Ar^4$ each represent a substituted or unsubstituted aryl group having 6 to 50 ring carbon atoms, substituted or unsubstituted heteroaryl group having 5 to 50 atoms for forming a ring, or a group formed by bonding the aryl group to the heteroaryl group.

Examples of the compound represented by the formula (I) are shown below. However, the compound represented by the formula (I) is not limited thereto.

[Chemical Formula 47]

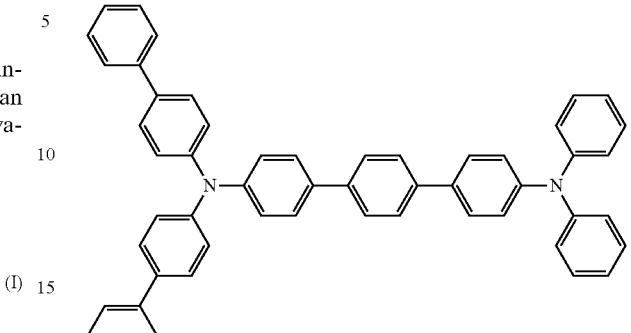

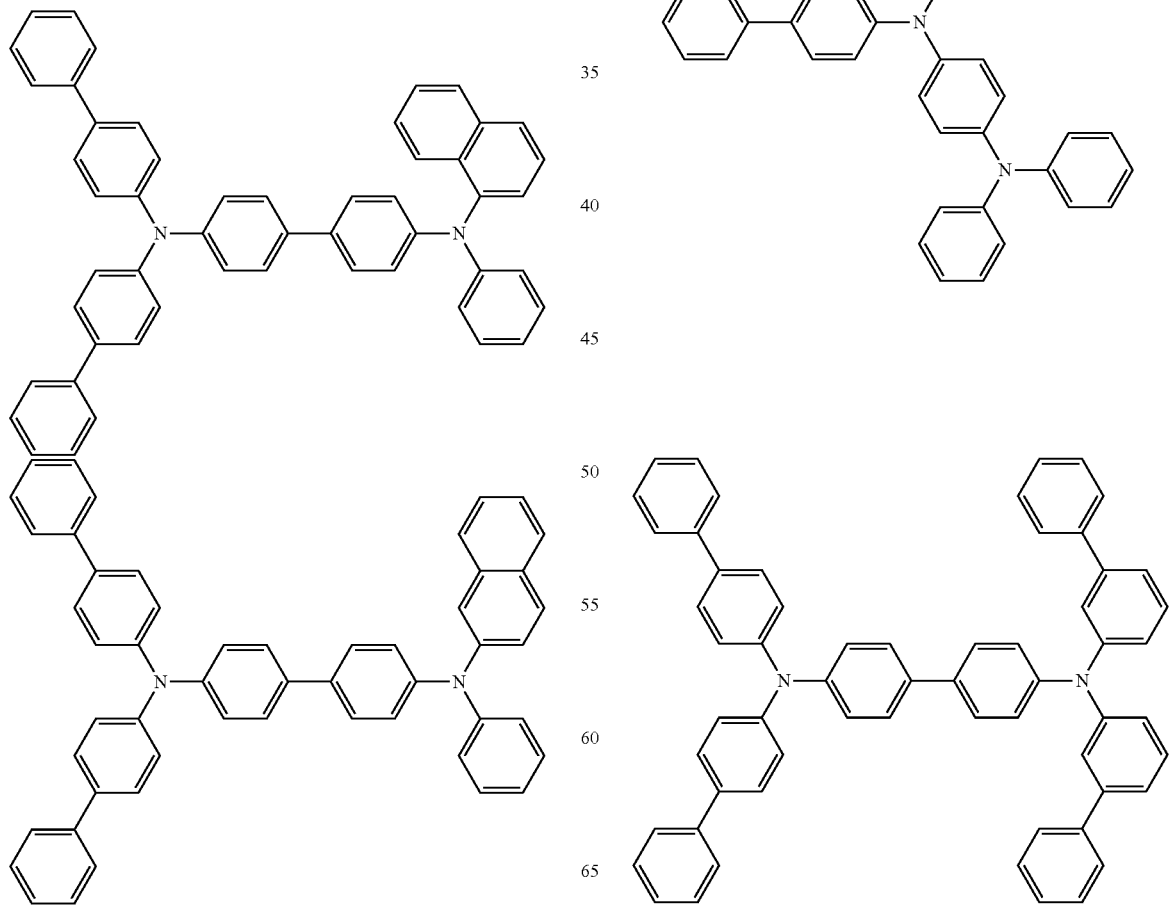

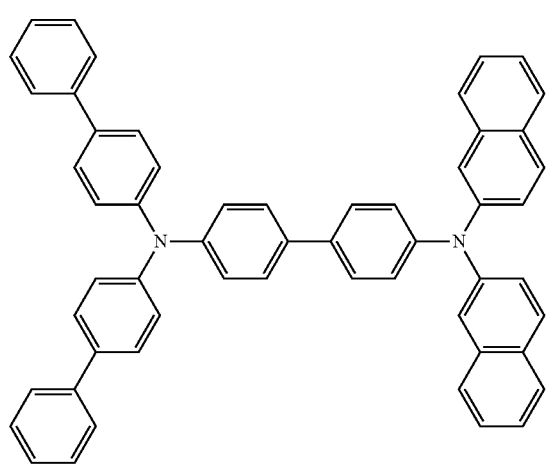
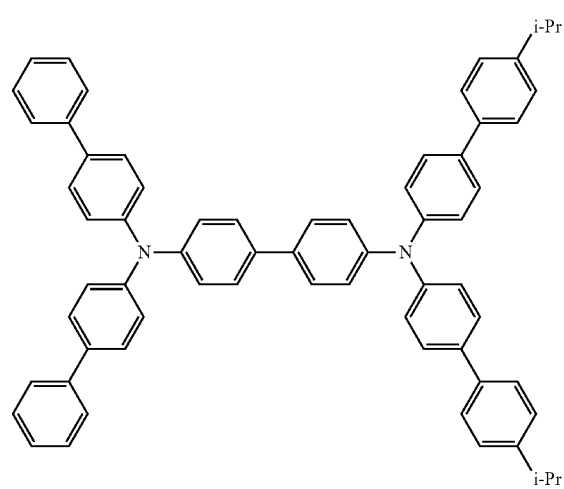
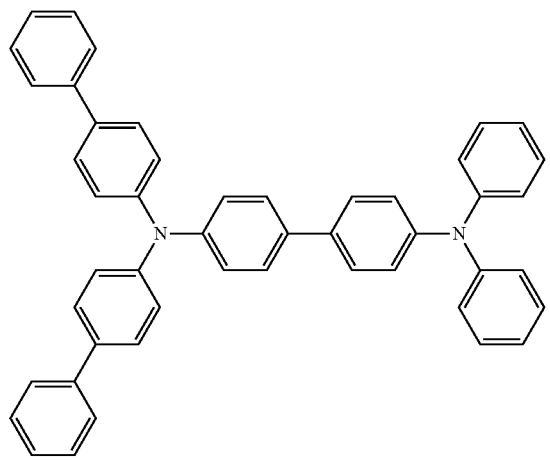
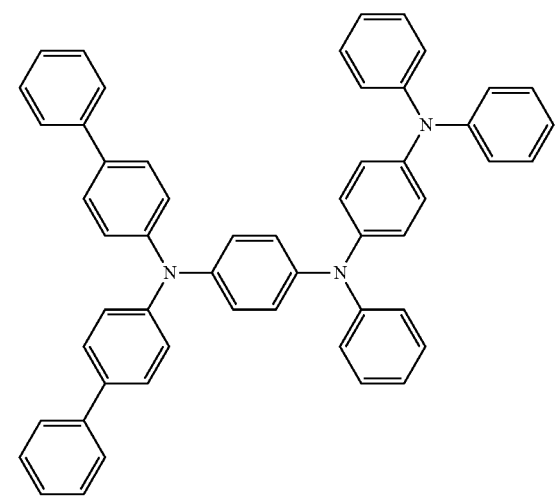
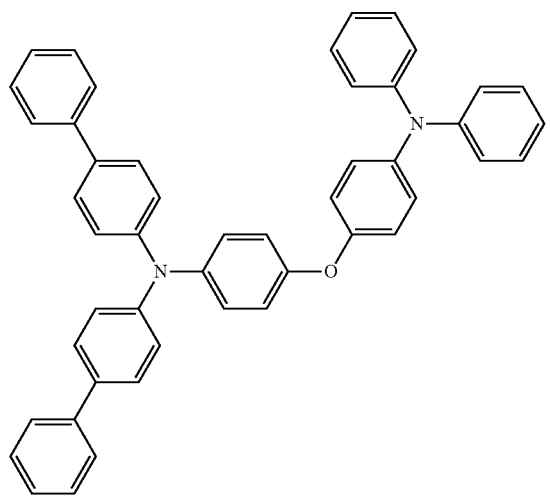

115
-continued
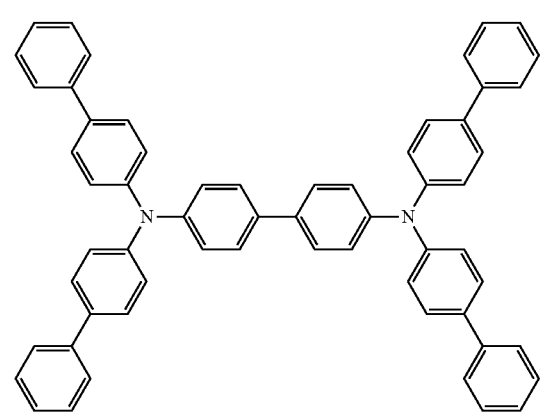
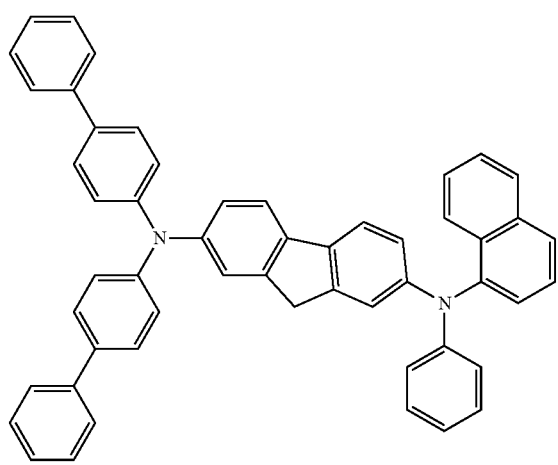
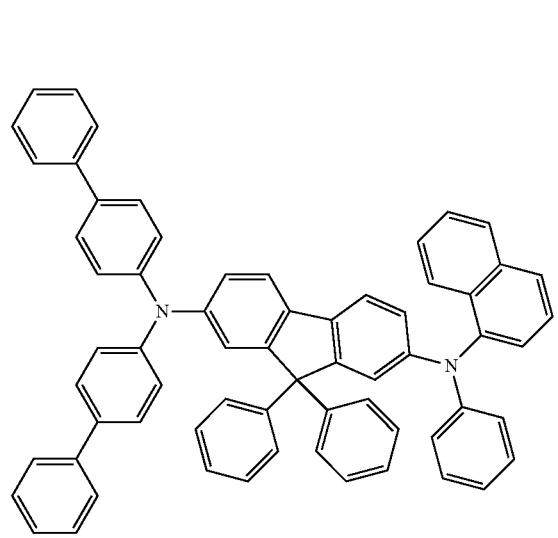
116
-continued
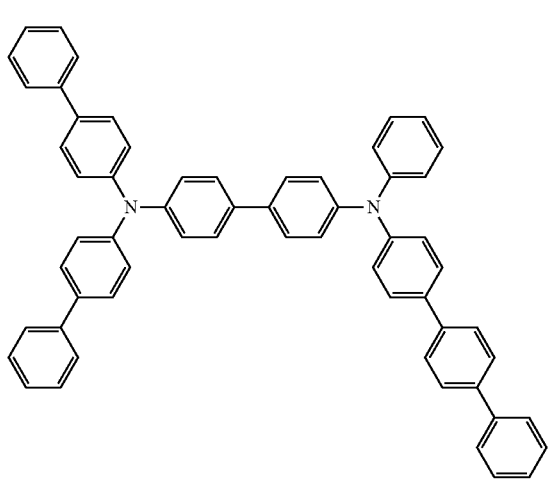
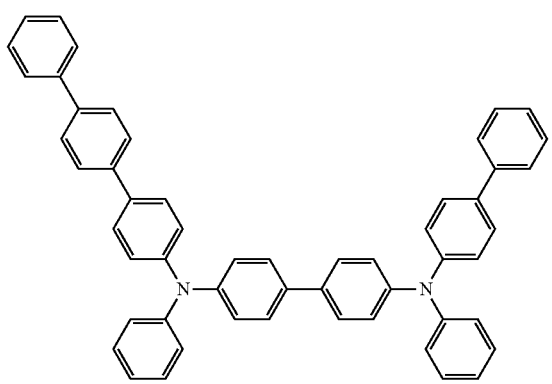
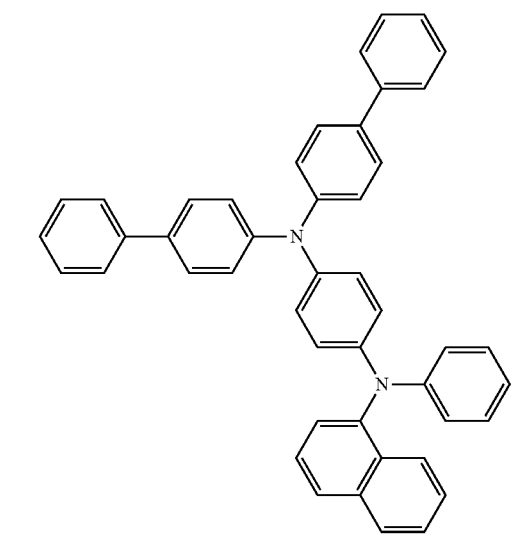

117
-continued
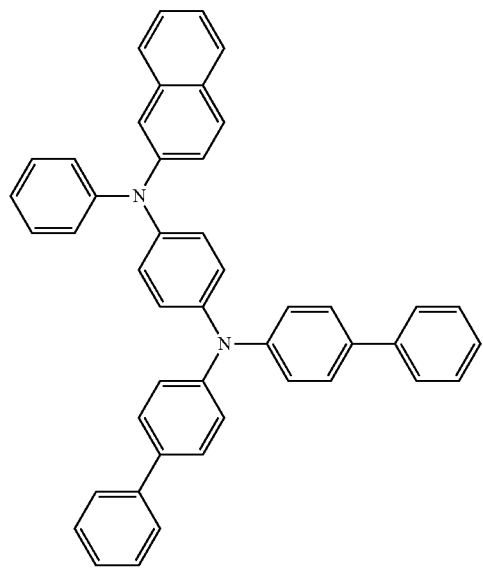
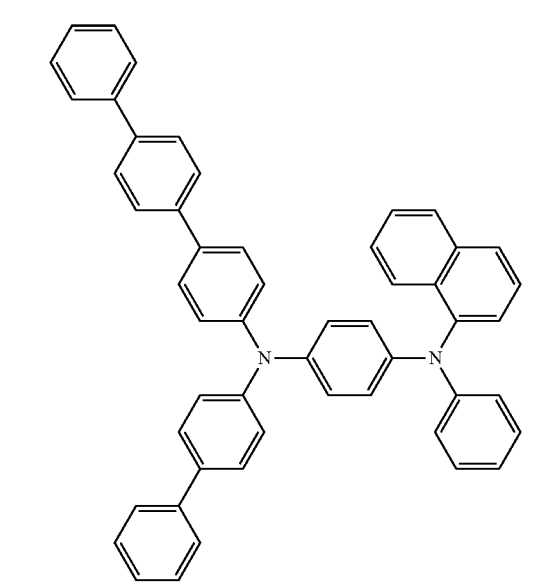
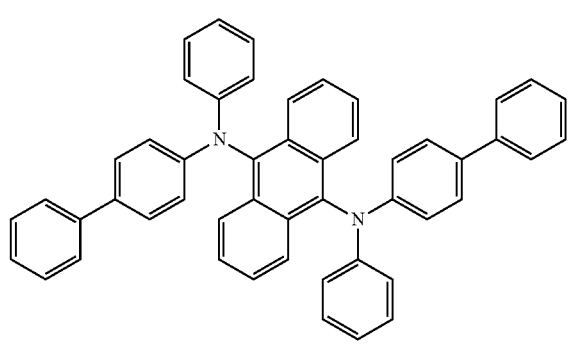
118
-continued
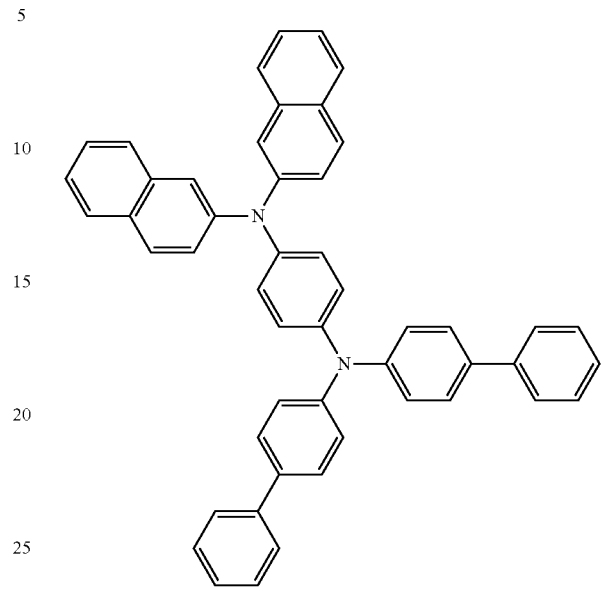
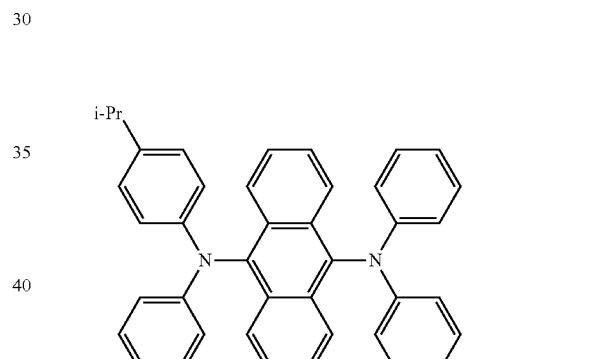
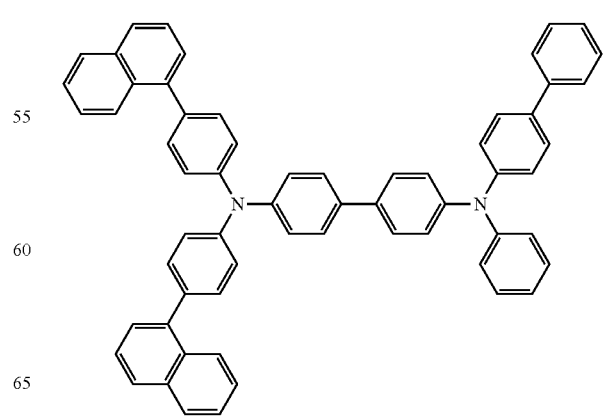

119
-continued
120
-continued
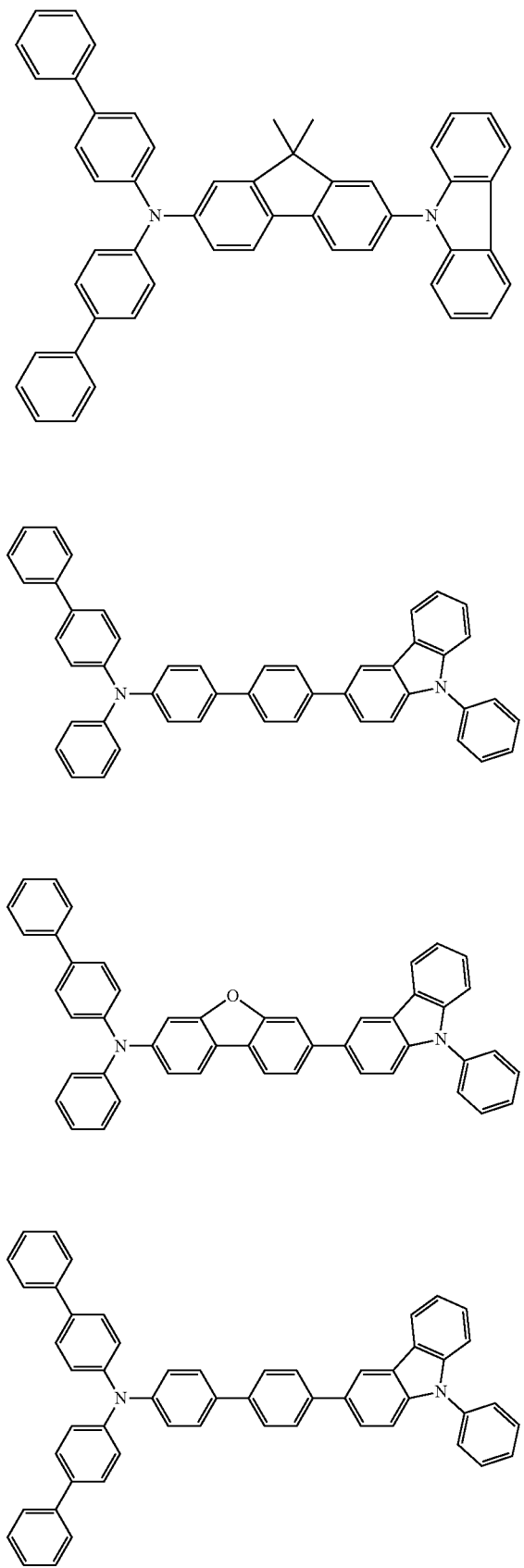
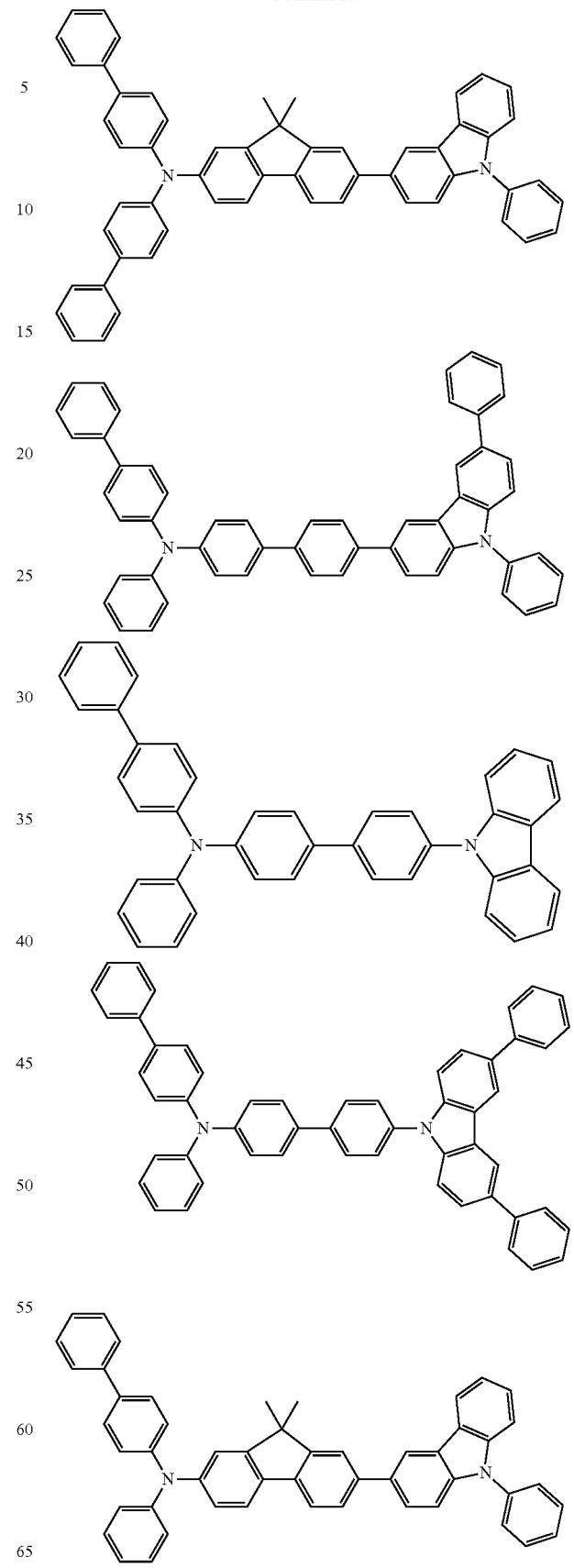

Aromatic amine represented by the following (II) can also be preferably used for forming the hole injecting layer or the hole transporting layer.

[Chemical Formula 48]

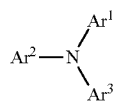

(II)

In the above (II), $Ar^1$ to $Ar^3$ each represent the same as $Ar^1$ to $Ar^4$ of the above formula (I). Examples of the compound represented by the general formula (II) are shown below. However, the compound represented by the formula (II) is not limited thereto.

[Chemical Formula 49]

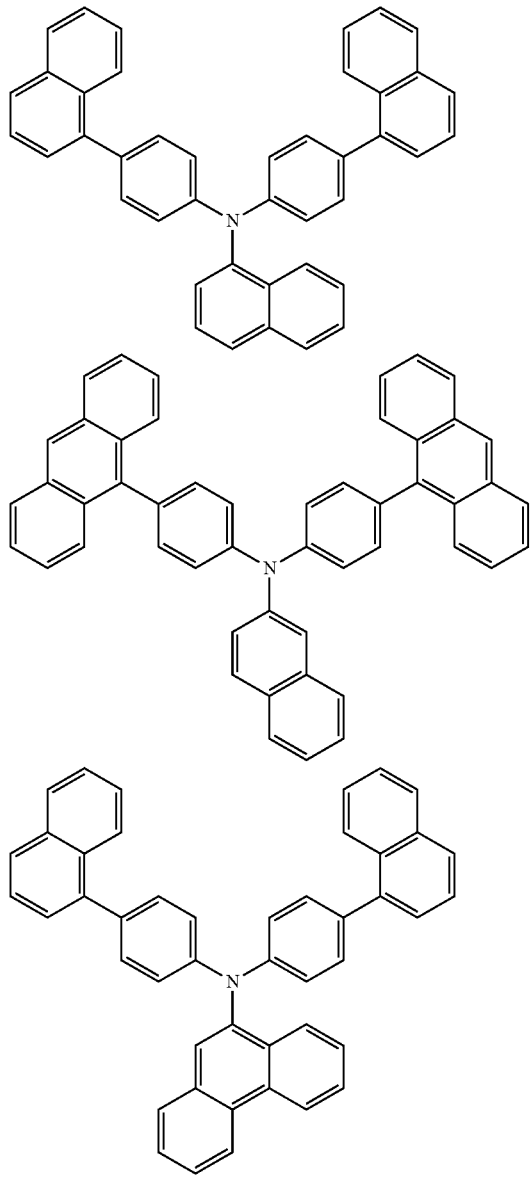

-continued

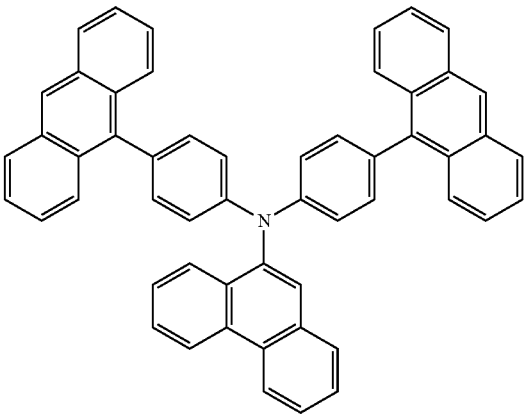

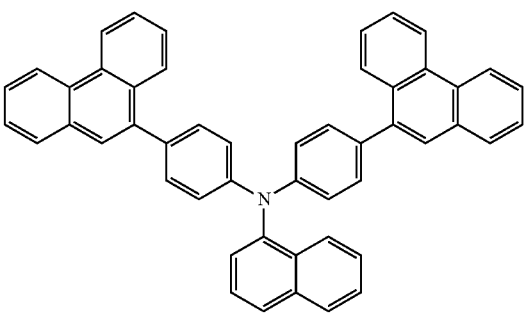

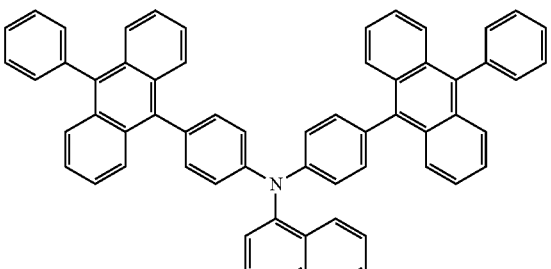

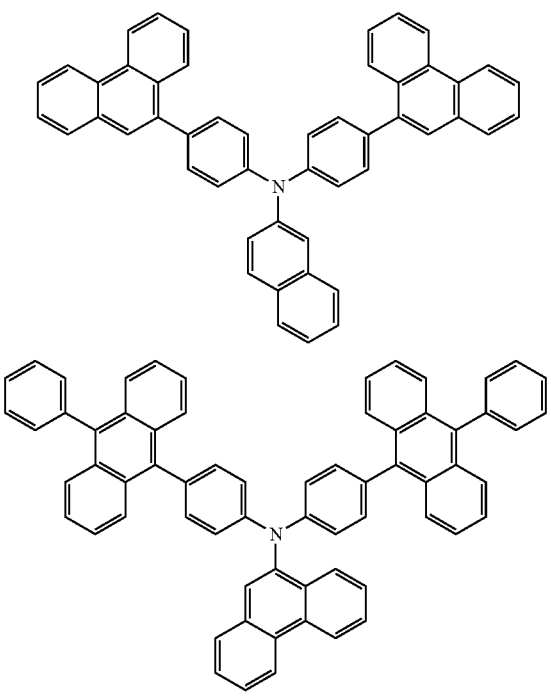

123
-continued
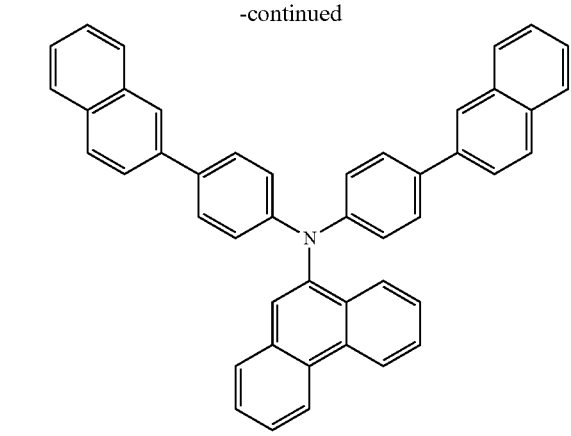
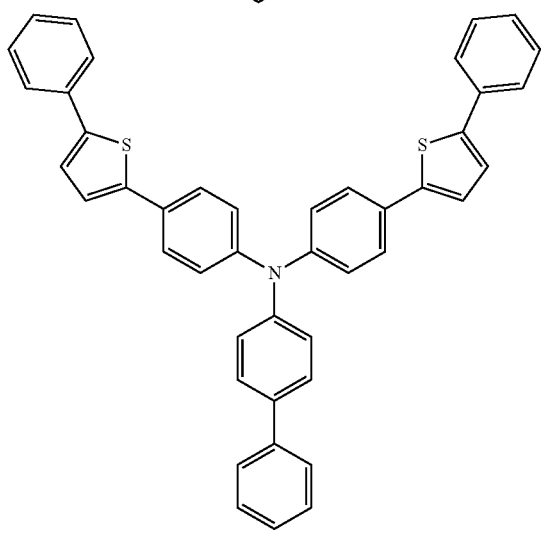
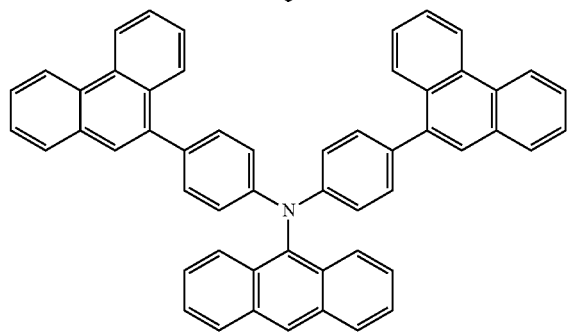
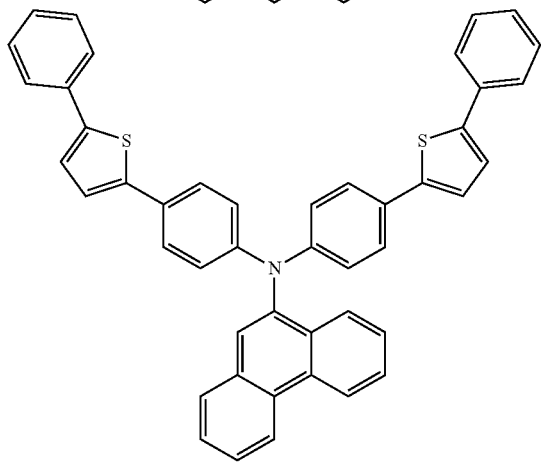
124
-continued
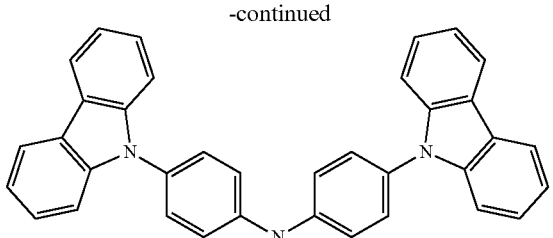
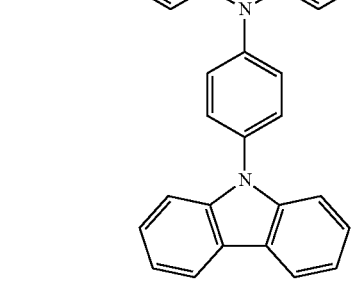
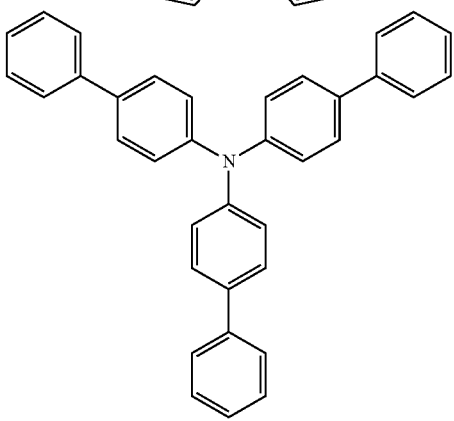
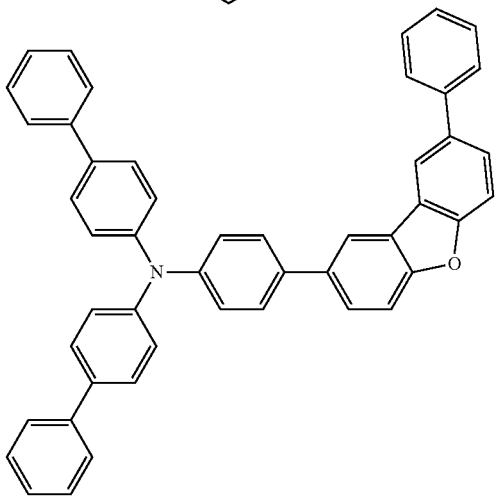
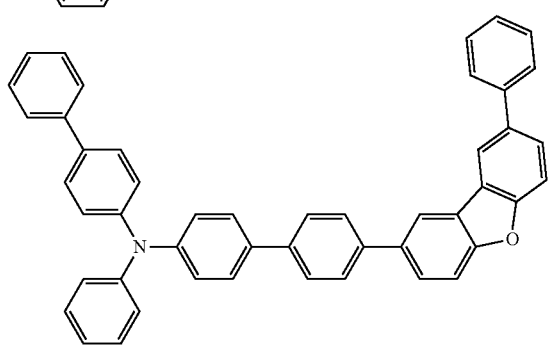

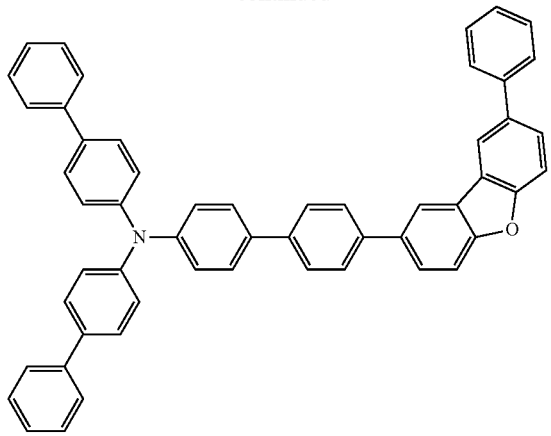

It should be noted that the invention is not limited to the above description but may include any modification as long as such modification stays within a scope and a spirit of the present invention.

For instance, the following is a preferable example of such modification made to the invention.

According to this exemplary embodiment, the emitting layer may also preferably contain an assistance substance for assisting injection of charges.

When the emitting layer is formed of a host material having a wide energy gap, a difference in ionization potential (Ip) between the host material and the hole injecting/transporting layer etc. becomes so large that injection of the holes into the emitting layer becomes difficult, which may cause a rise in a driving voltage required for providing sufficient luminance.

In the above instance, introducing a hole-injectable or hole-transportable assistance substance for assisting injection of charges in the emitting layer can contribute to facilitation of the injection of the holes into the emitting layer and to reduction of the driving voltage.

As the assistance substance for assisting the injection of charges, for instance, a general hole injecting material, a general hole transporting material or the like can be used.

Examples of the assistance substance are a triazole derivative (see, for instance, the specification of U.S. Pat. No. 3,112,197), an oxadiazole derivative (see, for instance, the specification of U.S. Pat. No. 3,189,447), an imidazole derivative (see, for instance, JP-B-37-16096), a polyarylalkane derivative (see, for instance, the specifications of U.S. Pat. No. 3,615,402, U.S. Pat. No. 3,820,989, and U.S. Pat. No. 3,542,544, JP-B-45-555, JP-B-51-10983, JP-A-51-93224, JP-A-55-17105, JP-A-56-4148, JP-A-55-108667, JP-A-55-156953 and JP-A-56-36656), a pyrazoline derivative and a pyrazolone derivative (see, for instance, the specifications of U.S. Pat. No. 3,180,729 and U.S. Pat. No. 4,278,746, JP-A-55-88064, JP-A-55-88065, JP-49-105537, JP-A-55-51086, JP-A-56-80051, JP-A-56-88141, JP-A-57-45545, JP-A-54-112637 and JP-A-55-74546), a phenylenediamine derivative (see, for instance, the specification of U.S. Pat. No. 3,615,404, JP-B-51-10105, JP-B-46-3712, JP-B-47-25336, JP-A-54-53435, JP-A-54-110536 and JP-A-54-119925), an arylamine derivative (see, for instance, the specifications of U.S. Pat. No. 3,567,450, U.S. Pat. No. 3,180,703, U.S. Pat. No. 3,240,597, U.S. Pat. No. 3,658,520, U.S. Pat. No. 4,232,103, U.S. Pat. No. 4,175,961 and U.S. Pat. No. 4,012,376, JP-B-49-35702, JP-B-39-27577, JP-A-55-144250, JP-A-56-119132 and JP-A-56-22437 and the specification of West Germany Patent No. 1,110,518), an amino-substituted chalcone derivative (see, for instance, the specification of U.S. Pat. No. 3,526,501), an oxazole derivative (disclosed in, for instance, the specification of U.S. Pat. No. 3,257,203), a styrylanthracene derivative (see, for instance, JP-A-56-46234), a fluorenone derivative (see, for instance, JP-A-54-110837), a hydrazone derivative (see, for instance, the specification of U.S. Pat. No. 3,717,462 and JP-A-54-59143, JP-A-55-52063, JP-A-55-52064, JP-A-55-46760, JP-A-55-85495, JP-A-57-11350, JP-A-57-148749 and JP-A-02-311591), a stilbene derivative (see, for instance, JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749 and JP-A-60-175052), a silazane derivative (see the specification of U.S. Pat. No. 4,950,950), a polysilane type (see JP-A-02-204996), an aniline-based copolymer (see JP-A-02-282263), and a conductive polymer oligomer (particularly, thiophene oligomer) disclosed in JP-A-01-211399.

The hole-injectable material, examples of which are as listed above, is preferably a porphyrin compound (disclosed in JP-A-63-295695 etc.), an aromatic tertiary amine compound or a styrylamine compound (see, for instance, the specification of U.S. Pat. No. 4,127,412, JP-A-53-27033, JP-A-54-58445, JP-A-54-149634, JP-A-54-64299, JP-A-55-79450, JP-A-55-144250, JP-A-56-119132, JP-A-61-295558, JP-A-61-98353 or JP-A-63-295695), particularly preferably an aromatic tertiary amine compound.

In addition, 4,4'-bis(N-(1-naphthyl)-N-phenylamino)biphenyl (hereinafter, abbreviated as NPD) having two fused aromatic rings in the molecule as disclosed in U.S. Pat. No. 5,061,569, or 4,4',4"tris(N-(3-methylphenyl)-N-phenylamino)triphenylamine (hereinafter, abbreviated as MTDATA) in which three triphenylamine units are bonded in a starburst form as disclosed in JP-A-04-308688 and the like may also be used.

Further, a hexaazatriphenylene derivative disclosed in Japanese Patent No. 3614405 and No. 3571977 and U.S. Pat. No. 4,780,536 may also preferably be used as the hole-injectable material.

Alternatively, inorganic compounds such as p-type Si and p-type SiC can also be used as the hole-injecting material.

A method of forming each of the layers in the organic EL device according to the aspect of the invention is not particularly limited. A conventionally-known method such as vacuum deposition or spin coating may be employed for forming the layers. The organic thin-film layer containing the compound represented by the formula (1), which is used in the organic EL device according to the exemplary embodiment of the invention, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device is not particularly limited, the thickness is generally preferably in a range of several nanometers to 1 μm because an excessively-thinned film likely entails defects such as a pin hole while an excessively-thickened film requires high voltage to be applied and deteriorates efficiency.

EXAMPLES

Next, the invention will be described in further detail by exemplifying Example(s) and Comparative(s). However, the invention is not limited by the description of Example(s).

Synthesis Example 1

Synthesis of Compound No. 1

[Chemical Formula 50]

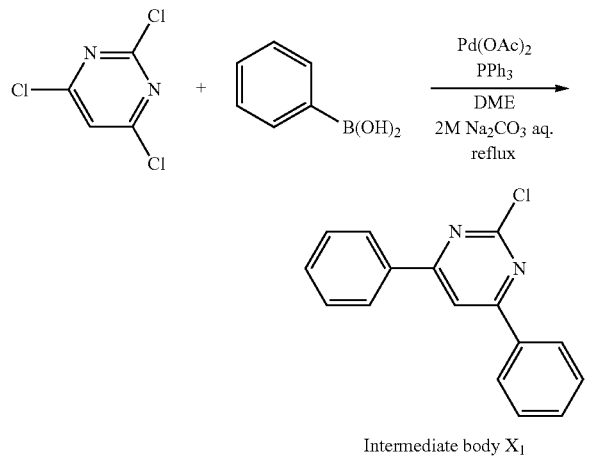

Intermediate body $X_1$

Under an Ar gas atmosphere, 2,4,6-trichloropyrimidine (18.3 g, 100 mmol), phenylboronic acid (24.4 g, 200 mmol), palladium acetate (0.56 g, 2.5 mmol), triphenylphosphine (1.31 g, 5.0 mmol), DME (930 ml) and an aqueous solution of 2M sodium carbonate (310 ml) were stirred for 15 hours at a reflux temperature. The solvent was distilled away under reduced pressure. The obtained residue was extracted by dichloromethane. The residue obtained by concentrating the organic phase was refined by silica-gel column chromatography (a developing solvent: hexane-ethyl acetate) to provide an intermediate body $X_1$ as a white solid. A yield of the intermediate body $X_1$ was 18.7 g and a yield rate thereof was 70%. (reference document: J. Org. Chem. 66 7125-7128 (2001))

[Chemical Formula 51]

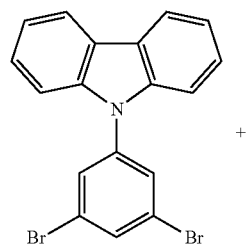

+

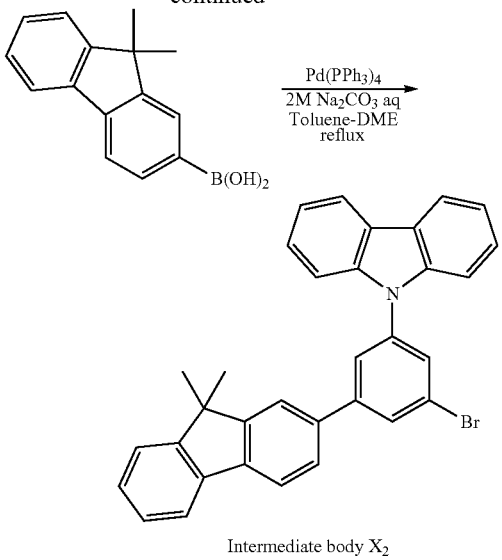

Intermediate body $X_2$

Under an Ar gas atmosphere, N-(3,5-dibromophenyl)carbazole (12.2 g, 30.4 mmol), 9,9-dimethylfluorene-2-boronic acid (7.24 g, 30.4 mmol), an aqueous solution of 2M sodium carbonate (30 ml), toluene (60 ml), DME (30 ml) and Pd(PPh$_3$)$_4$ (1.75 g) were stirred for 7 hours at a reflux temperature. After the reactant solution was cooled down to the room temperature, toluene (200 ml) and water (100 ml) were added thereto to separate an organic phase. The residue obtained by concentrating the organic phase was refined by silica-gel column chromatography (a developing solvent: hexane-toluene) to provide an intermediate body $X_2$ as a white solid. A yield of the intermediate body $X_2$ was 9.4 g and a yield rate thereof was 60%.

[Chemical Formula 52]

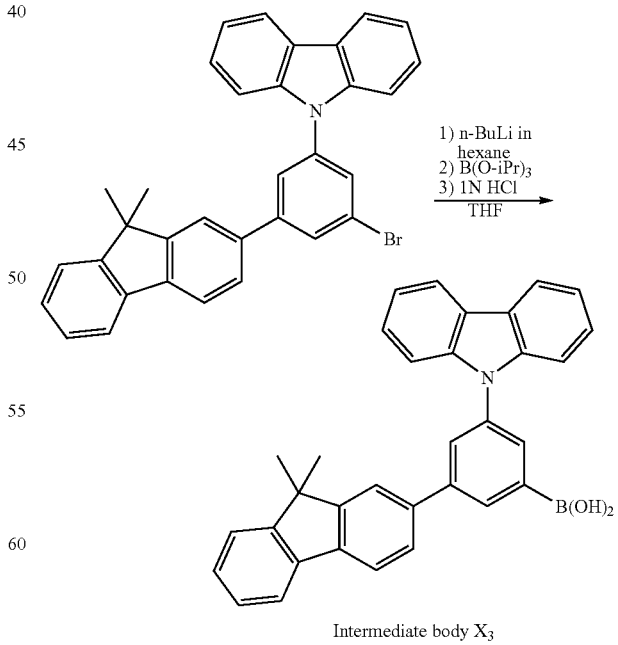

Intermediate body $X_3$

The intermediate body $X_2$ (5.14 g, 10 mmol) was added in dehydrated THF (100 ml), and was stirred at −70 degrees C.

under an Ar gas atmosphere. Next, n-BuLi (1.6M in hexane) (6.3 ml) was dropped thereinto. After stirring for two hours at −70 degrees C., 5.64 g (30 mmol) of triisopropylborate was dropped thereinto. After stirring for one hour at −70 degrees C., the reactant mixture was stirred at the room temperature for five hours. Subsequently, 1N-hydrochloric acid (30 ml) was added thereto and stirred for one hour at the room temperature. THF was distilled away under reduced pressure and was extracted by dichloromethane to provide an organic phase. The organic phase was dried by anhydrous magnesium sulfate. The residue obtained by concentrating the solvent was washed with toluene to provide an intermediate body $X_3$ as a white solid. A yield of the intermediate body $X_3$ was 3.1 g and a yield rate thereof was 65%.

[Chemical Formula 53]

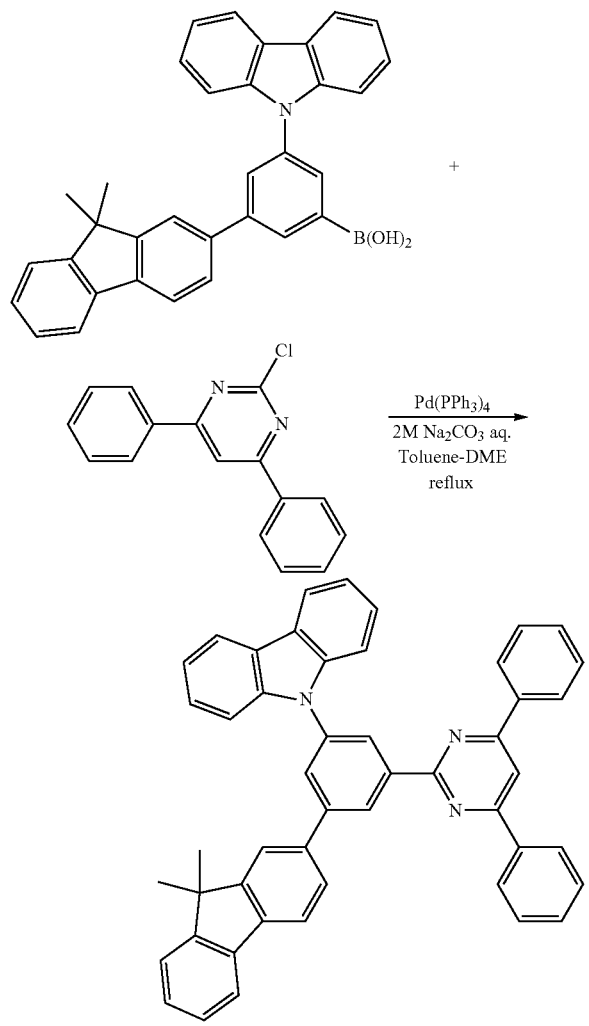

Compound No. 1

Under an Ar gas atmosphere, the intermediate body $X_3$ (4.8 g, 10 mmol), the intermediate body $X_1$ (2.66 g, 10 mmol), an aqueous solution of 2M sodium carbonate (12 ml), toluene (20 ml), DME (20 ml) and Pd(PPh$_3$)$_4$ (0.35 g) were stirred for 16 hours at a reflux temperature. After the reactant solution was cooled down to the room temperature, toluene (200 ml) and water (100 ml) were added thereto to separate an organic phase. The residue obtained by concentrating the organic phase was refined by silica-gel column chromatography (a developing solvent: hexane-toluene) and was recrystallized by toluene twice to provide a target object (a compound No. 1) as a white solid. A yield of the compound No. 1 was 3.0 g and a yield rate thereof was 45%.

FD mass analysis consequently showed that m/e was equal to 665 while a calculated molecular weight was 654.

Synthesis Example 2

Synthesis of Compound No. 2

[Chemical Formula 54]

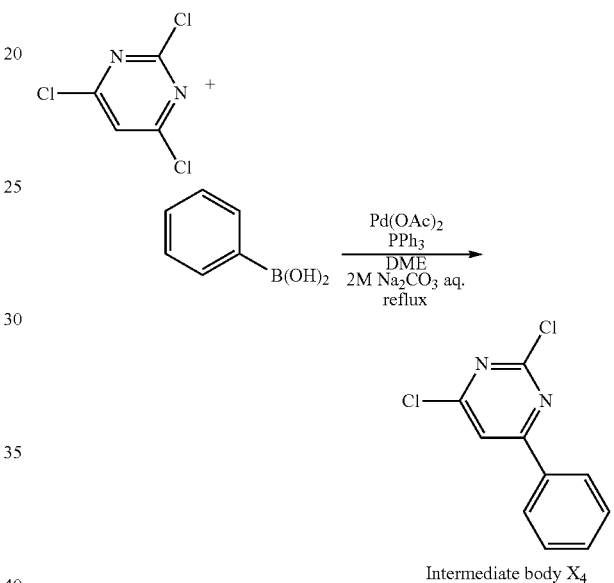

Intermediate body $X_4$

Under an Ar gas atmosphere, 2,4,6-trichloropyrimidine (25.0 g, 136.3 mmol), phenylboronic acid (16.6 g, 136.3 mmol), palladium acetate (1.53 g, 6.82 mmol), triphenylphosphine (3.58 g, 13.6 mmol), DME (1250 ml) and an aqueous solution of 2M sodium carbonate (211 ml) were stirred for 16 hours at a reflux temperature. The solvent was distilled away under reduced pressure. The obtained residue was extracted by dichloromethane. The residue obtained by concentrating the organic phase was refined by silica-gel column chromatography (a developing solvent: hexane-ethyl acetate) to provide an intermediate body $X_4$ as a white solid. A yield of the intermediate body $X_4$ was 22.1 g and a yield rate thereof was 72%. (reference document: J. Org. Chem. 66 7125-7128 (2001))

[Chemical Formula 55]

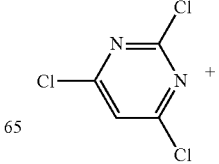

-continued

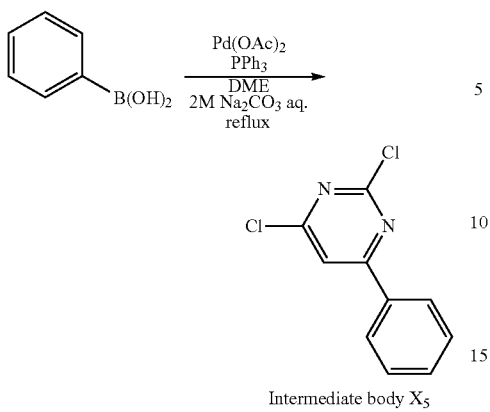

Intermediate body X₅

Under an Ar gas atmosphere, 2,4-dichloro-6-phenylpyrimidine (the intermediate body X₄) (6.0 g, 26.6 mmol), 9,9-dimethylfluorene-2-boronic acid (6.34 g, 26.6 mmol), palladium acetate (0.30 g, 1.33 mmol), triphenylphosphine (0.70 g, 2.66 mmol), DME (250 ml) and an aqueous solution of 2M sodium carbonate (42 ml) were stirred for 8 hours at a reflux temperature. The solvent was distilled away under reduced pressure. The obtained residue was extracted by toluene. The residue obtained by concentrating the organic phase was refined by silica-gel column chromatography (a developing solvent: hexane-toluene) to provide an intermediate body X₅ as a white solid. A yield of the intermediate body X₅ was 7.2 g and a yield rate thereof was 70%.

[Chemical Formula 56]

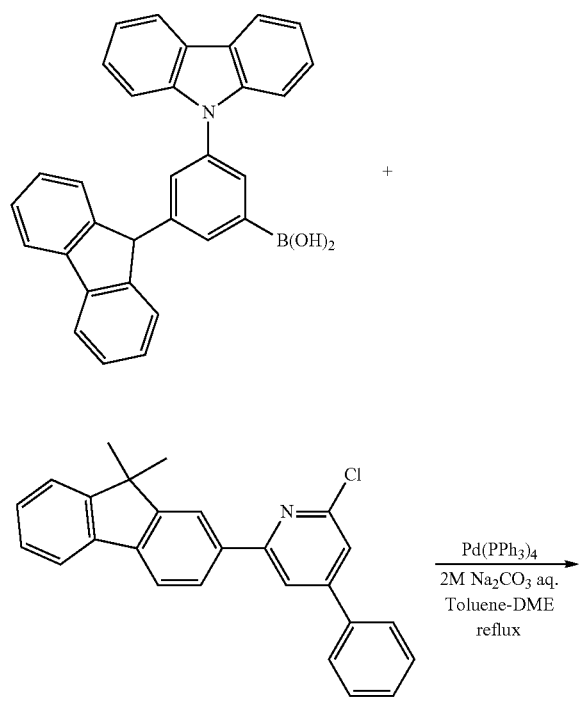

-continued

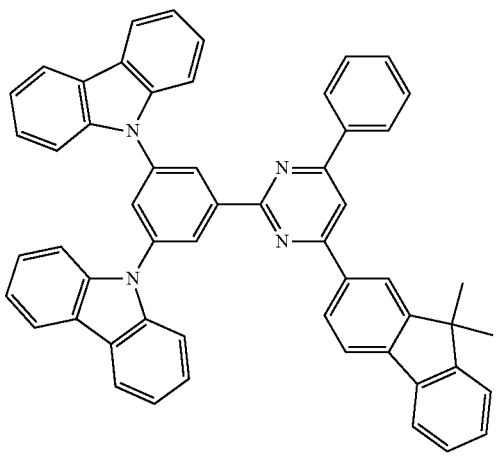

Compound No. 2

Under an Ar gas atmosphere, 3,5-bis-carbazolylphenyl boronic acid (4.52 g, 10 mmol), the intermediate body X₅ (3.83 g, 10 mmol), an aqueous solution of 2M sodium carbonate (12 ml), toluene (20 ml), DME (20 ml) and Pd(PPh₃)₄ (0.35 g) were stirred for 16 hours at a reflux temperature. After the reactant solution was cooled down to the room temperature, toluene (200 ml) and water (100 ml) were added thereto to separate an organic phase. The residue obtained by concentrating the organic phase was refined by silica-gel column chromatography (a developing solvent: hexane-toluene) and was recrystallized by toluene twice to provide a target object (a compound No. 2) as a white solid. A yield of the compound No. 2 was 3.0 g and a yield rate thereof was 40%.

FD mass analysis consequently showed that m/e was equal to 754 while a calculated molecular weight was 754.

Synthesis Example 3

Synthesis of Compound No. 3

[Chemical Formula 57]

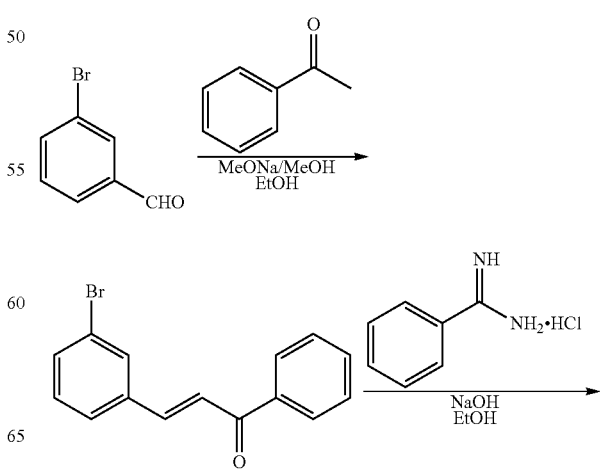

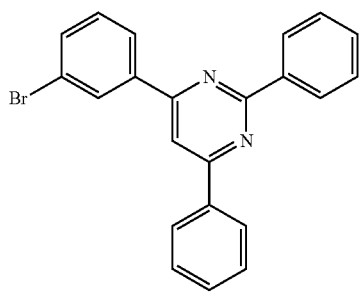

Intermediate body X$_6$

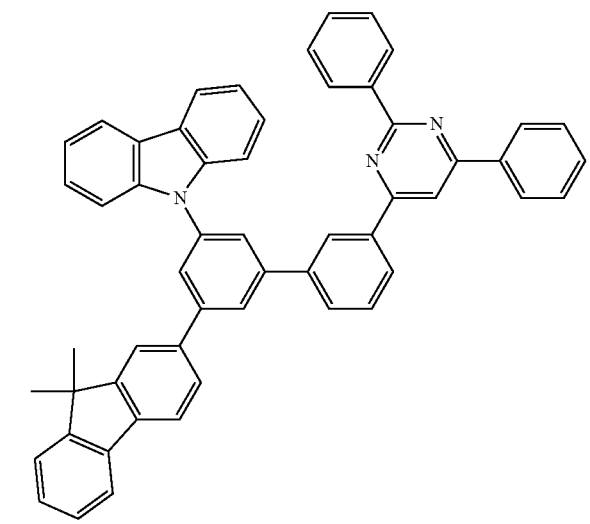

Compound No. 3

3-bromobenzaldehyde (18.5 g, 100 mmol), acetophenone (12.0 g, 100 mmol), 1N-sodium methoxide/methanol solution (10 ml) and ethanol (200 ml) were stirred for five hours at the room temperature under an Ar gas atmosphere. Subsequently, the reactant mixture was heated and stirred for another four hours at a reflux temperature. Next, benzamidine hydrochloride (9.4 g, 60 mmol) and sodium hydroxide (8.0 g, 200 mmol) were added thereto and stirred for five hours at 70 degrees C. After the reaction, the reactant mixture was filtered to separate an extract. The extract was refined by silica-gel column chromatography (a developing solvent: dichloromethane) to provide an intermediate body X$_6$ as a white solid. A yield of the intermediate body X$_6$ was 10.1 g and a yield rate thereof was 26%.

Under an Ar gas atmosphere, the intermediate body X$_3$ (4.8 g, 10 mmol), the intermediate body X$_6$ (3.9 g, 10 mmol), an aqueous solution of 2M sodium carbonate (12 ml), toluene (20 ml), DME (20 ml) and Pd(PPh$_3$)$_4$ (0.35 g) were stirred for 16 hours at a reflux temperature. After the reactant solution was cooled down to the room temperature, toluene (200 ml) and water (100 ml) were added thereto to separate an organic phase. The residue obtained by concentrating the organic phase was refined by silica-gel column chromatography (a developing solvent: hexane-toluene) and was recrystallized by toluene twice to provide a target object (a compound No. 3) as a white solid. A yield of the compound No. 3 was 3.2 g and a yield rate thereof was 43%.

FD mass analysis consequently showed that m/e was equal to 741 while a calculated molecular weight was 741.

Synthesis Example 4

Synthesis of Compound No. 4

[Chemical Formula 58]

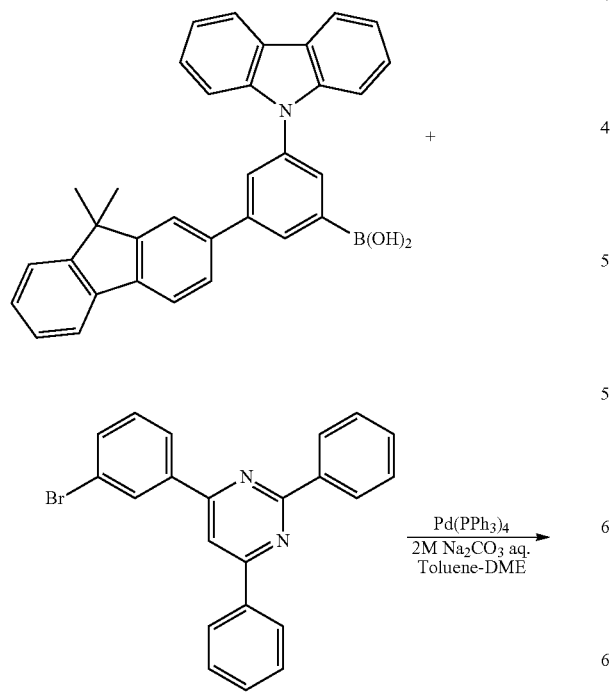

[Chemical Formula 59]

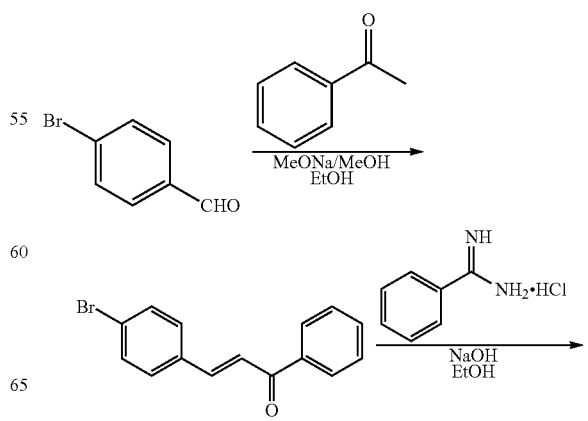

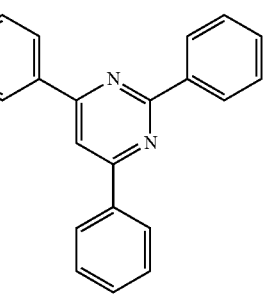

Intermediate body X₇

4-bromobenzaldehyde (18.5 g, 100 mmol), acetophenone (12.0 g, 100 mmol), 1N-sodium methoxide/methanol solution (10 ml) and ethanol (200 ml) were stirred at room temperature for 5 hours at the room temperature under an Ar gas atmosphere. Subsequently, the reactant mixture was heated and stirred for another four hours at a reflux temperature. Next, benzamidine hydrochloride (9.4 g, 60 mmol) and sodium hydroxide (8.0 g, 200 mmol) were added thereto and stirred for five hours at 70 degrees C. After the reaction, the reactant mixture was filtered to separate an extract. The extract was refined by silica-gel column chromatography (a developing solvent: dichloromethane) to provide an intermediate body X₇ as a white solid. A yield of the intermediate body X₇ was 11.6 g and a yield rate thereof was 30%.

[Chemical Formula 60]

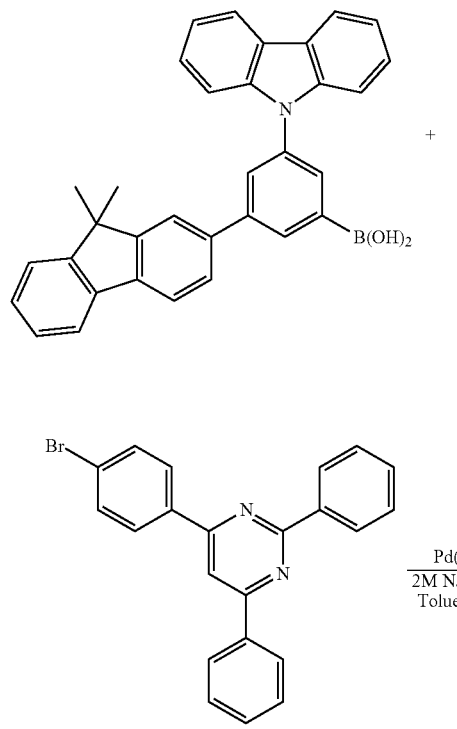

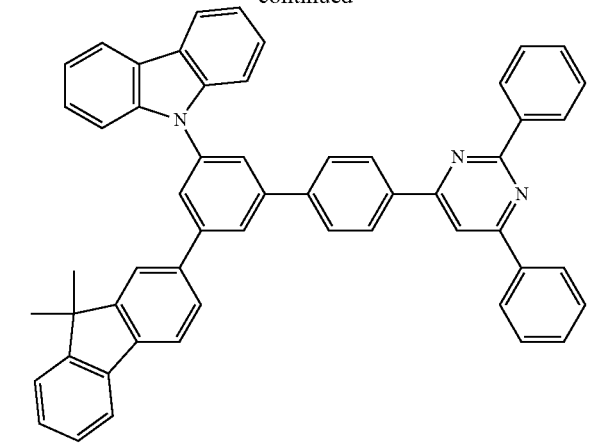

Compound No. 4

Under an Ar gas atmosphere, the intermediate body X₃ (4.8 g, 10 mmol), the intermediate body X₇ (3.9 g, 10 mmol), an aqueous solution of 2M sodium carbonate (12 ml), toluene (20 ml), DME (20 ml) and Pd(PPh₃)₄ (0.35 g) were stirred for 16 hours at a reflux temperature. After the reactant solution was cooled down to the room temperature, toluene (200 ml) and water (100 ml) were added thereto to separate an organic phase. The residue obtained by concentrating the organic phase was refined by silica-gel column chromatography (a developing solvent: hexane-toluene) and was recrystallized by toluene twice to provide a target object (a compound No. 4) as a white solid. A yield of the compound No. 4 was 2.6 g and a yield rate thereof was 35%.

FD mass analysis consequently showed that m/e was equal to 741 while a calculated molecular weight was 741.

Synthesis Example 5

Synthesis of Compound No. 5

[Chemical Formula 61]

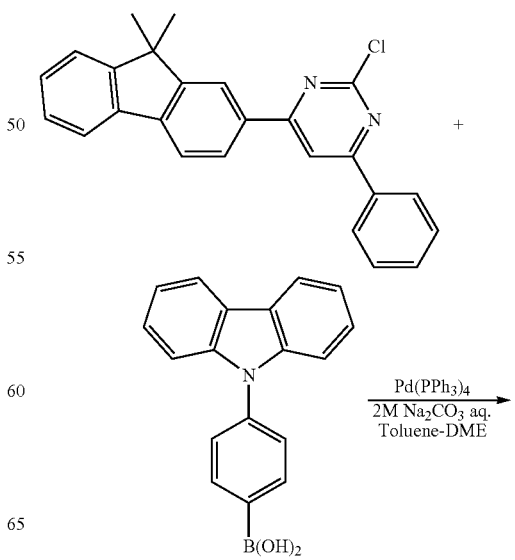

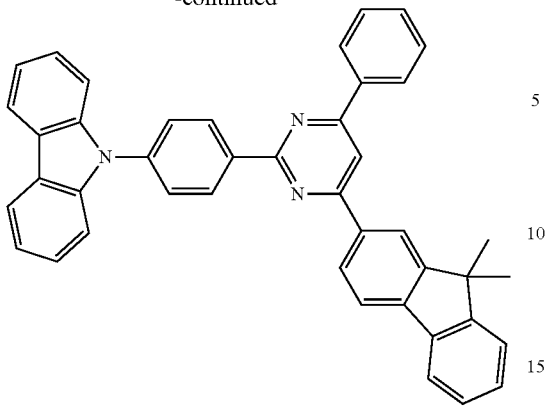

Compound No. 5

Under an Ar gas atmosphere, the intermediate body $X_5$ (3.8 g, 10 mmol), 4-carbazolylphenyl boronic acid (2.9 g, 10 mmol), an aqueous solution of 2M sodium carbonate (12 ml), toluene (20 ml), DME (20 ml) and $Pd(PPh_3)_4$ (0.35 g) were stirred for 20 hours at a reflux temperature. After the reactant solution was cooled down to the room temperature, toluene (200 ml) and water (100 ml) were added thereto to separate an organic phase. The residue obtained by concentrating the organic phase was refined by silica-gel column chromatography (a developing solvent: hexane-toluene) and was recrystallized by toluene twice to provide a target object (a compound No. 5) as a white solid. A yield of the compound No. 5 was 2.8 g and a yield rate thereof was 47%.

FD mass analysis consequently showed that m/e was equal to 589 while a calculated molecular weight was 589.

Example 1

Manufacture of Organic EL Device 1

A glass substrate (size: 25 mm×75 mm×1.1 mm) having an ITO transparent electrode (manufactured by Geomatec Co., Ltd.) was ultrasonic-cleaned in isopropyl alcohol for five minutes, and then UV (Ultraviolet)/ozone-cleaned for 30 minutes.

After the glass substrate having the transparent electrode was cleaned, the glass substrate was mounted on a substrate holder of a vacuum deposition apparatus, and a hole injecting layer was initially formed by depositing a compound A onto the substrate to be 40 nm thick to cover a surface of the glass substrate where a transparent electrode line was provided. Next, a compound B was deposited onto the hole injecting layer to be 20 nm thick to provide a hole transporting layer.

On the hole transporting layer, the compound No. 1 as a phosphorescent host and $Ir(Ph-ppy)_3$ as a phosphorescent dopant were co-evaporated (thickness: 40 nm), thereby providing a phosphorescent-emitting layer. The concentration of $Ir(Ph-ppy)_3$ was 20 mass %.

On the phosphorescent-emitting layer, a 30-nm thick film of a compound C, a 1-nm thick film of LiF, an 80-nm thick film of a metal Al were laminated in sequence, thereby providing a cathode. LiF, which is an electron injectable electrode, was formed at a speed of 1 Å/min.

[Chemical Formula 62]

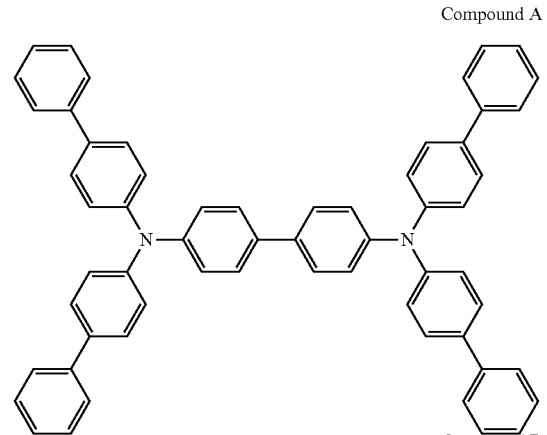

Compound A

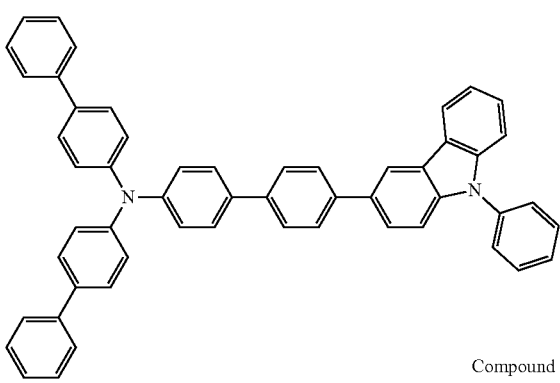

Compound B

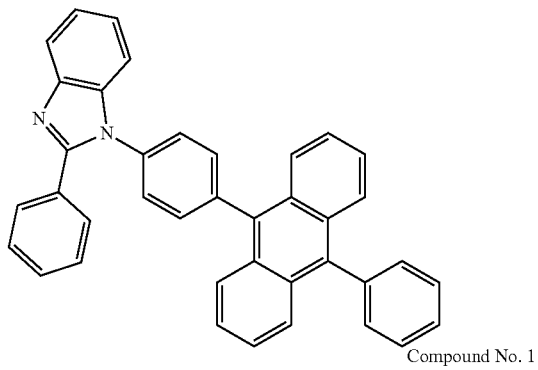

Compound C

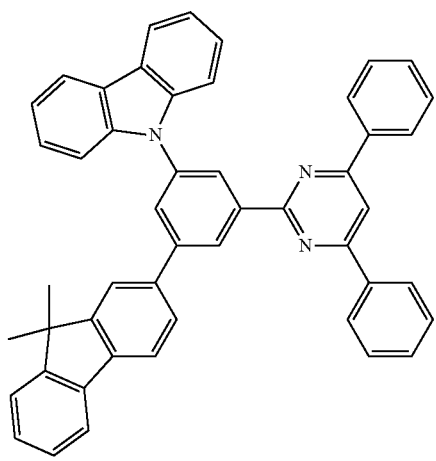

Compound No. 1

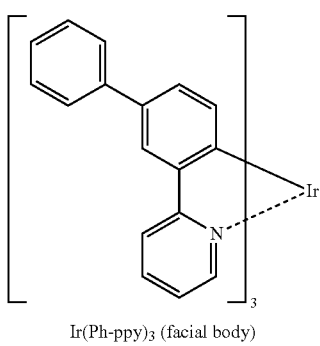

Ir(Ph-ppy)₃ (facial body)

Evaluation on Luminescent Performance of Organic EL Device

The organic EL devices each manufactured as described above were driven by direct-current electricity to emit light, so that luminance intensity and current density were measured to obtain voltage and luminous efficiency at a current density of 1 mA/cm². Further, time elapsed until the initial luminance intensity of 20,000 cd/m² was reduced to the half (i.e., time until half-life) was obtained. The results are shown in Table 1.

Examples 2 to 5

The organic EL devices according respectively to Examples 2 to 5 were formed and evaluated in the same manner as in Example 1 except that the host compound No. 1 was replaced by host materials described in Table 1. The results of the evaluation are shown in Table 1.

[Chemical Formula 63]

Compound No. 2

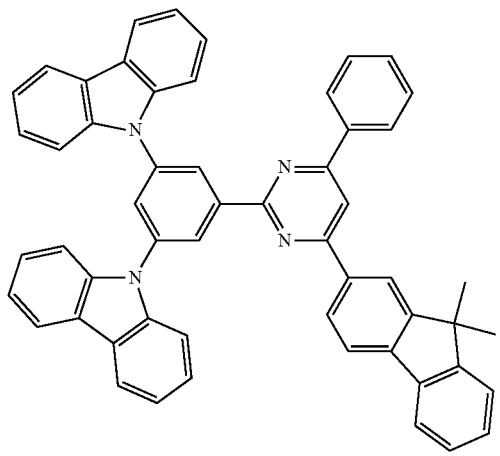

Compound No. 3

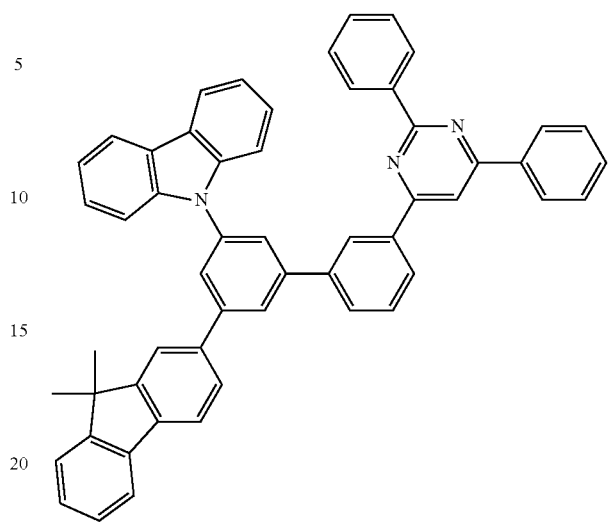

Compound No. 4

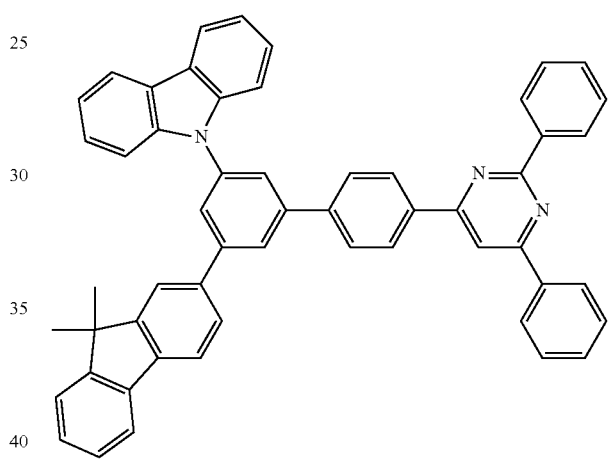

Compound No. 5

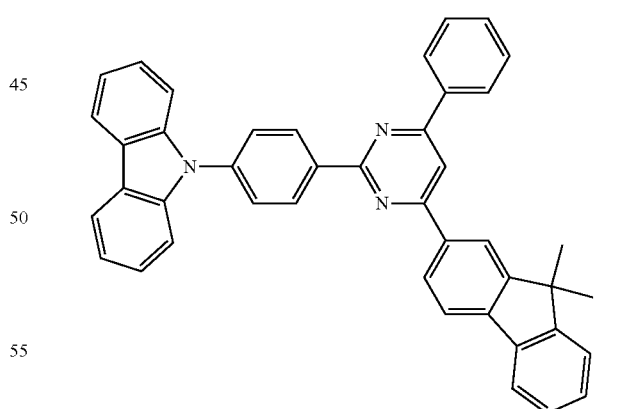

Comparative 1

An organic EL device according to Comparative 1 was formed and evaluated in the same manner as in Example 1 except that the host compound No. 1 was replaced by a compound D (a host material described in WO2003/08076). The results of the evaluation are shown in Table 1.

[Chemical Formula 64]

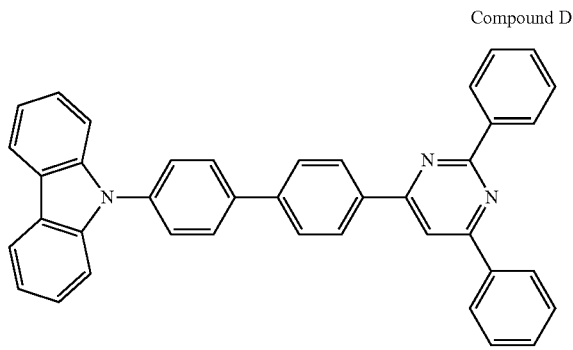

Compound D

TABLE 1

| | Host compound | Voltage (V) @ 1 mA/cm$^2$ | Luminous efficiency (cd/A) @ 1 mA/cm$^2$ | Time until half-life (hrs) 20000 cd/m$^2$ |
|---|---|---|---|---|
| Example 1 | No. 1 | 3.2 | 86.7 | 350 |
| Example 2 | No. 2 | 3.0 | 87.9 | 450 |
| Example 3 | No. 3 | 3.6 | 88.3 | 500 |
| Example 4 | No. 4 | 3.5 | 81.3 | 500 |
| Example 5 | No. 5 | 3.1 | 74.4 | 300 |
| Comparative 1 | Compound D | 4.7 | 51.1 | 300 |

As seen from Table 1, the organic EL devices of Examples were emittable at low voltage and exhibited a high luminous efficiency as compared with the organic EL device of Comparative 1.

Example 6

A glass substrate (size: 25 mm×75 mm×1.1 mm) having an ITO transparent electrode (manufactured by Geomatec Co., Ltd.) was ultrasonic-cleaned in isopropyl alcohol for five minutes, and then UV (Ultraviolet)/ozone-cleaned for 30 minutes.

After the glass substrate having the transparent electrode was cleaned, the glass substrate was mounted on a substrate holder of a vacuum deposition apparatus, and a hole injecting layer was initially formed by depositing a compound A onto the substrate to be 40 nm thick to cover a surface of the glass substrate where a transparent electrode line was provided. Next, a compound B was deposited onto the hole injecting layer to be 20 nm thick to provide a hole transporting layer.

On the hole transporting layer, the compound D as a phosphorescent host and Ir(Ph-ppy)$_3$ as a phosphorescent dopant were co-evaporated (thickness: 40 nm), thereby providing a phosphorescent-emitting layer. The concentration of Ir(Ph-ppy)$_3$ was 20 mass %.

On the phosphorescent-emitting layer, a 5-nm thick film of the compound No. 2, a 25-nm thick film of the compound C, a 1-nm thick film of LiF, an 80-nm thick film of a metal Al were laminated in sequence, thereby providing a cathode. LiF, which is an electron injectable electrode, was formed at a speed of 1 Å/min.

The results of the evaluation of the organic EL device are shown in Table 2. The comparative 1 shown in Table 2 as a comparative is the same as the comparative 1 above.

TABLE 2

| | Host compound | Electron transporting compound | Voltage (V) @ 1 mA/cm$^2$ | Luminous efficiency (cd/A) @ 1 mA/cm$^2$ | Time until half-life (hrs) 20000 cd/m$^2$ |
|---|---|---|---|---|---|
| Example 6 | Compound D | No. 2 | 4.7 | 52.5 | 400 |
| Comparative 1 | Compound D | none | 4.7 | 51.1 | 300 |

As seen from Table 2, the compound of the invention was usable as an electron transporting compound and the organic EL devices of Examples had a longer lifetime than the organic EL device of the comparative.

As described in detail, when the compounds of the invention are used as an organic-EL-device material, an organic EL device having a high luminous efficiency and being emittable at low voltage is obtainable. Accordingly, the organic EL device of the invention is significantly usable as a light source of various electronic devices and the like. Moreover, the compound of the invention is effectively usable as an organic-electron-device material for an organic solar cell, an organic semiconductor laser, a sensor using an organic substance and an organic TFT.

The invention claimed is:

1. A fluorene-containing aromatic compound represented by formula (1):

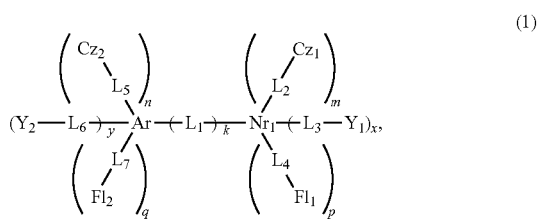

(1)

wherein:
Nr$_1$ represents a substituted or unsubstituted pyridine ring, a substituted or unsubstituted pyrimidine ring, or a substituted or unsubstituted triazine ring;
Ar represents a single bond or a substituted or unsubstituted aromatic ring having 5 to 40 ring carbon atoms;
Fl$_1$ and Fl$_2$ each independently represent a substituted or unsubstituted fluorenyl group, and when Fl$_1$ or Fl$_2$ comprises one or more substituents, each substituent is independently a linear, branched, or cyclic alkyl group having 1 to 20 carbon atoms, a haloalkyl group having 1 to 20 carbon atoms, a linear, branched, or cyclic alkylsilyl group having 1 to 10 carbon atoms, a cyano group, a halogen atom, or an aryl group having 6 to 22 ring carbon atoms;
p represents an integer of 0 to 3, such that when p is 2 or more, the L$_4$s are the same or different, and the Fl$_1$s are the same or different;
q represents an integer of 0 to 3, such that when q is 2 or more, the L$_7$s are the same or different, and the Fl$_2$s are the same or different;
p+q=1 or more;
Cz$_1$ and Cz$_2$ each independently represent a substituted or unsubstituted carbazolyl group;
m represents an integer of 0 to 3, such that when m is 2 or more, the L$_2$s are the same or different, and the Cz$_1$s are the same or different;

n represents an integer of 0 to 3, such that when n is 2 or more, the $L_5$s are the same or different, and the $Cz_2$s are the same or different;

m+n=1 or more;

$Y^1$ and $Y^2$ each independently represent a hydrogen atom, a deuterium atom, a fluorine atom, a chlorine atom, a bromine atom, an iodine atom, a cyano group, a substituted or unsubstituted linear, branched, or cyclic alkyl group having 1 to 20 carbon atoms, a substituted or unsubstituted linear, branched, or cyclic alkoxy group having 1 to 20 carbon atoms, a substituted or unsubstituted linear, branched, or cyclic haloalkyl group having 1 to 20 carbon atoms, a substituted or unsubstituted linear, branched, or cyclic haloalkoxy group having 1 to 20 carbon atoms, a substituted or unsubstituted linear, branched, or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms;

x represents an integer of 1 to 3, such that when x is 2 or more, the $L_3$s are the same or different, and the $Y_1$s are the same or different;

y represents an integer of 1 to 3, such that when y is 2 or more, the $L_6$s are the same or different, and the $Y_2$s are the same or different;

m+p+x is less than or equal to the number of substituents of $Nr_1$ minus 1;

n+q+y is less than or equal to the number of substituents of Ar minus 1;

$L_1$ represents a single bond or a substituted or unsubstituted aromatic ring having 6 to 30 ring carbon atoms;

$L_2$ to $L_7$ each independently represent a single bond, a substituted or unsubstituted aromatic ring having 6 to 30 ring carbon atoms, or a substituted or unsubstituted aromatic heterocyclic ring having 2 to 30 ring carbon atoms;

k represents an integer of 1 to 3;

when p is 1 or greater, $Fl_1$ is joined to $L_4$ via the 2-position of $Fl_1$;

when q is 1 or greater, $Fl_2$ is joined to $L_7$ via the 2-position of $Fl_2$; and the fluorene-containing aromatic compound represented by formula (1) is not a compound represented by formula (2):

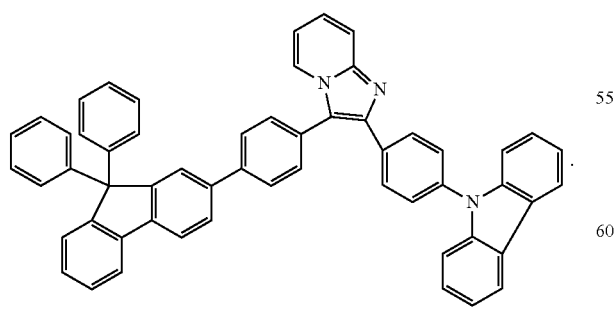

(2)

2. The compound of claim 1, wherein:
$Cz_1$ and $Cz_2$ are each independently represented by formula (3) or formula (4):

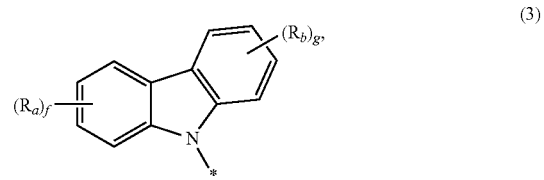

(3)

wherein:
Ra and Rb each independently represent a hydrogen atom, a deuterium atom, a fluorine atom, a chlorine atom, a bromine atom, an iodine atom, a cyano group, a substituted or unsubstituted linear, branched, or cyclic alkyl group having 1 to 20 carbon atoms, a substituted or unsubstituted linear, branched, or cyclic alkoxy group having 1 to 20 carbon atoms, a substituted or unsubstituted linear, branched, or cyclic haloalkyl group having 1 to 20 carbon atoms, a substituted or unsubstituted linear, branched, or cyclic haloalkoxy group having 1 to 20 carbon atoms, a substituted or unsubstituted linear, branched, or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms;

f and g each independently represent an integer of 1 to 4,

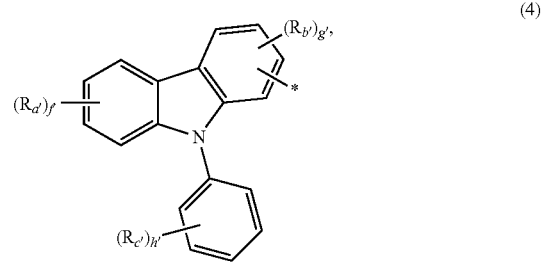

(4)

wherein:
Ra', Rb' and Rc' each independently represent a hydrogen atom, a deuterium atom, a fluorine atom, a chlorine atom, a bromine atom, an iodine atom, a cyano group, a substituted or unsubstituted linear, branched, or cyclic alkyl group having 1 to 20 carbon atoms, a substituted or unsubstituted linear, branched, or cyclic alkoxy group having 1 to 20 carbon atoms, a substituted or unsubstituted linear, branched, or cyclic haloalkyl group having 1 to 20 carbon atoms, a substituted or unsubstituted linear, branched, or cyclic haloalkoxy group having 1 to 20 carbon atoms, a substituted or unsubstituted linear, branched, or cyclic alkylsilyl group having 1 to 10 carbon atoms, a substituted or unsubstituted arylsilyl group having 6 to 30 carbon atoms, a substituted or unsubstituted aryl group having 6 to 30 ring carbon atoms, or a substituted or unsubstituted heteroaryl group having 2 to 10 ring carbon atoms;

f' represents an integer of 1 to 4;
g' represents an integer of 1 to 3; and
h' represents an integer of 1 to 5.

3. The compound of claim 1, wherein:
k is 1; and
m+n+p+q is less than or equal to 6.

4. The compound of claim 1, wherein $Y_1$ and $Y_2$ each independently represent a hydrogen atom or a phenyl group.

5. The compound of claim 1, wherein:
k is 1;
$L_1, L_2, L_3, L_5,$ and $L_6$ each independently represent a single bond, a substituted or unsubstituted phenylene group, a substituted or unsubstituted biphenylene group, a substituted or unsubstituted terphenylene group, or a substituted or unsubstituted fluorenylene group; and
$L_4$ and $L_7$ each independently represent a single bond, a substituted or unsubstituted phenylene group, a substituted or unsubstituted biphenylene group, or a substituted or unsubstituted terphenylene group.

6. The compound of claim 1, wherein:
m+n=1 or 2; and
p+q=1 or 2.

7. The compound of claim 1, wherein Ar represents a monocyclic aromatic ring selected from the group consisting of a substituted or unsubstituted benzene ring, a substituted or unsubstituted pyrazole ring, a substituted or unsubstituted imidazole ring, a substituted or unsubstituted triazole ring, a substituted or unsubstituted pyridine ring, a substituted or unsubstituted pyrimidine ring, a substituted or unsubstituted pyridazine ring, a substituted or unsubstituted pyrazine ring, a substituted or unsubstituted triazine ring, and a substituted or unsubstituted thiophene ring.

8. The compound of claim 1, wherein Ar is a benzene ring.

9. The compound of claim 1, wherein:
$Fl_1$ and $Fl_2$ are each independently represented by formula (5):

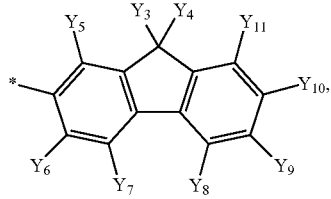

(5)

$Y_3$ and $Y_4$ each independently represent:
a hydrogen atom;
a deuterium atom;
a linear, branched, or cyclic alkyl group having 1 to 10 carbon atoms;
a linear, branched, or cyclic haloalkyl group having 1 to 10 carbon atoms;
a linear, branched, or cyclic alkylsilyl group having 1 to 10 carbon atoms;
a substituted or unsubstituted arylsilyl group having 6 to 30 carbon atoms;
a substituted or unsubstituted aryl group having 6 to 30 ring carbon atoms; or
a substituted or unsubstituted heteroaryl group having 2 to 10 ring carbon atoms; and
$Y_5, Y_6, Y_7, Y_8, Y_9, Y_{10},$ and $Y_{11}$ each independently represent:
a hydrogen atom;
a deuterium atom;
a fluorine atom;
a chlorine atom;
a bromine atom;
an iodine atom;
a cyano group;
a linear, branched, or cyclic alkyl group having 1 to 10 carbon atoms;
a linear, branched, or cyclic alkoxy group having 1 to 10 carbon atoms;
a linear, branched, or cyclic haloalkyl group having 1 to 10 carbon atoms;
a linear, branched, or cyclic haloalkoxy group having 1 to 10 carbon atoms;
a linear, branched, or cyclic alkylsilyl group having 1 to 10 carbon atoms;
a substituted or unsubstituted arylsilyl group having 6 to 30 carbon atoms;
a substituted or unsubstituted aryl group having 6 to 30 ring carbon atoms; or
a substituted or unsubstituted heteroaryl group having 2 to 10 ring carbon atoms.

10. The compound of claim 9, wherein $Y_3$ and $Y_4$ each independently represent a linear alkyl group having 1 to 10 carbon atoms or a phenyl group.

11. The compound of claim 10, wherein $Y_3$ and $Y_4$ each represent a methyl group.

12. The compound of claim 1, wherein
$Cz_1$ and $Cz_2$ are each independently represented by formula (3a) or formula (4a):

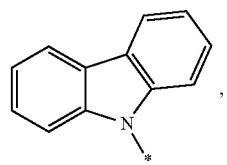

(3a)

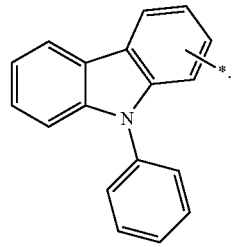

(4a)

13. The compound of claim 1, wherein $Nr_1$ is a pyrimidine ring.

14. An organic electroluminescence device material, comprising the compound of claim 1.

15. An organic electroluminescence device, comprising:
a cathode;
an anode; and
an organic thin-film layer between the cathode and the anode;
wherein:
the organic thin-film layer comprises one or more layers;
at least one layer of the organic thin-film layer is an emitting layer; and
at least one layer of the organic thin-film layer comprises the fluorene-containing aromatic compound of claim 1.

16. The device of claim 15, wherein the emitting layer comprises the fluorene-containing aromatic compound as a host material.

17. The device of claim 16, wherein the emitting layer further comprises a phosphorescent material.

18. The device of claim 17, wherein the phosphorescent material is an ortho metalation of a complex of a metal atom selected from the group consisting of iridium (Ir), osmium (Os), and platinum (Pt).

19. The device of claim 16, wherein:
the organic thin-film layer comprises an electron injecting layer situated between the cathode and the emitting layer; and
the electron injecting layer comprises a nitrogen-containing cyclic derivative.

20. The device of claim 15, wherein:
the organic thin-film layer comprises an electron transporting layer situated between the cathode and the emitting layer; and
the electron transporting layer comprises the fluorene-containing aromatic compound.

21. The device of claim 15, wherein a reduction-causing dopant is added in an interfacial region between the cathode and the organic thin-film layer.

22. The compound of claim 1, wherein $Nr_1$ is a pyridine ring.

23. The compound of claim 1, wherein $Nr_1$ is a triazine ring.

24. The compound of claim 1, wherein, when $Nr_1$ comprises one or more substituents, each substituent is independently a linear, branched, or cyclic alkyl group having 1 to 20 carbon atoms, a haloalkyl group having 1 to 20 carbon atoms, a linear, branched, or cyclic alkylsilyl group having 1 to 10 carbon atoms, a cyano group, a halogen atom, or an aryl group having 6 to 22 ring carbon atoms.

25. The compound of claim 1, wherein, when Ar comprises one or more substituents, each substituent is independently a linear, branched, or cyclic alkyl group having 1 to 20 carbon atoms, a haloalkyl group having 1 to 20 carbon atoms, a linear, branched, or cyclic alkylsilyl group having 1 to 10 carbon atoms, a cyano group, a halogen atom, or an aryl group having 6 to 22 ring carbon atoms.

26. The compound of claim 1, wherein, when $Y_1$ or $Y_2$ comprises one or more substituents, each substituent is independently a linear, branched, or cyclic alkyl group having 1 to 20 carbon atoms, a haloalkyl group having 1 to 20 carbon atoms, a linear, branched, or cyclic alkylsilyl group having 1 to 10 carbon atoms, a cyano group, a halogen atom, or an aryl group having 6 to 22 ring carbon atoms.

27. The compound of claim 1, wherein, when $Cz_1$ or $Cz_2$ comprises one or more substituents, each substituent is independently a linear, branched, or cyclic alkyl group having 1 to 20 carbon atoms, a haloalkyl group having 1 to 20 carbon atoms, a linear, branched, or cyclic alkylsilyl group having 1 to 10 carbon atoms, a cyano group, a halogen atom, or an aryl group having 6 to 22 ring carbon atoms.

28. The compound of claim 1, wherein, when any of $L_1$ to $L_7$ comprises one or more substituents, each substituent is independently a linear, branched, or cyclic alkyl group having 1 to 20 carbon atoms, a haloalkyl group having 1 to 20 carbon atoms, a linear, branched, or cyclic alkylsilyl group having 1 to 10 carbon atoms, a cyano group, a halogen atom, or an aryl group having 6 to 22 ring carbon atoms.

* * * * *